United States Patent
Chobanian et al.

(10) Patent No.: US 9,469,608 B2
(45) Date of Patent: Oct. 18, 2016

(54) THROMBIN INHIBITORS

(71) Applicant: Merck Sharp & Dohme Corp., Rahway, NJ (US)

(72) Inventors: Harry Chobanian, Aberdeen, NJ (US); Tesfaye Biftu, Freehold, NJ (US); Barbara Pio, West Orange, NJ (US); Zhicai Wu, Montvale, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/443,470

(22) PCT Filed: Nov. 15, 2013

(86) PCT No.: PCT/US2013/070212
§ 371 (c)(1),
(2) Date: May 18, 2015

(87) PCT Pub. No.: WO2014/081618
PCT Pub. Date: May 30, 2014

(65) Prior Publication Data
US 2015/0315141 A1 Nov. 5, 2015

Related U.S. Application Data

(60) Provisional application No. 61/728,343, filed on Nov. 20, 2012.

(51) Int. Cl.
C07D 207/16 (2006.01)
C07D 207/34 (2006.01)
C07D 401/14 (2006.01)
C07D 401/06 (2006.01)
C07D 405/06 (2006.01)
C07D 409/06 (2006.01)
C07D 403/06 (2006.01)
C07D 417/06 (2006.01)

(52) U.S. Cl.
CPC ........... *C07D 207/16* (2013.01); *C07D 207/34* (2013.01); *C07D 401/06* (2013.01); *C07D 401/14* (2013.01); *C07D 403/06* (2013.01); *C07D 405/06* (2013.01); *C07D 409/06* (2013.01); *C07D 417/06* (2013.01)

(58) Field of Classification Search
None
See application file for complete search history.

(56) References Cited

U.S. PATENT DOCUMENTS 6,515,011 B2  2/2003  Selnick et al.
6,528,503 B2  3/2003  Williams et al.

FOREIGN PATENT DOCUMENTS

WO  WO9631504    10/1996
WO  0250056 A1   6/2002
WO  02064559 A2  8/2002

OTHER PUBLICATIONS

Extended European Search Report for 13857464.5, mailed May 3, 2016, 9 pages.
International Search Report and Written Opinion on the ISR for PCT/US13/70212 mailed Mar. 6, 2014, 11 pages.
Reister, D., et al., Thrombin inhibitors identified by computer-assisted multiparameter design, PNAS, Jun. 14, 2005, pp. 8597-8602, 102-24.

*Primary Examiner* — Timothy R Rozof
(74) *Attorney, Agent, or Firm* — Nicole M. Beeler; Catherine D. Fitch

(57) ABSTRACT

Compounds of the invention, which may be useful in inhibiting thrombin and associated thrombotic occlusions, have the following structure:

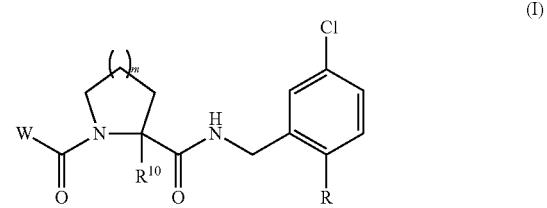

(I)

or a pharmaceutically acceptable salt thereof, wherein
m is 0 or 1;
R is a heterocycle, $-(CR^8R^9)_{1-2}NH_2$, or $-(CR^8R^9)_{1-2}OH$, wherein $R^8$ and $R^9$, each time in which they occur, are independently H, $C_{1-6}$alkyl, $-CH_2F$, $-CHF_2$, $CF_3$ or $-CH_2OH$;
W is
a) $-CHR^1R^2$, where $R^1$ is $-C(CH_3)_3$, and $R^2$ is $-(CH_2)_{1-2}OH$,
b) a 5- or 6-membered unsubstituted or substituted heterocycle having 1 or 2 heteroatoms selected from N and O, wherein substituted heterocycle is substituted with $R^3$,
c) a 9- or 10-membered unsubstituted or substituted heterocycle having 1 or 2 heteroatoms selected from N, O and S, wherein substituted heterocycle is mono-substituted with $R^3$, or disubstituted with $R^3$ and $R^4$,
or
d) a 3-, 4-, or 5-membered carbocyclic ring which is unsubstituted, mono-substituted with $R^3$, di-substituted with $R^3$ and $R^4$, or tri-substituted with $R^3$, $R^4$ and $R^5$;
$R^3$ is $-CF_3$, $-COOH$, $-COOR^7$, $-C(O)R^6$, $-CH(OH)R^6$, $-CH_2R^6$, $R^6$, $=O$, halogen, $R^7$, $-OH$, $-NH_2$, or $-NHSO_2R^7$; and
$R^{10}$ is H or $C_{1-6}$alkyl.

20 Claims, No Drawings

THROMBIN INHIBITORS

BACKGROUND OF THE INVENTION

Thrombin is a serine protease present in blood plasma in the form of a precursor, prothrombin. Thrombin plays a central role in the mechanism of blood coagulation by converting the solution plasma protein, fibrinogen, into insoluble fibrin.

Edwards et al., J. Amer. Chem. Soc., (1992) vol. 114, pp. 1854-63, describes peptidyl α-ketobenzoxazoles which are reversible inhibitors of the serine proteases human leukocyte elastase and porcine pancreatic elastase. European Publication 363 284 describes analogs of peptidase substrates in which the nitrogen atom of the scissile amide group of the substrate peptide has been replaced by hydrogen or a substituted carbonyl moiety. Australian Publication 86245677 also describes peptidase inhibitors having an activated electrophilic ketone moiety such as fluoromethylene ketone or a-keto carboxyl derivatives. R. J. Brown et al., J. Med. Chem., Vol. 37, pages 1259-1261 (1994) describes orally active, non-peptidic inhibitors of human leukocyte elastase which contain trifluoromethylketone and pyridinone moieties. H. Mack et al., J. Enzyme Inhibition, Vol. 9, pages 73-86 (1995) describes rigid amidino-phenylalanine thrombin inhibitors which contain a pyridinone moiety as a central core structure.

SUMMARY OF THE INVENTION

The invention includes compounds for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compounds may optionally include anticoagulants, antiplatelet agents, and thrombolytic agents. The compounds can be added to blood, blood products, or mammalian organs in order to effect the desired inhibitions.

The invention also includes a compound for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compounds may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

DETAILED DESCRIPTION OF THE INVENTION

Compounds of the invention are thrombin inhibitors and may have therapeutic value in, for example, preventing coronary artery disease. The invention includes compounds of formula I:

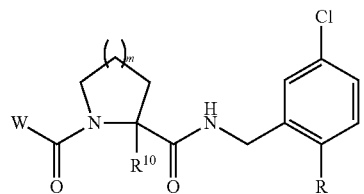

(I)

m is 0 or 1;

R is a heterocycle, $-(CR^8R^9)_{1-2}NH_2$, or $-(CR^8R^9)_{1-2}OH$, wherein $R^8$ and $R^9$, each time in which they occur, are independently H, $C_{1-6}$ alkyl, $-CH_2F$, $-CHF_2$, $CF_3$ or $-CH_2OH$;

W is
a) $-CHR^1R^2$, where $R^1$ is $-C(CH_3)_3$, and $R^2$ is $-(CH_2)_{1-2}OH$,
b) a 5- or 6-membered unsubstituted or substituted heterocycle having 1 or 2 heteroatoms selected from N and O, wherein substituted heterocycle is substituted with $R^3$,
c) a 9- or 10-membered unsubstituted or substituted heterocycle having 1 or 2 heteroatoms selected from N, O and S, wherein substituted heterocycle is mono-substituted with $R^3$, or disubstituted with $R^3$ and $R^4$,
or
d) a 3-, 4-, or 5-membered carbocyclic ring which is unsubstituted, mono-substituted with $R^3$, di-substituted with $R^3$ and $R^4$, or tri-substituted with $R^3$, $R^4$ and $R^5$;

$R^3$ is $-CF_3$, $-COOH$, $-COOR^7$, $-C(O)R^6$, $-CH(OH)R^6$, $-CH_2R^6$, $R^6$, $=O$, halogen, $R^7$, $-OH$, $-NH_2$, or $-NHSO_2R^7$;

$R^4$ is $-OH$, $=O$, or $C_{1-6}$ alkyl;

$R^5$ is $C_{1-6}$ alkyl;

$R^6$ is

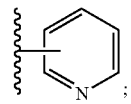;

$R^7$ is $C_{1-6}$ alkyl; and $R^{10}$ is H or $C_{1-6}$ alkyl.

In one embodiment of the invention, R is $-CH_2NH_2$, $-CH_2OH$ or tetrazole.

In another embodiment of the invention, W is $-CH(C(CH_3)_3)CH_2CH_2OH$, or $-CH(C(CH_3)_3)CH_2OH$.

In another embodiment of the invention, W is

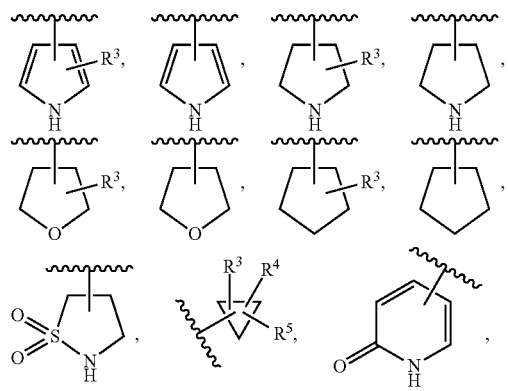

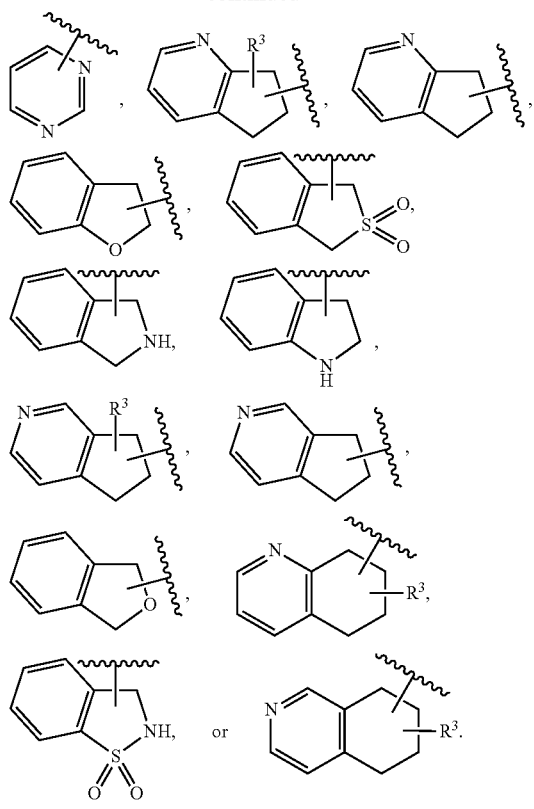

In a class of this embodiment, W is

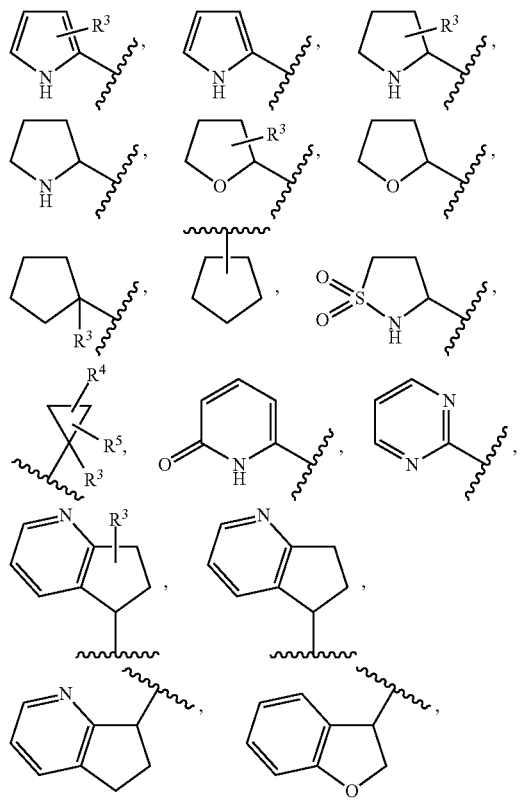

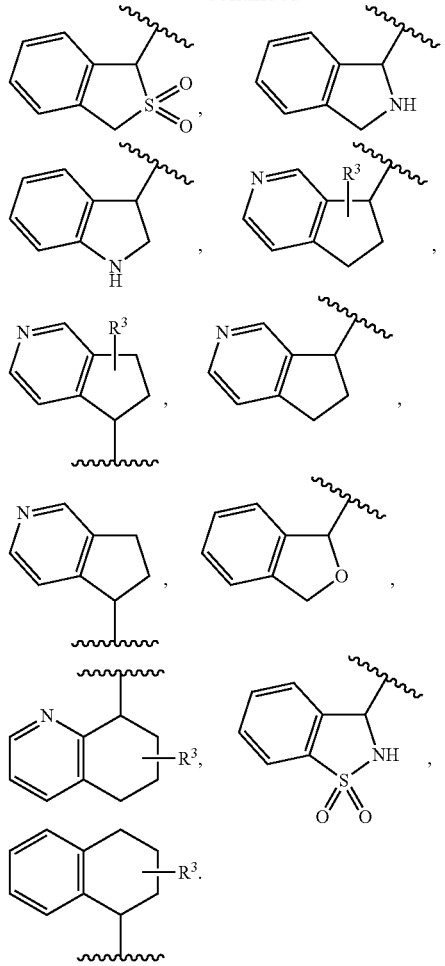

In another embodiment of the invention, $R^3$ is —$CF_3$, COOH, —$COOCH_2CH_3$, Cl, OH, $NH_2$, $NHSO_2CH_3$,

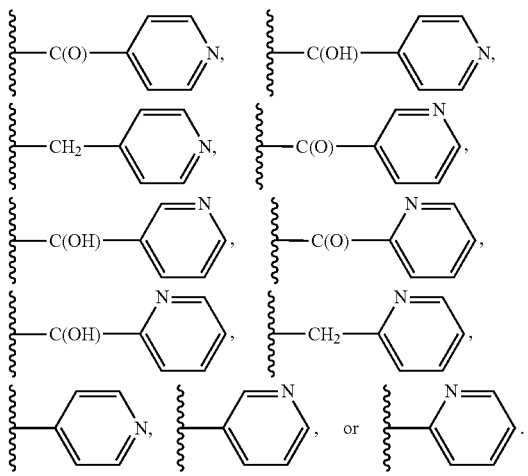

In another embodiment of the invention, $R^4$ is $CH_3$.
In another embodiment of the invention, $R^5$ is $CH_3$.
In another embodiment of the invention, $R^7$ is $CH_3$.
In another embodiment of the invention, $R^{10}$ is H.
In another embodiment of the invention, $R^{10}$ is $CH_3$.

In another embodiment of the invention, R is tetrazole or —CH$_2$NH$_2$.

In another embodiment of the invention, the compound is
- (S)—N-[2-(Aminomethyl)-5-chlorobenzyl]-1-[(R)-2-(2-hydroxyethyl)-3,3-dimethylbutanoyl]pyrrolidine-2-carboxamide-2,2,2-trifluoroacetate,
- (S)—N-[2-(Aminomethyl)-5-chlorobenzyl]-1-[4-(trifluoromethyl)-1H-pyrrole-2-carbonyl]pyrrolidine-2-carboxamide-2,2,2-trifluoroacetate,
- (S)-Ethyl-5-[2-{(2-(aminomethyl)-5-chlorobenzyl)carbamoyl}pyrrolidine-1-carbonyl]-1H-pyrrole-2-carboxylate-2,2,2-trifluoroacetate,
- (S)—N-{2-(Aminomethyl)-5-chlorobenzyl}-1-{5-(trifluoromethyl)-1H-pyrrole-2-carbonyl}pyrrolidine-2-carboxamide,
- (S)—N-{2-(Aminomethyl)-5-chlorobenzyl}-1-(4-nicotinoyl-1H-pyrrole-2-carbonyl)pyrrolidine-2-carboxamide-bis(2,2,2-trifluoro acetate),
- (2S)-N-{2-(Aminomethyl)-5-chlorobenzyl}-1-[4-{hydroxyl(pyridine-4-yl)methyl}-1H-pyrrole-2-carbonyl]pyrrolidine-2-carboxamide-bis(2,2,2-trifluoroacetate),
- (S)—N-{2-(Aminomethyl)-5-chlorobenzyl}-1-{4-(pyridin-4-ylmethyl)-1H-pyrrole-2-carbonyl}pyrrolidine-2-carboxamide-bis(2,2,2-trifluoroacetate),
- (S)—N-{2-(aminomethyl)-5-chlorobenzyl}-1-(4-nicotinoyl-1H-pyrrole-2-carbonyl)pyrrolidine-2-carboxamide-bis(2,2,2-trifluoro acetate,
- (2S)-N-{2-(Aminomethyl)-5-chlorobenzyl}-1-[4-{hydroxy(pyridine-3-yl)methyl]-1H-pyrrole-2-carbonyl)pyrrolidine-2-carboxamide,
- (S)—N-{2-(Aminomethyl)-5-chlorobenzyl}-1-(4-picolinoyl-1H-pyrrole-2-carbonyl)pyrrolidine-2-carboxamide-bis(2,2,2-trifluoro acetate,
- (2S)-N-{2-(Aminomethyl)-5-chlorobenzyl}-1-[4-{hydroxyl(pyridine-2-yl)methyl}-1H-pyrrole-2-carbonyl]pyrrolidine-2-carboxamide,
- (S)—N-{2-(Aminomethyl)-5-chlorobenzyl}-1-{4-(pyridin-2-ylmethyl)-1H-pyrrole-2-carbonyl}pyrrolidine-2-carboxamide-bis(2,2,2-trifluoroacetate),
- (S)—N-{2-(Aminomethyl)-5-chlorobenzyl)-1-{4-(pyridin-4-yl)-1H-pyrrole-2-carbonyl) pyrrolidine-2-carboxamide-bis(2,2,2-trifluoroacetate),
- (S)—N-{2-(Aminomethyl)-5-chlorobenzyl}-1-{4-(pyridin-3-yl)-1H-pyrrole-2-carbonyl}pyrrolidine-2-carboxamide bis(2,2,2-trifluoroacetate),
- (S)—N-[{2-(Aminomethyl)-5-chlorobenzyl}-1-{4-(pyridin-2-yl)-1H-pyrrole-2-carbonyl}]pyrrolidine-2-carboxamide bis (2,2,2-trifluoroacetate),
- (S)—N-{2-(aminomethyl)-5-chlorobenzyl}-1-{(S)-2-(hydroxymethyl)-3,3-dimethylbutanoyl}pyrrolidine-2-carboxamide-2,2,2-trifluoroacetate,
- (S)—N-{5-Chloro-2-(hydroxymethyl)benzyl}-1-{(R)-2-hydroxy-3,3-dimethyl butanoyl}pyrrolidine-2-carboxamide,
- (S)—N-{2-(Aminomethyl)-5-chlorobenzyl}-1-(6-oxo-1,6-dihydropyridine-2-carbonyl)pyrrolidine-2-carboxamide-2,2,2-trifluoroacetate,
- (2S)-N-{2-(Aminomethyl)-5-chlorobenzyl}-1-(5-hydroxy-6,7-dihydro-5H-cyclopenta[b]pyridine-5-carbonyl)pyrrolidine-2-carboxamide-2,2,2-trifluoroacetate,
- (2S)-N-(2-(Aminomethyl)-5-chlorobenzyl)-1-(7-hydroxy-6,7-dihydro-5H-cyclopenta[b]pyridine-7-carbonyl)pyrrolidine-2-carboxamide-bis(2,2,2-trifluoroacetate),
- (2S)-N-{2-(Aminomethyl)-5-chlorobenzyl}-1-(1,3-dihydroisobenzofuran-1-carbonyl)pyrrolidine-2-carboxamide-2,2,2-trifluoroacetate,
- (2S)-N-{2-(Aminomethyl)-5-chlorobenzyl}-1-(2,2-dioxido-1,3-dihydrobenzo[a]thiophene-1-carbonyl)pyrrolidine-2-carboxamide-2,2,2-trifluoroacetate-2,2,2-trifluoroacetate,
- (2S)-N-{2-(Aminomethyl)-5-chlorobenzyl}-1-(isoindoline-1-carbonyl)pyrrolidine-2-carboxamide bis(2,2,2-trifluoroacetate),
- (2S)-N-{2-(Aminomethyl)-5-chlorobenzyl}-1-(isoindoline-1-carbonyl)pyrrolidine-2-carboxamide bis(2,2,2-trifluoroacetate) Isomer A,
- (2S)-N-{2-(Aminomethyl)-5-chlorobenzyl}-1-(isoindoline-1-carbonyl)pyrrolidine-2-carboxamide bis(2,2,2-trifluoroacetate) Isomer B,
- (2S)-N-{2-(Aminomethyl)-5-chlorobenzyl}-1-(2,3-dihydrobenzofuran-3-carbonyl)pyrrolidine-2-carboxamide-2,2,2-trifluoroacetate,
- (2S)-N-{2-(Aminomethyl)-5-chlorobenzyl}-1-(indoline-3-carbonyl)pyrrolidine-2-carboxamide bis(2,2,2-trifluoroacetate),
- (2S)-N-{2-(Aminomethyl)-5-chlorobenzyl}-1-(5-hydroxy-6,7-dihydro-5H-cyclopenta[b]pyridine-5-carbonyl}azetidine-2-carboxamide bis(2,2,2-trifluoroacetate),
- {(2S)-N-{2-(Aminomethyl)-5-chlorobenzyl}-1-(5-hydroxy-6,7-dihydro-5H-cyclopenta[c]pyridine-5-carbonyl)pyrrolidine-2-carboxamide bis(2,2,2-trifluoroacetate),
- (2S)-N-{2-(aminomethyl)-5-chlorobenzyl)-1-(7-hydroxy-6,7-dihydro-5H-cyclopenta[c]pyridine-7-carbonyl)pyrrolidine-2-carboxamide bis (2,2,2-trifluoroacetate),
- (2S)-1-(7-Amino-6,7-dihydro-5H-cyclopenta[b]pyridine-7-carbonyl)-N-(2-(aminomethyl)-5-chlorobenzyl)pyrrolidine-2-carboxamide tris(2,2,2-trifluoroacetate),
- (2S)-1-(7-Amino-6,7-dihydro-5H-cyclopenta[b]pyridine-7-carbonyl)-N-(2-(aminomethyl)-5-chlorobenzyl)pyrrolidine-2-carboxamide tris(2,2,2-trifluoroacetate) Isomer A,
- (2S)-1-(7-Amino-6,7-dihydro-5H-cyclopenta[b]pyridine-7-carbonyl)-N-(2-(aminomethyl)-5-chlorobenzyl)pyrrolidine-2-carboxamide tris(2,2,2-trifluoroacetate) Isomer B,
- (2S)-N-{2-(Aminomethyl)-5-chlorobenzyl}-1-(5-hydroxy-5,6,7,8-tetrahydroquinoline-5-carbonyl)pyrrolidine-2-carboxamide bis(2,2,2-trifluoroacetate),
- (2S)-N-{2-(Aminomethyl)-5-chlorobenzyl}-1-(5-hydroxy-5,6,7,8-tetrahydroisoquinoline-5-carbonyl)pyrrolidine-2-carboxamide bis(2,2,2-trifluoroacetate),
- (2S)-N-{2-(aminomethyl)-5-chlorobenzyl}-1-(8-hydroxy-5,6,7,8-tetrahydroquinoline-8-carbonyl)pyrrolidine-2-carboxamide bis(2,2,2-trifluoroacetate),
- (2S)-N-{2-(Aminomethyl)-5-chlorobenzyl}-1-(1,3-dihydroisobenzofuran-1-carbonyl)azetidine-2-carboxamide-2,2,2-trifluoroacetate,
- (2S)-N-{2-(aminomethyl)-5-chlorobenzyl}-1-(isoindoline-1-carbonyl)azetidine-2-carboxamide bis(2,2,2-trifluoroacetate),
- (2S)-N-{2-(Aminomethyl)-5-chlorobenzyl}-1-(indoline-3-carbonyl)azetidine-2-carboxamide bis(2,2,2-trifluoroacetate),
- (2S)-N-{5-Chloro-2-(1H-tetrazol-1-yl)benzyl}-1-(7-hydroxy-6,7-dihydro-5H-cyclopenta[b]pyridine-7-carbonyl)pyrrolidine-2-carboxamide,
- (S)—N-{2-(Aminomethyl)-5-chlorobenzyl}-1-{(R)-1-hydroxy-2,2-dimethylcyclopropanecarbonyl)pyrrolidine-2-carboxamide-2,2,2-trifluoroacetate,
- (S)—N-{2-(Aminomethyl)-5-chlorobenzyl}-1-{(R)-1-hydroxy-2,2-dimethylcyclopropanecarbonyl)pyrrolidine-2-carboxamide-2,2,2-trifluoroacetate Isomer A,
- (S)—N-{2-(Aminomethyl)-5-chlorobenzyl}-1-{(R)-1-hydroxy-2,2-dimethylcyclopropanecarbonyl)pyrrolidine-2-carboxamide-2,2,2-trifluoroacetate Isomer B, (S)—N-{2-(Aminomethyl)-5-chlorobenzyl}-1-{(R)-tetrahydrofuran-2-carbonyl}pyrrolidine-2-carboxamide-2,2,2-trifluoroacetate, (S)—N-{2-(Aminomethyl)-5-chlorobenzyl}-1-(5-ethoxy-1H-pyrrole-2-carbonyl)pyrrolidine-2-carboxamide-2,2,2-trifluoroacetate, (S)—N-{2-(Aminomethyl)-5-chlorobenzyl}-1-(5-ethoxy-1H-pyrrole-2-carbonyl)pyrrolidine-2-carboxamide-2,2,2-trifluoroacetate Isomer A, (S)—N-{2-(Aminomethyl)-5-chlorobenzyl}-1-(5-ethoxy-1H-pyrrole-2-carbonyl)pyrrolidine-2-carboxamide-2,2,2-trifluoroacetate Isomer B, (S)-1-(1-Aminocyclopentanecarbonyl)-N-{2-(aminomethyl)-5-chlorobenzyl}pyrrolidine-2-carboxamide-2,2,2-trifluoroacetate, (S)—N-{2-(Aminomethyl)-5-chlorobenzyl}-1-{1-(methylsulfonamido)cyclopentanecarbonyl}pyrrolidine-2-carboxamide-2,2,2-trifluoroacetate, (S)—N-(2-(Aminomethyl)-5-chlorobenzyl)-1-(pyrimidine-2-carbonyl)pyrrolidine-2-carboxamide bis(2,2,2-trifluoroacetate), (S)—N-(2-(aminomethyl)-5-chlorobenzyl)-2-methyl-1-((R)-5-oxopyrrolidine-2-carbonyl)pyrrolidine-2-carboxamide, (S)—N-(2-(aminomethyl)-5-chlorobenzyl)-1-(5-chloro-1H-pyrrole-2-carbonyl)-2-methylpyrrolidine-2-carboxamide, or (S)—N-(2-(aminomethyl)-5-chlorobenzyl)-2-methyl-1-(5-methyl-1H-pyrrole-2-carbonyl)pyrrolidine-2-carboxamide.

Table 1 shows structures and names of compounds of the invention:

TABLE 1

| Compound | Structure | Name-Ki (nM) |
|---|---|---|
| 1-12 | 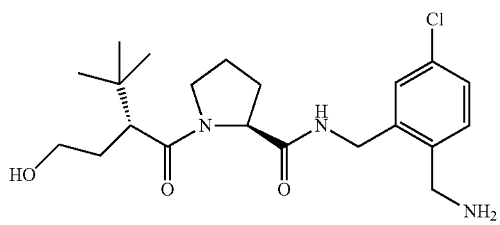 | (S)-N-(Aminomethyl)-5-chlorobenzyl]-1-[(R)-2-(2-hydroxyethyl)-3,3-dimethylbutanoyl]pyrrolidine-2-carboxamide-2,2,2-trifluoroacetate (25 nM) |
| 2-11 | 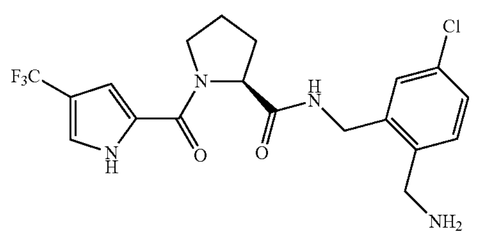 | (S)-N-[2-(Aminomethyl)-5-chlorobenzyl]-1-[4-(trifluoromethyl)-1H-pyrrole-2-carbonyl]pyrrolidine-2-carboxamide-2,2,2-trifluoroacetate (110 nM) |
| 3-5 | 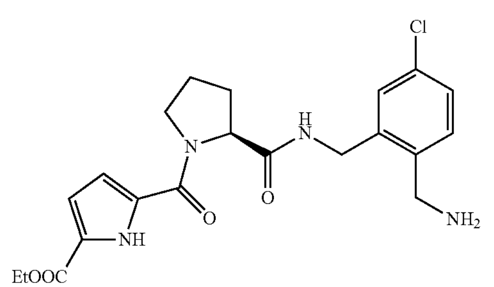 | (S)-Ethyl-5-[2-{(2-(aminomethyl)-5-chlorobenzyl)carbamoyl(pyrrolidine-1-carbonyl]-1H-pyrrole-2-carboxylate-2,2,2-trifluoroacetate (47 nM) |
| 4-5 | 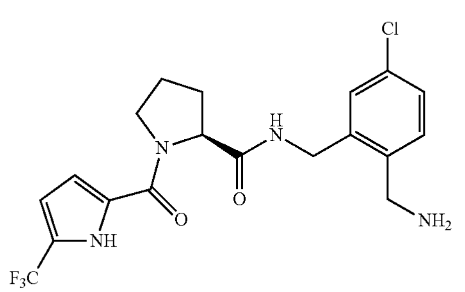 | (S)-N-{2-(Aminomethyl)-5-chlorobenzyl}-1-{5-(trifluoromethyl)-1H-pyrrole-2-carbonyl}pyrrolidine-2-carboxamide (27 nM) |

TABLE 1-continued

| Compound | Structure | Name-Ki (nM) |
|---|---|---|
| 5-9 | 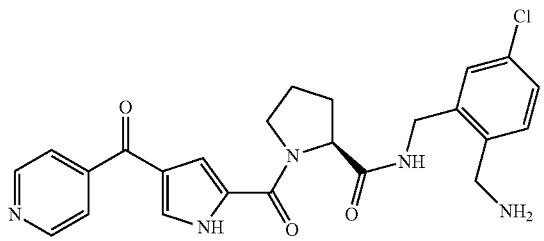 [SMILES: NCc1ccc(Cl)cc1CNC(=O)[C@@H]1CCCN1C(=O)c1cc(C(=O)c2ccncc2)c[nH]1] | (S)-N-{2-(Aminomethyl)-5-chlorobenzyl}-1-(4-nicotinoyl-1H-pyrrole-2-carbonyl)pyrrolidine-2-carboxamide-bis(2,2,2-trifluoro acetate) (87 nM) |
| 6-2 | 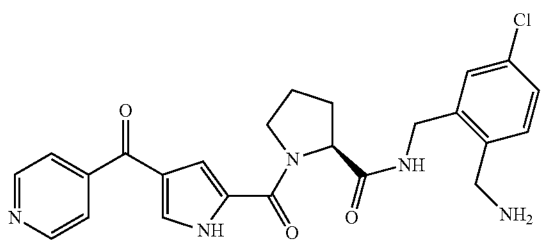 | (2S)-N-{2-(Aminomethyl)-5-chlorobenzyl}-1-[4-{hydroxyl(pyridine-4-yl)methyl}-1H-pyrrole-2-carbonyl]pyrrolidine-2-carboxamide-bis(2,2,2-trifluoroacetate) (21 nM) |
| 7-1 | 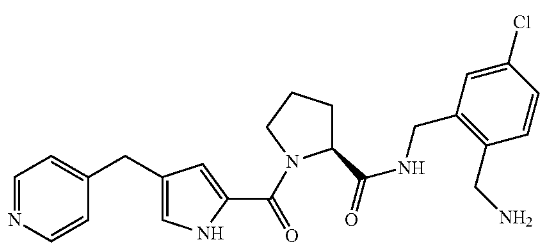 | (S)-N-{2-(Aminomethyl)-5-chlorobenzyl}-1-{4-(pyridin-4-ylmethyl)-1H-pyrrole-4-carbonyl}pyrrolidine-2-carboxamide-bis(2,2,2-trifluoroacetate) (17 nM) |
| 8-8 | 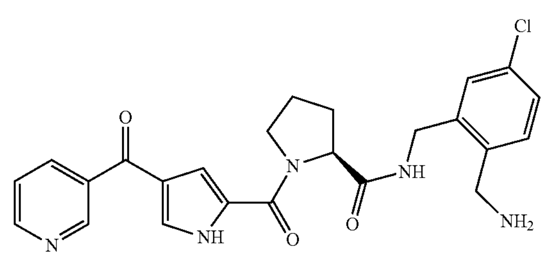 [SMILES: NCc1ccc(Cl)cc1CNC(=O)[C@@H]1CCCN1C(=O)c1cc(C(O)c2cccnc2)c[nH]1] | (S)-N-{2-(aminomethyl)-5-chlorobenzyl}-1-(4-nicotinoyl-1H-pyrrole-2-carbonyl)pyrrolidine-2-carboxamide-bis(2,2,2-trifluoro acetate (18 nM) |
| 9-2 | 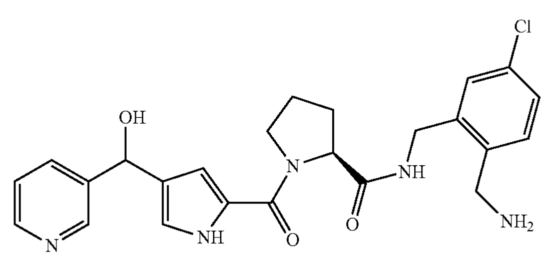 | (2S)-N-{2-(Aminomethyl)-5-chlorobenzyl}-1-[4-{hydroxy(pyridine-3-yl}methyl]-1H-pyrrole-2-carbonyl)pyrrolidine-2-carboxamide (13 nM) |

TABLE 1-continued

| Compound | Structure | Name-Ki (nM) |
|---|---|---|
| 10-7 | 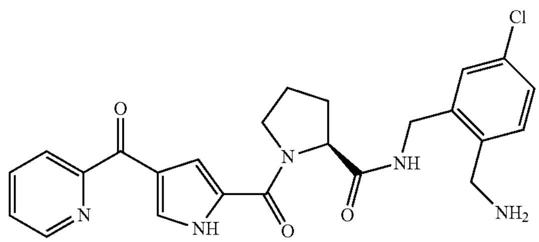 | (S)-N-{2-(Aminomethyl)-5-chlorobenzyl}-1-(4-picolinoyl-1H-pyrrole-2-carbonyl)pyrrolidine-2-carboxamide-bis(2,2,2-trifluoro acetate) (17 nM) |
| 11-2 | 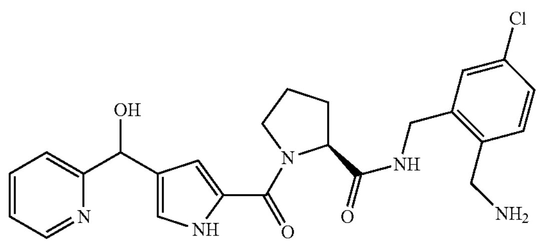 [SMILES: NCc1ccc(Cl)cc1CNC(=O)[C@@H]1CCCN1C(=O)c1cc(C(O)c2ccccn2)c[nH]1] | (2S)-N-{2-(Aminomethyl)-5-chlorobenzyl}-1-[4-{hydroxyl (pyridine-2-yl)methyl}-1H-pyrrole-2-carbonyl]pyrrolidine-2-carboxamide (9.7 nM) |
| 12-1 | 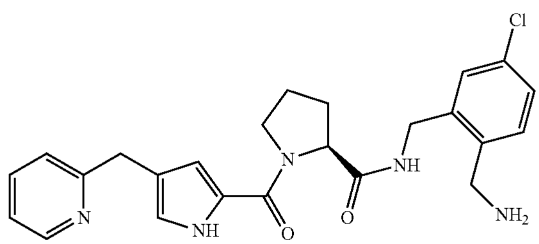 | (S)-N-{2-(Aminomethyl)-5-chlorobenzyl}-1-{4-(pyridin-2-ylmethyl)-1H-pyrrole-2-carbonyl}pyrrolidine-2-carboxamide-bis(2,2,2-trifluoroacetate) |
| 13-10 | 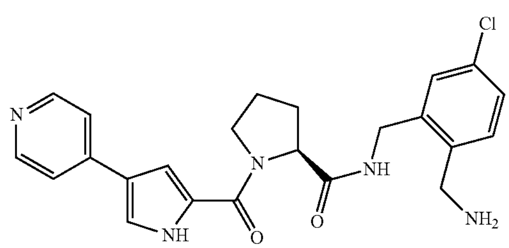 | (S)-N-{2-(Aminomethyl)-5-chlorobenzyl)-1-(4-(pyridin-4-yl)-1H-pyrrole-2-carbonyl)pyrrolidine-2-carboxamide-bis(2,2,2-trifluoroacetate) (3.4 nM) |
| 14-5 | 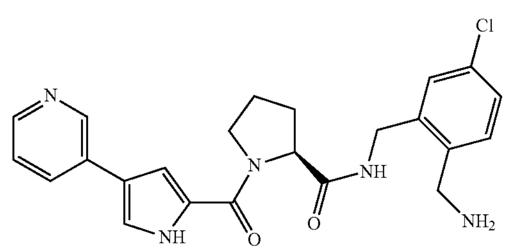 | (S)-N-{2-(Aminomethyl)-5-chlorobenzyl}-1-{4-(pyridin-3-yl)-1H-pyrrole-2-carbonyl}pyrrolidine-2-carboxamide bis(2,2,2-trifluoroacetate) (22 nM) |

TABLE 1-continued

| Compound | Structure | Name-Ki (nM) |
|---|---|---|
| 15-8 | 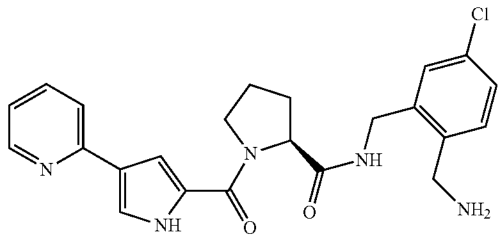 | (S)-N-[{2-(Aminomethyl)-5-chlorobenzyl}-1-{4-(pyridin-2-yl)-1H-pyrrole-2-carbonyl}]pyrrolidine-2-carboxamide bis (2,2,2-trifluoroacetate) (22 nM) |
| 16-9 | 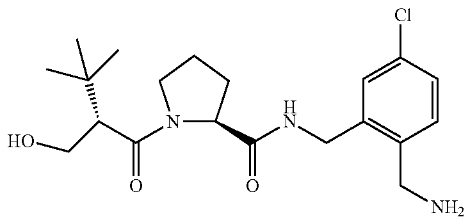 | (S)-N-{2-(aminomethyl)-5-chlorobenzyl}-1-{(S)-2-(hydroxymethyl)-3,3-dimethylbutanoyl}pyrrolidine-2-carboxamide-2,2,2-trifluoroacetate |
| 17-5 | 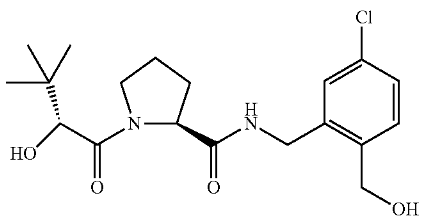 [SMILES: CC(C)(C)[C@@H](O)C(=O)N1CCC[C@H]1C(=O)NCc1cc(Cl)ccc1CO] | (S)-N-{5-Chloro-2-(hydroxymethyl)benzyl}-1-{(R)-2-hydroxy-3,3-dimethyl butanoyl}pyrrolidine-2-carboxamide (3500 nM) |
| 18-4 | 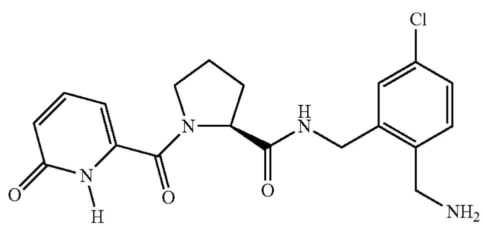 | (S)-N-{2-(Aminomethyl)-5-chlorobenzyl}-1-(6-oxo-1,6-dihydropyridine-2-carbonyl)pyrrolidine-2-carboxamide-2,2,2-trifluoroacetate |
| 19-4 | 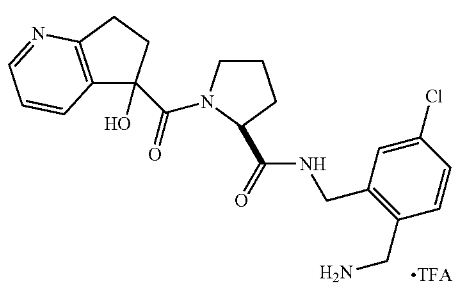 [SMILES: NCc1ccc(Cl)cc1CNC(=O)[C@@H]1CCCN1C(=O)C1(O)CCc2ncccc21] | (2S)-N-{2-(Aminomethyl)-5-chlorobenzyl}-1-(5-hydroxy-6,7-dihydro-5H-cyclopenta[b]pyridine-5-carbonyl)pyrrolidine-2-carboxamide-2,2,2-trifluoroacetate (49 nM) |
| 20-8 | 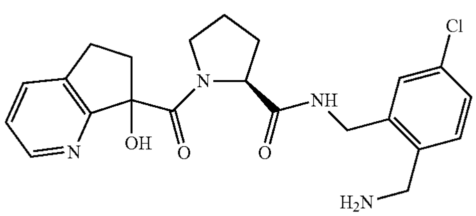 | (2S)-N-(Aminomethyl)-5-chlorobenzyl)-1-(7-hydroxy-6,7-dihydro-5H-cyclopenta[b]pyridine-7-carbonyl)pyrrolidine-2-carboxamide-bis(2,2,2-trifluoroacetate) (7.7 nM) |

TABLE 1-continued

| Compound | Structure | Name-Ki (nM) |
|---|---|---|
| 21-6 | 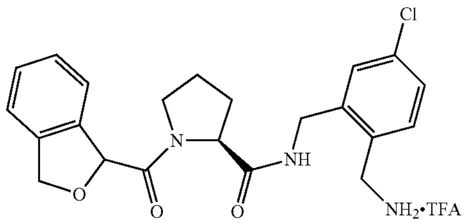 | (2S)-N-{2-(Aminomethyl)-5-chlorobenzyl}-1-(1,3-dihydroisobenzofuran-1-carbonyl)pyrrolidine-2-carboxamide-2,2,2-trifluoroacetate (15 nM) |
| 22-10 | 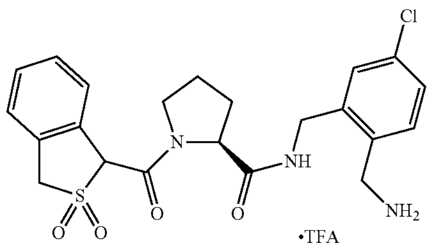 [SMILES: NCc1ccc(Cl)cc1CNC(=O)[C@@H]1CCCN1C(=O)C1c2ccccc2CS1(=O)=O] | (2S)-N-{2-(Aminomethyl)-5-chlorobenzyl}-1-(2,2-dioxido-1,3-dihydrobenzo[a]thiophene-1-carbonyl)pyrrolidine-2-carboxamide-2,2,2-trifluoroacetate-2,2,2-trifluoroacetate (400 nM) |
| 23-4a | 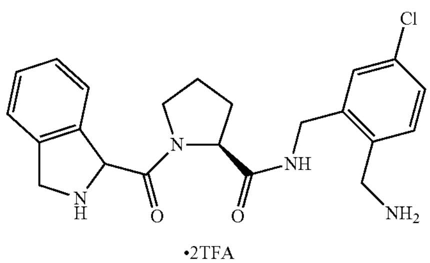 [SMILES: NCc1ccc(Cl)cc1CNC(=O)[C@@H]1CCCN1C(=O)C1NCc2ccccc21] | (2S)-N-{2-(Aminomethyl)-5-chlorobenzyl}-1-(isoindoline-1-carbonyl)pyrrolidine-2-carboxamide bis(2,2,2-trifluoroacetate) Isomer A (77 nM) |
| 23-4b | 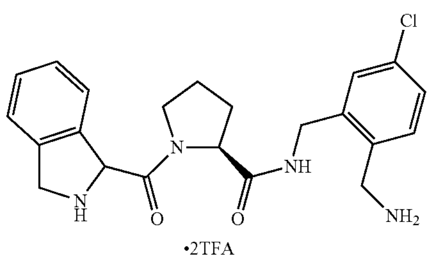 [SMILES: NCc1ccc(Cl)cc1CNC(=O)[C@@H]1CCCN1C(=O)C1NCc2ccccc21] | (2S)-N-{2-(Aminomethyl)-5-chlorobenzyl}-1-(isoindoline-1-carbonyl)pyrrolidine-2-carboxamide bis(2,2,2-trifluoroacetate) Isomer B (1.1 nM) |
| 24-8 | 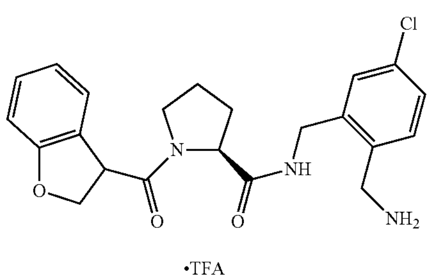 [SMILES: NCc1ccc(Cl)cc1CNC(=O)[C@@H]1CCCN1C(=O)C1COc2ccccc21] | (2S)-N-{2-(Aminomethyl)-5-chlorobenzyl}-1-(2,3-dihydrobenzofuran-3-carbonyl)pyrrolidine-2-carboxamide-2,2,2-trifluoroacetate (9.2 nM) |
| 25-5 | 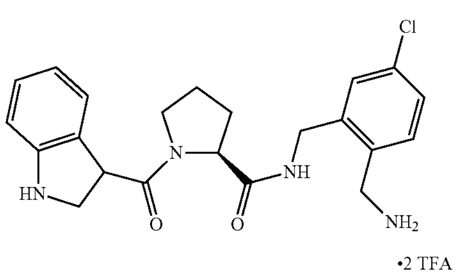 [SMILES: NCc1ccc(Cl)cc1CNC(=O)[C@@H]1CCCN1C(=O)C1CNc2ccccc21] | (2S)-N-{2-(Aminomethyl)-5-chlorobenzyl}-1-(indoline-3-carbonyl)pyrrolidine-2-carboxamide bis(2,2,2-trifluoroacetate) (59 nM) |

TABLE 1-continued

| Compound | Structure | Name-Ki (nM) |
|---|---|---|
| 26-12 | 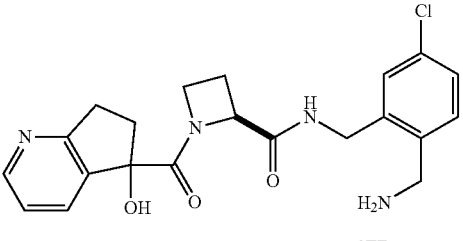 | (2S)-N-{2-(Aminomethyl)-5-chlorobenzyl}-1-(5-hydroxy-6,7-dihydro-5H-cyclopenta[b]pyridine-5-carbonyl}azetidine-2-carboxamide bis(2,2,2-trifluoroacetate) (325 nM) |
| 27-9 | 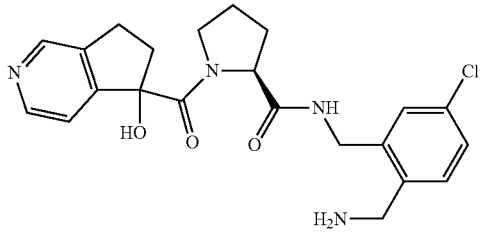 | {(2S)-N-{2-(Aminomethyl)-5-chlorobenzyl}-1-(5-hydroxy-6,7-dihydro-5H-cyclopenta[c]pyridine-5-carbonyl)pyrrolidine-2-carboxamide bis(2,2,2-trifluoroacetate) (20 nM) |
| 28-6 | 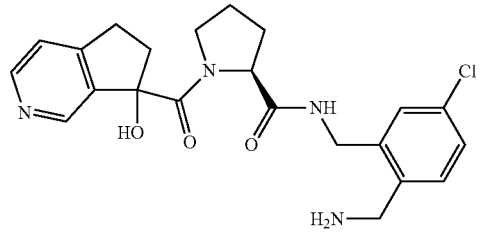 | (2S)-N-{2-(aminomethyl)-5-chlorobenzyl}-1-(7-hydroxy-6,7-dihydro-5H-cyclopenta[c]pyridine-7-carbonyl)pyrrolidine-2-carboxamide bis (2,2,2-trifluoroacetate) (16 nM) |
| 29-9a | 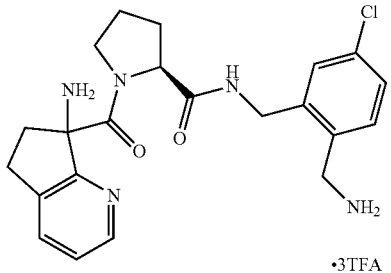 [SMILES: NCc1ccc(Cl)cc1CNC(=O)[C@@H]1CCCN1C(=O)C1(N)CCc2cccnc21] | (2S)-1-(7-Amino-6,7-dihydro-5H-cyclopenta[b]pyridine-7-carbonyl)-N-(2-(aminomethyl)-5-chlorobenzyl)pyrrolidine-2-carboxamide tris(2,2,2-trifluoroacetate) Isomer A (30 nM) |
| 29-9b | 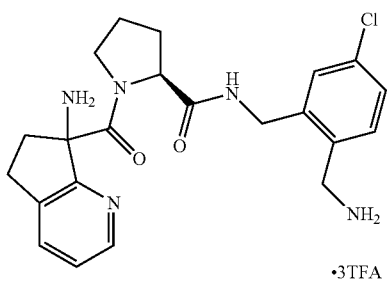 [SMILES: NCc1ccc(Cl)cc1CNC(=O)[C@@H]1CCCN1C(=O)C1(N)CCc2cccnc21] | (2S)-1-(7-Amino-6,7-dihydro-5H-cyclopenta[b]pyridine-7-carbonyl)-N-(2-(aminomethyl)-5-chlorobenzyl)pyrrolidine-2-carboxamide tris(2,2,2-trifluoroacetate) Isomer B (100 nM) |

TABLE 1-continued

| Compound | Structure | Name-Ki (nM) |
|---|---|---|
| 30-6 | 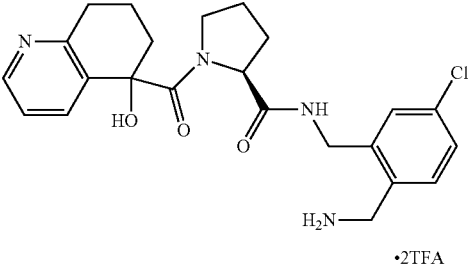 [SMILES: NCc1ccc(Cl)cc1CNC(=O)[C@@H]1CCCN1C(=O)C1(O)CCCc2ncccc21] | (2S)-N-{2-(Aminomethyl)-5-chlorobenzyl}-1-(5-hydroxy-5,6,7,8-tetrahydroquinoline-5-carbonyl)pyrrolidine-2-carboxamide bis(2,2,2-trifluoroacetate) (11 nM) |
| 31-7 | 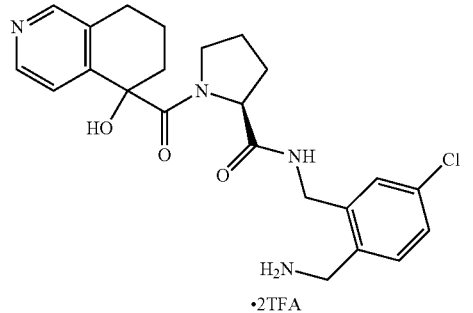 [SMILES: NCc1ccc(Cl)cc1CNC(=O)[C@@H]1CCCN1C(=O)C1(O)CCCc2cnccc21] | (2S)-N-{2-(Aminomethyl)-5-chlorobenzyl}-1-(5-hydroxy-5,6,7,8-tetrahydroisoquinoline-5-carbonyl)pyrrolidine-2-carboxamide bis(2,2,2-trifluoroacetate) (4.8 nM) |
| 32-7 | 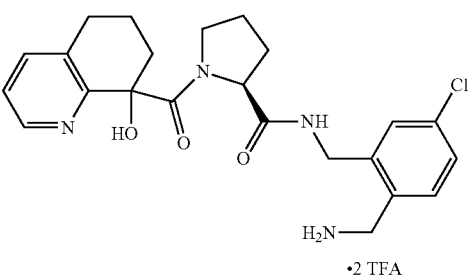 [SMILES: NCc1ccc(Cl)cc1CNC(=O)[C@@H]1CCCN1C(=O)C1(O)CCCc2cccnc21] | (2S)-N-{2-(aminomethyl)-5-chlorobenzyl}-1-(8-hydroxy-5,6,7,8-tetrahydroquinoline-8-carbonyl)pyrrolidine-2-carboxamide bis(2,2,2-trifluoroacetate) (3.9 nM) |
| 33-7 | 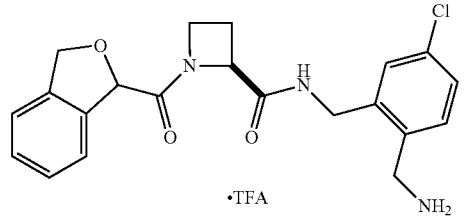 [SMILES: NCc1ccc(Cl)cc1CNC(=O)[C@@H]1CCN1C(=O)C1OCc2ccccc21] | (2S)-N-{2-(Aminomethyl)-5-chlorobenzyl}-1-(1,3-dihydroisobenzofuran-1-carbonyl)azetidine-2-carboxamide-2,2,2-trifluoroacetate (39 nM) |
| 34-7 | 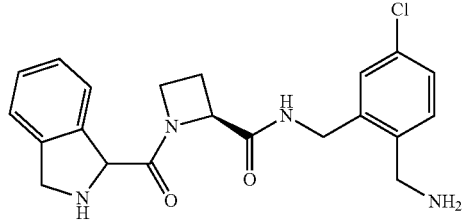 | (2S)-N-{2-(aminomethyl)-5-chlorobenzyl}-1-(isoindoline-1-carbonyl)azetidine-2-carboxamide bis(2,2,2-trifluoroacetate) (2.5 nM) |

TABLE 1-continued

| Compound | Structure | Name-Ki (nM) |
|---|---|---|
| 35-7 | 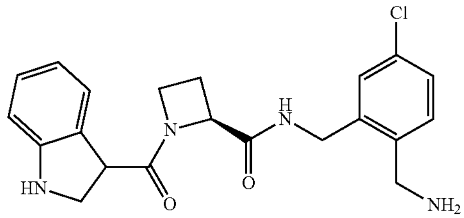 | (2S)-N-{2-(Aminomethyl)-5-chlorobenzyl}-1-(indoline-3-carbonyl)azetidine-2-carboxamide bis(2,2,2-trifluoroacetate) (110 nM) |
| 36-3 | 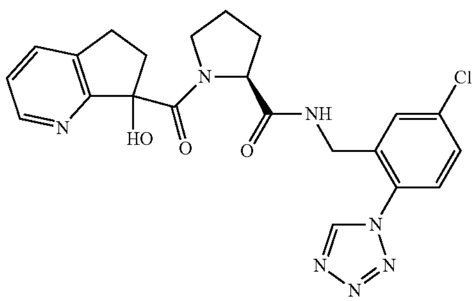 [SMILES: O=C(NCc1cc(Cl)ccc1-n1cnnn1)[C@@H]1CCCN1C(=O)C1(O)CCc2cccnc21] | (2S)-N-{5-Chloro-2-(1H-tetrazol-1-yl)benzyl}-1-(7-hydroxy-6,7-dihydro-5H-cyclopenta[b]pyridine-7-carbonyl)pyrrolidine-2-carboxamide (2.5 nM) |
| 37-11a | 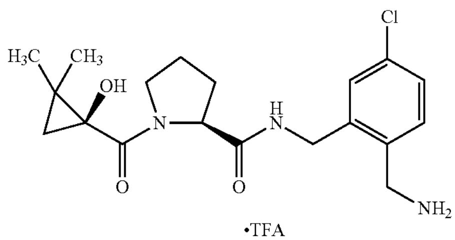 [SMILES: CC1(C)C[C@@]1(O)C(=O)N1CCC[C@H]1C(=O)NCc1cc(Cl)ccc1CN] | (S)-N-{2-(Aminomethyl)-5-chlorobenzyl}-1-{(R)-1-hydroxy-2,2-dimethylcyclopropanecarbonyl)pyrrolidine-2-carboxamide-2,2,2-trifluoroacetate Isomer A (720 nM) |
| 37-11b | 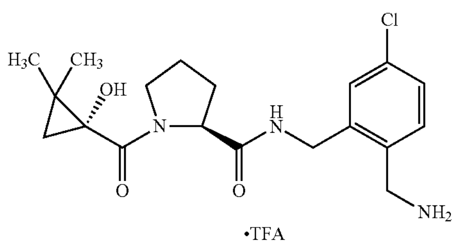 [SMILES: CC1(C)C[C@]1(O)C(=O)N1CCC[C@H]1C(=O)NCc1cc(Cl)ccc1CN] | (S)-N-{2-(Aminomethyl)-5-chlorobenzyl}-1-{(R)-1-hydroxy-2,2-dimethylcyclopropanecarbonyl)pyrrolidine-2-carboxamide-2,2,2-trifluoroacetate Isomer B (65 nM) |
| 38-4 | 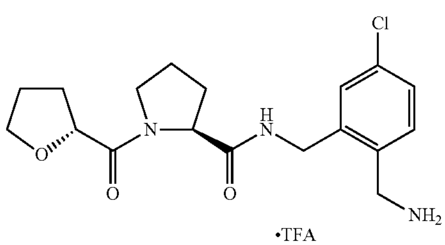 [SMILES: NCc1ccc(Cl)cc1CNC(=O)[C@@H]1CCCN1C(=O)[C@H]1CCCO1] | (S)-N-{2-(Aminomethyl)-5-chlorobenzyl}-1-{(R)-tetrahydrofuran-2-carbonyl}pyrrolidine-2-carboxamide-2,2,2-trifluoroacetate (100 nM) |
| 39-10a | 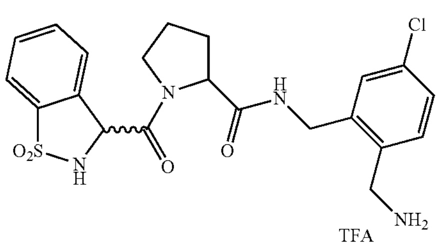 [SMILES: NCc1ccc(Cl)cc1CNC(=O)C1CCCN1C(=O)C1NS(=O)(=O)c2ccccc21] | (S)-N-{2-(Aminomethyl)-5-chlorobenzyl}-1-(5-ethoxy-1H-pyrrole-2-carbonyl)pyrrolidine-2-carboxamide-2,2,2-trifluoroacetate Isomer A (3.4 nM) |

TABLE 1-continued

| Compound | Structure | Name-Ki (nM) |
|---|---|---|
| 39-10b | 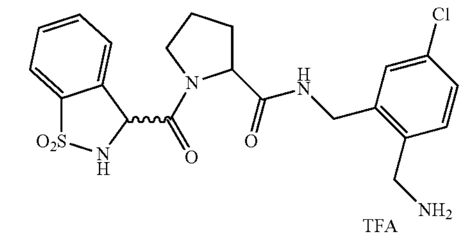 [SMILES: NCc1ccc(Cl)cc1CNC(=O)C1CCCN1C(=O)C1NS(=O)(=O)c2ccccc21] | (S)-N-{2-(Aminomethyl)-5-chlorobenzyl}-1-(5-ethoxy-1H-pyrrole-2-carbonyl)pyrrolidine-2-carboxamide-2,2,2-trifluoroacetate Isomer B (3.4 nM) |
| 40-4 | 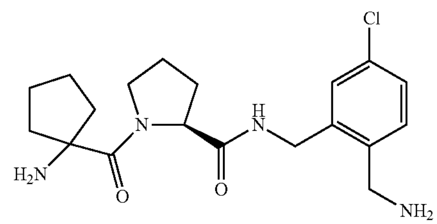 | (S)-1-(1-Aminocyclopentanecarbonyl)-N-{2-(aminomethyl)-5-chlorobenzyl}pyrrolidine-2-carboxamide-2,2,2-trifluoroacetate |
| 41-5 | 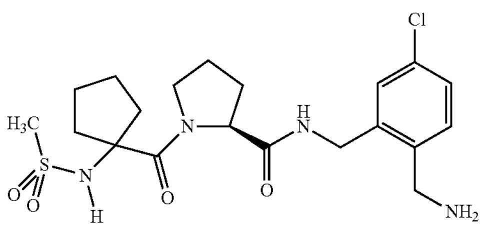 | (S)-N-{2-(Aminomethyl)-5-chlorobenzyl}-1-{1-(methylsulfonamido)cyclopentanecarbonyl}pyrrolidine-2-carboxamide-2,2,2-trifluoroacetate |
| 42-3 | 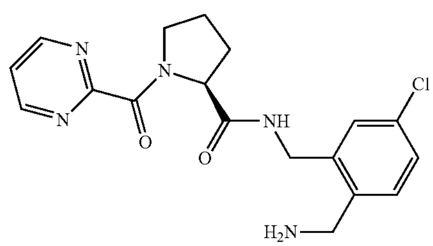 | (S)-N-(Aminomethyl)-5-chlorobenzyl)-1-(pyrimidine-2-carbonyl)pyrrolidine-2-carboxamide bis(2,2,2-trifluoroacetate) (260 nM) |
| 43 | 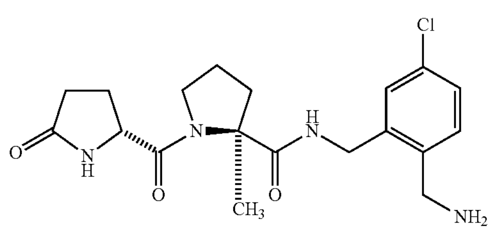 [SMILES: C[C@@]1(C(=O)NCc2cc(Cl)ccc2CN)CCCN1C(=O)[C@H]1CCC(=O)N1] | (S)-N-(2-(aminomethyl)-5-chlorobenzyl)-2-methyl-1-((R)-5-oxopyrrolidine-2-carbonyl)pyrrolidine-2-carboxamide (526 nM) |
| 44 | 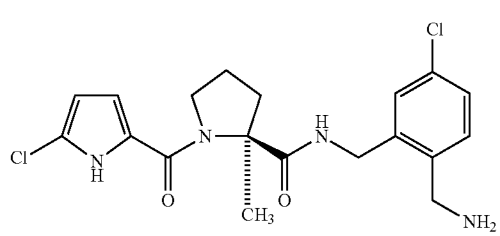 [SMILES: C[C@@]1(C(=O)NCc2cc(Cl)ccc2CN)CCCN1C(=O)c1ccc(Cl)[nH]1] | (S)-N-(2-(aminomethyl)-5-chlorobenzyl)-1-(5-chloro-1H-pyrrole-2-carbonyl)-2-methylpyrrolidine-2-carboxamide (104 nM) |

TABLE 1-continued

| Compound | Structure | Name-Ki (nM) |
|---|---|---|
| 45 | 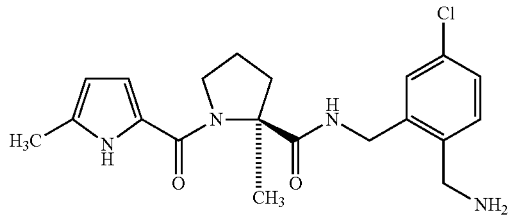 [SMILES: Cc1ccc(C(=O)N2CCC[C@@]2(C)C(=O)NCc2cc(Cl)ccc2CN)[nH]1] | (S)-N-(2-(aminomethyl)-5-chlorobenzyl)-2-methyl-1-(5-methyl-1H-pyrrole-2-carbonyl)pyrrolidine-2-carboxamide (93 nM) |

The present invention encompasses all stereoisomeric forms of the compounds of Formula I. Centers of asymmetry that are present in the compounds of Formula I can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (including hydrates) and solvated salts of such racemates, enantiomers, diastereomers and tautomers and mixtures thereof.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with un-solvated and anhydrous forms.

Reference to the compounds of this invention as those of a specific formula or embodiment, e.g., Formula I or any other generic structural formula or specific compound described or claimed herein, is intended to encompass the specific compound or compounds falling within the scope of the formula or embodiment, including salts thereof, particularly pharmaceutically acceptable salts, solvates of such compounds and solvated salt forms thereof, where such forms are possible unless specified otherwise.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I can be prepared without undue experimentation by conventional techniques well known to those skilled in the art or by processes analogous to those described in the Schemes and Examples herein using appropriate isotopically-enriched reagents and/or intermediates.

It will be understood that, as used herein, references to the compounds of structural Formula I are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfanate, edetate, edisylate, estolate, esylate, ethanesulfonate, formic, fumarate, gluceptate, glucoheptanoate, gluconate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of physiologically acceptable salts.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO⁻ depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

When any variable occurs more than one time in any constituent or in formula I, its definition on each occurrence is independent of its definition at every other occurrence. Also, combinations of substituents and/or variables are permissible only if such combinations result in stable compounds.

Some abbreviations that may appear in this application are as follows:

ABBREVIATIONS

AcOH acetic acid
Ac₂O acetic anhydride
BnBr benzyl bromide
BOC tert-butyloxycarbonyl
(BOC)₂O di-t-butyl dicarbonate
BuLi butyl lithium
CAN ceric ammonium nitrate
CBZ benzyloxycarbonyl
CBZ-Cl benzyl chloroformate
Celite® Celite® (Fluka) diatomite is diatomaceous earth
CPBA chloroperoxybenzoic acid
DBU 1,8-Diazobicyclo[5.4.0]undec-7-ene
DCC N,N'-dicyclohexylcarbodiimide
DIAD diisopropyl azodicarboxylate
DIBAL-H diisobutylaluminium hydride
DIPEA/DIEA N,N-diisopropylethylamine (Hünig's base)
DMAP dimethylaminopyridine
DMF dimethylformamide
DMP Dess-Martin Periodinane
DMSO dimethylsulfoxide
DPPA diphenylphosphoryl azide
EDC 1-ethyl-3-(3-dimethylaminopropyl)carbodiimide
EDCI 1-ethyl-3-(3-dimethylaminopropyl)carbodiimide
EtOH ethanol
EtOAc ethyl acetate
Et₃N triethylamine
Et₃SiH triethylsilane
Fmoc (FMOC) 9-fluorenylmethoxycarbonyl Fmoc-Cl 9-fluorenylmethyl chloroformate
HATU O-(7-Azabenzotriazol-1-yl)-N,N,N',N'-tetramethyluronium hexafluorophosphate
HC(OEt)$_3$ triethyl orthoformate
HOAc acetic acid
HOBt 1-hydroxybenzotriazole
LAH lithium aluminum hydride
LiHMDS lithium bis(trimethylsilyl)amide
MEM methoxyethoxymethyl
MEM-Cl methoxyethoxymethyl Chloride
MeOH methanol
MPM methoxyphenylmethyl
MPM-Cl methoxyphenylmethyl Chloride
MsCl methanesulfonyl chloride
MTBE methyl tert-butyl ether
NaBH$_3$CN sodium cyanoborohydride
NaHMDS sodium hexamethyldisilazide
NaN$_3$ sodium azide
NH$_4$OAc ammonium acetate
NMO N-Methylmorpholine-N-oxide
OAc acetoxy group
Pd/C palladium on carbon
Pd(PPh$_3$)$_4$ tetrakis(triphenylphosphine)palladium(0)
PEG polyethylene glycol
PMe$_3$ trimethylphosphane
pna p-nitroanilide
PPh$_3$ triphenylphosphane
PR Pro-Arg
PyBOP (benzotriazol-1-yloxy)tripyrrolidinophosphonium hexafluorophosphate
PyBroP bromo-tris-pyrrolidino phosphoniumhexafluorophosphate
rt room temperature
sar sarcosine
SEM-Cl (2-chloromethoxyethyl)trimethylsilane
SFC supercritical fluid
TBAF tetrabutylammonium Fluoride
TFA trifluoroacetic acid
THF tetrahydrofuran
TiCl$_4$ titanium tetrachloride
TLC thin layer chromatography
TMS tetramethylsilane
TMSCF$_3$ (trifluoromethyl)trimethylsilane
TMSCl trimethylsilyl chloride
TMSCN trimethylsilyl cyanide
TRIS tris(hydroxymethyl)aminomethane
Z-GPR-afc Z-Gly-Pro-Arg-7-amino-4-trifluoromethylcoumarin
Zn(N$_3$)$_2$ zinc azide Except where noted, the term "alkyl" refers to both branched- and straight-chain saturated aliphatic hydrocarbon groups having the specified number of carbon atoms (Me is methyl, Et is ethyl, Pr is propyl, Bu is butyl), unsubstituted or substituted with C$_{1-4}$ alkyl or halogen.

Except where noted, the term "halogen" means fluorine, chlorine, bromine or iodine.

Except where noted, the term "C$_{3-8}$ cycloalkyl" refers to cyclopropyl, cyclobutyl, cyclopentyl, cyclohexyl, cycloheptyl, and cyclooctyl, and the like, unsubstituted or substituted with C$_{1-4}$ alkyl or halogen.

Except where noted, the term "carbocycle" (and variations thereof such as "carbocyclic" or "carbocyclyl") as used herein, unless otherwise indicated, refers to a C$_3$ to C$_8$ monocyclic saturated ring. Saturated carbocyclic rings are also referred to as cycloalkyl rings, e.g., cyclopropyl, cyclobutyl, etc.

Except where noted, the term "aryl" refers to a stable 6- to 10-membered mono- or bicyclic ring system such as phenyl, or naphthyl. The aryl ring can be unsubstituted or substituted with one or more of C$_{1-4}$ alkyl, hydroxyl, alkoxy, halogen, or amino.

Except where noted, the term "heterocycle" or "heterocyclic ring" refers to a stable mono- or bicyclic heterocyclic ring system, any ring of which may be saturated or unsaturated, and which consists of carbon atoms and heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Especially useful are rings containing one oxygen or sulfur, one to four nitrogen atoms, or one oxygen or sulfur combined with one or two nitrogen atoms. The heterocyclic ring may be attached at any heteroatom or carbon atom which results in the creation of a stable structure. Examples of such heterocyclic groups include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyridyl N-oxide, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, tetrazole, thienyl, benzothienyl, thiamorpholinyl, thiamorpholinyl sulfoxide, thiamorpholinyl sulfone, and oxadiazolyl. Morpholino is the same as morpholinyl.

In this specification methyl substituents may be represented by

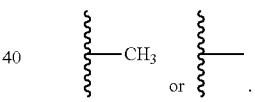

For example, the structures

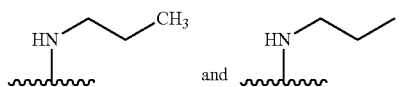

have equivalent meanings.

Thrombin Inhibitors—Therapeutic Uses—Method of Using

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice.

Thrombin inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, the thrombin inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention may be useful for treating or preventing venous thromboembolism (e.g., obstruction or occlusion of a vein by a detached thrombus; obstruction or occlusion of a lung artery by a detached thrombus), cardiogenic thromboembolism (e.g., obstruction or occlusion of the heart by a detached thrombus), arterial thrombosis (e.g., formation of a thrombus within an artery that may cause infarction of tissue supplied by the artery), atherosclerosis (e.g., arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention may be useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention may be useful for maintaining patency in arteriovenous cannulas.

Examples of atherosclerosis include arteriosclerosis.

Examples of devices that come into contact with blood include vascular grafts, stents, orthopedic prosthesis, cardiac prosthesis, and extracorporeal circulation systems The thrombin inhibitors of the invention can be administered in such oral forms as tablets, capsules (each of which includes sustained release or timed release formulations), pills, powders, granules, elixirs, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but non-toxic amount of the compound desired may be employed as an anti-aggregation agent. For treating ocular build up of fibrin, the compounds may be administered intraocularly or topically as well as orally or parenterally.

The thrombin inhibitors can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

The thrombin inhibitors can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The thrombin inhibitors may also be delivered by the use of monoclonal antibodies as individual carriers to which the compound molecules are coupled. The thrombin inhibitors may also be coupled with soluble polymers as targetable drug carriers. Such polymers can include polyvinlypyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the thrombin inhibitors may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The dosage regimen utilizing the thrombin inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the thrombin inhibitors, when used for the indicated effects, will range between about 0.01 mg per kg of body weight per day (mg/kg/day) to about 30 mg/kg/day, preferably 0.025-7.5 mg/kg/day, more preferably 0.1-2.5 mg/kg/day, and most preferably 0.1-0.5 mg/kg/day (unless specified otherwise, amounts of active ingredients are on free base basis). For example, an 80 kg patient would receive between about 0.8 mg/day and 2.4 g/day, preferably 2-600 mg/day, more preferably 8-200 mg/day, and most preferably 8-40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the thrombin inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025-7.5 mg/kg/day, preferably 0.1-2.5 mg/kg/day, and more preferably 0.1-0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01-1.0 mg/ml, e.g. 0.1 mg/ml, 0.3 mg/ml, and 0.6 mg/ml, and administered in amounts per day of between 0.01 ml/kg patient weight and 10.0 ml/kg patient weight, e.g. 0.1 ml/kg, 0.2 ml/kg, 0.5 ml/kg. In one example, an 80 kg patient, receiving 8 ml twice a day of an intravenous formulation having a concentration of active ingredient of 0.5 mg/ml, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. The choice of appropriate buffer and pH of a formulation, depending on solubility of the drug to be administered, is readily made by a person having ordinary skill in the art.

The compounds can also be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

The thrombin inhibitors are typically administered as active ingredients in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, distintegrating agents and coloring agents can also be incorporated into the mixture. Suitable binders include starch, gelatin, natural sugars such as glucose or beta-lactose, corn-sweeteners, natural and synthetic gums such as *acacia*, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

The thrombin inhibitors can also be co-administered with suitable anticoagulants, including, but not limited to, other thrombin inhibitors, thrombin receptor antagonists, factor VIIa inhibitors, factor IXa inhibitors, factor Xa inhibitors, factor XIa inhibitors, adenosine diphosphate antiplatelet agents (e.g., P2Y12 antagonists), fibrinogen receptor antagonists (e.g. to treat or prevent unstable angina or to prevent reocclusion after angioplasty and restenosis), other anticoagulants such as aspirin, and thrombolytic agents such as plasminogen activators or streptokinase to achieve synergistic effects in the treatment of various vascular pathologies. Such anticoagulants include, for example, apixaban, dabigatran, cangrelor, ticagrelor, vorapaxar, clopidogrel, edoxaban, mipomersen, prasugrel, rivaroxaban, and semuloparin. For example, patients suffering from coronary artery disease, and patients subjected to angioplasty procedures, would benefit from coadministration of fibrinogen receptor antagonists and thrombin inhibitors. Also, thrombin inhibitors enhance the efficiency of tissue plasminogen activator-mediated thrombolytic reperfusion. Thrombin inhibitors may be administered first following thrombus formation, and tissue plasminogen activator or other plasminogen activator is administered thereafter.

Alternatively or additionally, one or more additional pharmacologically active agents may be administered in combination with a compound of the invention. The additional active agent (or agents) is intended to mean a pharmaceutically active agent (or agents) that is active in the body, including pro-drugs that convert to pharmaceutically active form after administration, which is different from the compound of the invention, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of the invention in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); angiotensin II receptor antagonists also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®), etc.); potassium sparing diuretics such as amiloride HCl, spironolactone, eplerance, triamterene, each with or without HCTZ; neutral endopeptidase inhibitors (e.g., thiorphan and phosphoramidon); aldosterone antagonists; aldosterone synthase inhibitors; renin inhibitors; enalkrein; RO 42-5892; A 65317; CP 80794; ES 1005; ES 8891; SQ 34017; aliskiren (2(S),4(S),5(S),7(S)-N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant (TREDAPTIVE®) and/or with an HMG-CoA reductase inhibitor; niacin in immediate-release or controlled release forms, and particularly niacin in combination with a DP antagonist such as laropiprant (TREDAPTIVE®) and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; or with other drugs beneficial for the prevention or the treatment of the above-mentioned diseases including but not limited to diazoxide; and including the free-acid, free-base, and pharmaceutically acceptable salt forms, pro-drug forms, e.g., esters, and salts of pro-drugs of the above medicinal agents, where chemically possible. Trademark names of pharmaceutical drugs noted above are provided for exemplification of the marketed form of the active agent(s); such pharmaceutical drugs could be used in a separate dosage form for concurrent or sequential administration with a compound of the invention, or the active agent(s) therein could be used in a fixed dose drug combination including a compound of the invention.

Typical doses of thrombin inhibitors of the invention in combination with other suitable anti-platelet agents, anticoagulation agents, or thrombolytic agents may be the same as those doses of thrombin inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

INTERMEDIATE COMPOUND PREPARATION

Intermediate compounds used to prepare compounds of the invention can be prepared according to Scheme 1.

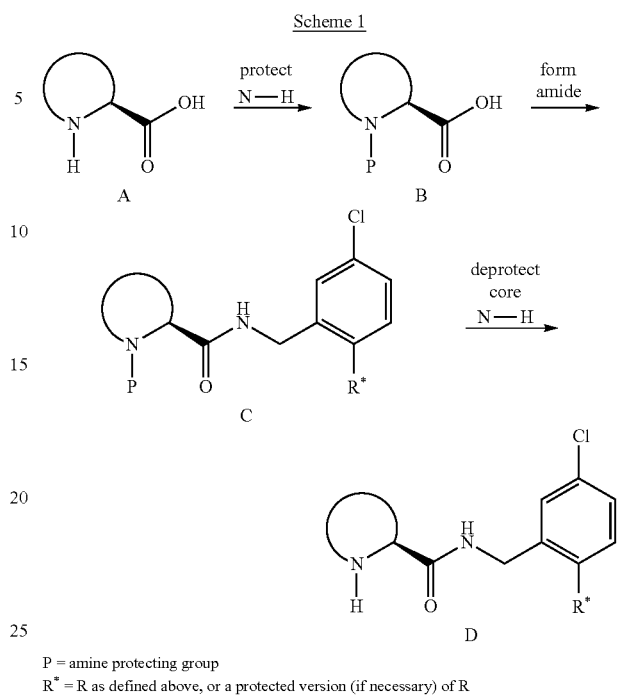

P = amine protecting group
R* = R as defined above, or a protected version (if necessary) of R Intermediate compounds described in Scheme 1 can be prepared by methods known to those skilled in the art. The synthesis generally begins with the core amino-acid A. The N-H group is protected using a standard amine protecting group such as BOC, FMOC, CBZ, and the like by reacting the amine with the appropriate protecting reagent such as (BOC)$_2$O, FMOC-Cl, CBZ-Cl, and the like at a temperature of 0-35° C. in an appropriate solvent such as THF, dioxane, ether, dichloromethane, and the like, with or without added base such as NaHCO$_3$, Et$_3$N, and the like for a period of 1-24 hours. In cases where the core contains an additional amino group, the second amine is protected with an orthogonal protecting group such as BOC, FMOC, CBZ, and the like using standard techniques known to those skilled in the art. Upon completion, the reaction mixture is diluted with water, acidified by addition of a strong acid such as hydrochloric acid, sulfuric acid, and the like, and extracted with an organic solvent such as ethyl acetate, ether, and the like. The product is isolated by evaporation of the solvent and may be purified by chromatography or used "as is" in the next step.

The second step of the synthesis involves coupling the core acid with an amine side chain to form an amide bond. This can be accomplished using standard amide bond-forming techniques well-known to those skilled in the art. The core acid and the side chain amine are dissolved or suspended in a suitable solvent such as DMF, THF, dichloromethane, and the like then a coupling agent such as EDC, DCC, PyBOP and the like is added and the reaction is allowed to proceed, with or without an additive such as HOBT, DMAP, and the like at a temperature of 0-35° C. for 1-24 hours. Upon completion, the reaction mixture is diluted with water, washed with a basic aqueous solution such as aqueous sodium bicarbonate, aqueous potassium carbonate, and the like and extracted with an organic solvent such as ethyl acetate, ether, and the like. The product is isolated by evaporation of the solvent and may be purified by chromatography or used "as is" in the next step.

The third step involves removal of the amine protecting group installed in step one using standard methods well-known to those skilled in the art. The fluorenylmethoxycarbonyl (FMOC) group, for example, is removed by dissolving the product of step two in an appropriate solvent such as dichloromethane, ether, and the like and adding an organic amine base such as piperidine, morpholine, and the like. The reaction mixture is stirred at a temperature of 0-35° C. for 1-24 hours then concentrated under vacuum. The residue is purified by silica gel chromatography or HPLC to afford the desired intermediate.

Intermediate compounds used to prepare compounds of the invention can be prepared according to Scheme 2.

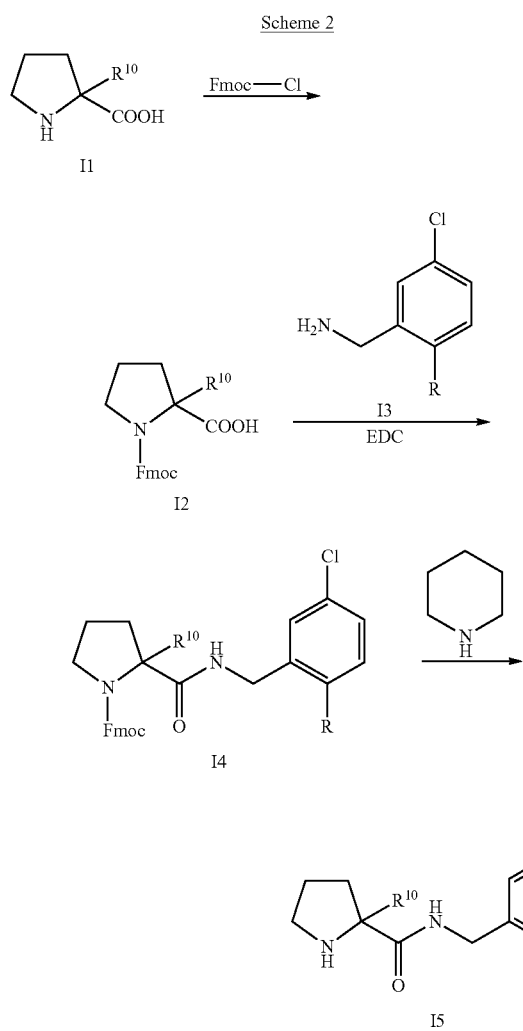

Intermediate I2, prepared from either optically pure 2-alkyl proline or racemic 2-alkyl proline (I1) via protection of the secondary amino group under standard conditions, is coupled to intermediate I3 in the presence of a peptide coupling reagent such as EDC in a solvent such as DMF to form intermediate I4. The Fmoc group is removed with a base such as piperidine to form intermediate I5.

Intermediate compound tert-Butyl 2-(aminomethyl)-4-chlorobenzylcarbamate (Intermediate 3a, where R is —CH$_2$NHBoc) can be prepared according to Scheme 3.

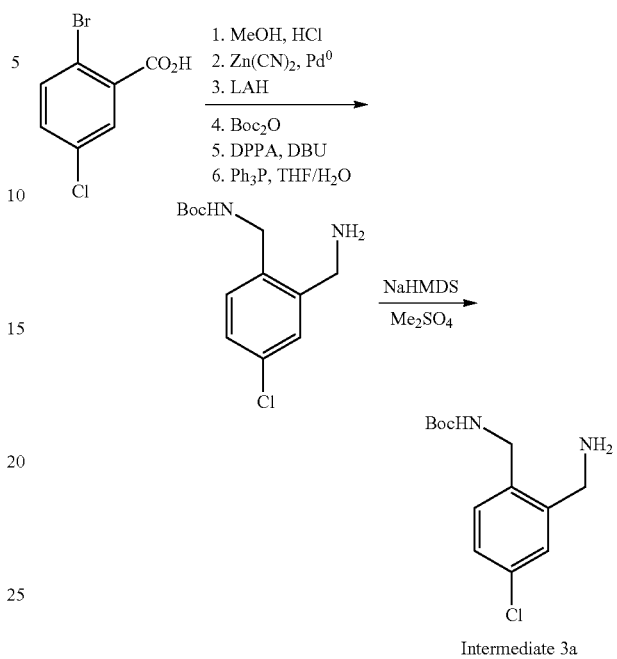

Step A: Preparation of 2-bromo-5-chlorobenzoate

Through a solution of 2-bromo-5-chlorobenzoic acid (11 g, 46.7 mmol) in methanol (250 ml) was bubbled HCl gas. The reaction was allowed to warm to room temperature and stirred overnight. The reaction mixture is concentrated in vacuo to give an orange oil, which is purified by flash chromatography (silica gel, hexane) to give the title compound as a colorless oil.

1H NMR (CDCl$_3$, 400 MHz): δ 7.78 (d, 1H, J=2.6 Hz); 7.59 (d, 1 H, J=12.81 Hz); 7.30 (dd, 1 H, J=8.6, 2.5 Hz); 3.94 (s, 3H)

Step B: Preparation of Methyl 5-chloro-2-cyanobenzoate

To a solution of methyl 2-bromo-5-chlorobenzoate (1.15 g, 4.6 mmol) in degassed DMF was added zinc cyanide (282 mg, 2.40 mmol) and palladium tetrakis triphenylphosphine (100 mg, 0.086 mmol) and the reaction is stirred at 90° C. over night. The reaction was partitioned between ethyl acetate and water. The organic was concentrated in vacuo and purified by flash chromatography eluting a gradient to 10 to 25% ethyl acetate in hexane yielding a white solid (methyl 5-chloro-2-cyanobenzoate.

H NMR (CDCl$_3$, 400 MHz): δ 8.13 (d, 1 H, J=1.83 Hz); 3.09 (d, 1 H, J=8.24 Hz); 7.29 (dd, 1 H, J=8.34, 2.10 Hz); 4.02 (s, 3 H)

Step C: Preparation of 2-(aminomethyl)-5-chlorophenyl]methanol

To LAH (1 M/Et$_2$O, 104.4 ml, 104.4 mmol) in anhydrous THF (300 ml) at 0 C was added methyl 5-chloro-2-cyanobenzoate (9.28 g, 0.512 mmol) maintaining the temperature below 20° C. After one half hour, quenched at 0° C. with water (3.97 ml), NaOH (1N, 11.9 ml, 11.9 mmol) and water (3.97 ml). A precipitate was filtered out and washed with THF. The filtrate was concentrated in vacuo and was used immediately in the next step.

H NMR (CDCl₃, 400 MHz): δ 7.17-7.36 (m, 3 H); 4.60 (s, 2 H); 3.98 (s, 2 H);

Step D: Preparation of tert-butyl 4-chloro-2-(hydroxymethyl)benzylcarbamate

To a solution of [2-(aminomethyl)-5-chlorophenyl]methanol in dichloromethane (200 ml), was added di-tert-butyldicarbonate (11.38 g, 52.18 mmol) at room temperature. After one hour, the reaction was partitioned. The organic layer was concentrated in vacuo and purified by flash chromatography eluting a gradient of ethyl acetate/hexane which gave a brown oil, which was taken up in dichloromethane (500 ml) and treated with activated charcoal yielding a pink solid.

H NMR (CDCl₃, 400 MHz): δ 7.36 (s, 1 H); 7.2-7.5 (m, 2 H); 4.69 (b s, 2 H); 4.32 (d, 2 H, J=6.04 Hz); 1.43 (s, 9 H).

Step E: Preparation of tert-Butyl 2-(azidomethyl)-4-chlorobenzylcarbamate

To a solution of tert-butyl 4-chloro-2-(hydroxymethyl) benzylcarbamate (10 g, 36.8 mmol) in anhydrous THF (100 ml) was added DPPA (8.3 ml, 38.6 mmol) and DBU (5.79 ml, 38.6 mmol). The mixture was stirred overnight and then was partitioned between ethyl acetate and water. The organic layer was washed with brine, and was concentrated in vacuo to a crude oil (14.6 g). Purification was accomplished by silica gel chromatography, eluting a gradient of ethyl acetate-hexane (10, 15, 20, 25, 50%) to give tert-butyl 2-(aminomethyl)-4-chlorobenzylcarbamate.

H NMR (CDCl₃, 400 MHz): δ 7.25-7.39 (m, 3 H); 4.41 (s, 2 H), 4.32 (d, 2 H, J=5.86 Hz); 1.45 (s, 9 H).

Step F: Preparation of tert-Butyl 2-(aminomethyl)-4-chlorobenzylcarbamate

To a solution of tert-butyl 2-(azidomethyl)-4-chlorobenzylcarbamate (10.9 g, 36.73 mmol) in THF (60 ml) and water (6 ml) was added triphenylphospine (10.59 g, 40.40 mmol). The reaction was heated to 65° C. and stirred overnight at room temperature. The reaction was concentrated in vacuo and flashed with 4% (10% NH₄OH/MeOH)/ dichloromethane. A second purification using silica gel column chromatography with a careful gradient of 3 to 5% (10% NH₄OH/MeOH)/dichloro methane gave the title compound.

H NMR (CDCl₃, 400 MHz) δ 7.21-7.52 (m, 3 H); 4.32 (b d, 2 H); 3.90 (s, 2 H); 1.44 (s, 9 H).

Intermediate compounds used to prepare compounds of the invention where W is a 9- or 10-membered heterocycle can be prepared according to the procedure outlined in Scheme 4.

Scheme 4

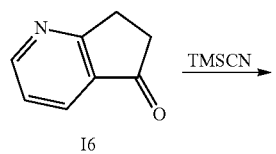

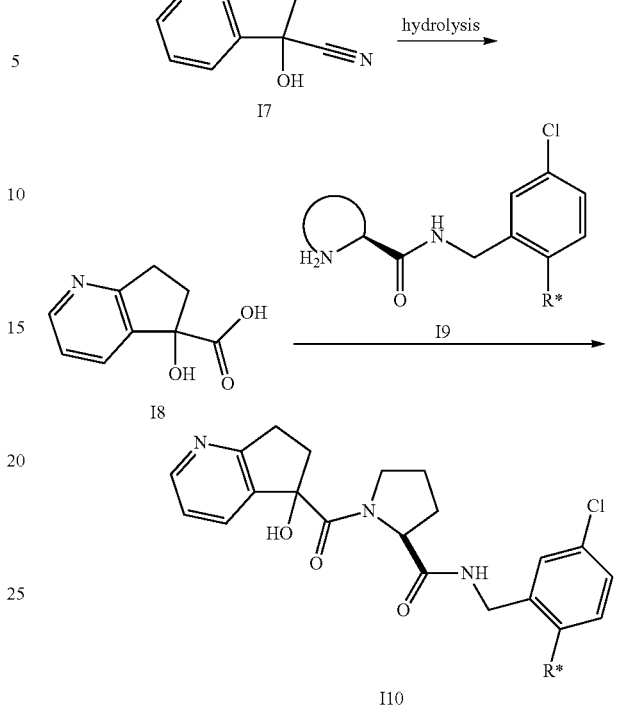

R*=R as defined above, or a protected version (if necessary) of R.

Intermediate compounds described in Scheme 4 can be prepared by methods known to those skilled in the art. The synthesis generally begins with the core cyclopentanone I6. The cyclopentanone is treated with TMSCN giving rise to the corresponding cyanohydrin I7. The cyanohydrin can be hydrolyzed either by strongly acidic or basic conditions giving rise to the α-hydroxyacid I8. The acid I8 is then reacted with amine I9 with at a temperature of 0-35° C. in an appropriate solvent such as THF, dioxane, ether, dichloromethane, and the like, with or without added base such as NaHCO₃, Et₃N, and the like for a period of 1-24 hours. In cases where the core contains an additional amino group, the second amine is protected with an orthogonal protecting group such as BOC, FMOC, CBZ, and the like using standard techniques known to those skilled in the art. Upon completion, the reaction mixture is diluted with water, acidified by addition of a strong acid such as hydrochloric acid, sulfuric acid, and the like, and extracted with an organic solvent such as ethyl acetate, ether, and the like. The product is isolated by evaporation of the solvent and may be purified by chromatography or used "as is" in the next step.

General Procedures and Conditions

NMR determinations were made using 400 MHz field strength. Ki data was obtained according to the procedure described in Lewis, et al. Thromb. Res. 1993, 70, 173 (assays of human α-thrombin and human trypsin), and Lewis, et al. Thromb. Haemostasis 1995, 74, 1107-1112. Reactions sensitive to moisture or air were performed under nitrogen or argon using anhydrous solvents and reagents. The progress of reactions was determined by either analytical thin layer chromatography (TLC) usually performed with E. Merck precoated TLC plates, silica gel 60E-254, layer thickness 0.25 mm or liquid chromatography-mass spectrometry (LC-MS). Typically, the analytical LC-MS system used consisted of a Waters ZQ platform with electrospray ionization in positive ion detection mode with an Agilent 1100 series HPLC with autosampler. The column was usually a Water Xterra MS C18, 3.0×50 mm, 5 μm. The flow rate was 1 mL/min, and the injection volume was 10 μL. UV detection was in the range 210-400 nm. The mobile phase consisted of solvent A (water plus 0.06% TFA) and solvent B (acetonitrile plus 0.05% TFA) with a gradient of 100% solvent A for 0.7 min changing to 100% solvent B over 3.75 min, maintained for 1.1 min, then reverting to 100% solvent A over 0.2 min. Preparative HPLC purifications were usually performed using a mass spectrometry directed system. Usually they were performed on a Waters Chromatography Workstation configured with LC-MS System Consisting of: Waters ZQ single quad MS system with Electrospray Ionization, Waters 2525 Gradient Pump, Waters 2767 Injector/Collector, Waters 996 PDA Detetor, the MS Conditions of: 150-750 amu, Positive Electrospray, Collection Triggered by MS, and a Waters Sunfire C-18 5 micron, 30 mm (id)×100 mm column. The mobile phases consisted of mixtures of acetonitrile (10-100%) in water containing 0.1% TFA. Flow rates were maintained at 50 mL/min, the injection volume was 1800 μL, and the UV detection range was 210-400 nm. Mobile phase gradients were optimized for the individual compounds. Reactions performed using microwave irradiation were normally carried out using an Emrys Optimizer manufactured by Personal Chemistry, or an Initiator manufactured by Biotage. Concentration of solutions was carried out on a rotary evaporator under reduced pressure. Flash chromatography was usually performed using a Biotage Flash Chromatography apparatus (Dyax Corp.) on silica gel (32-63 mM, 60 Å pore size) in pre-packed cartridges of the size noted. $^1$H NMR spectra were acquired at 500 MHz spectrometers in CDCl$_3$ solutions unless otherwise noted. Chemical shifts were reported in parts per million (ppm). Tetramethylsilane (TMS) was used as internal reference in CD$_3$Cl solutions, and residual CH$_3$OH peak or TMS was used as internal reference in CD$_3$OD solutions. Coupling constants (J) were reported in hertz (Hz). Chiral analytical chromatography was performed on one of Chiralpak AS, Chiralpak AD, Chiralcel OD, Chiralcel IA, or Chiralcel OJ columns (250× 4.6 mm) (Daicel Chemical Industries, Ltd.) with noted percentage of either ethanol in hexane (% Et/Hex) or isopropanol in heptane (% IPA/Hep) as isocratic solvent systems. Chiral preparative chromatography was conducted on one of Chiralpak AS, Chiralpak AD, Chiralcel OD, Ciralcel IA, or Chiralcel OJ columns (20×250 mm) (Daicel Chemical Industries, Ltd.) with desired isocratic solvent systems identified on chiral analytical chromatography or by supercritical fluid (SFC) conditions. Celite® (Fluka) diatomite is diatomaceous earth, and can be referred to as "celite".

EXAMPLE 1

Preparation of (S)—N-[2-(Aminomethyl)-5-chlorobenzyl]-1-[(R)-2-(2-hydroxyethyl)-3,3-dimethylbutanoyl]pyrrolidine-2-carboxamide-2,2,2-trifluoroacetate (1-12)

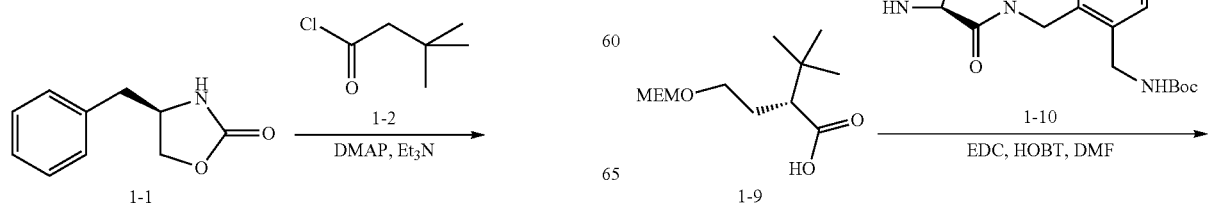

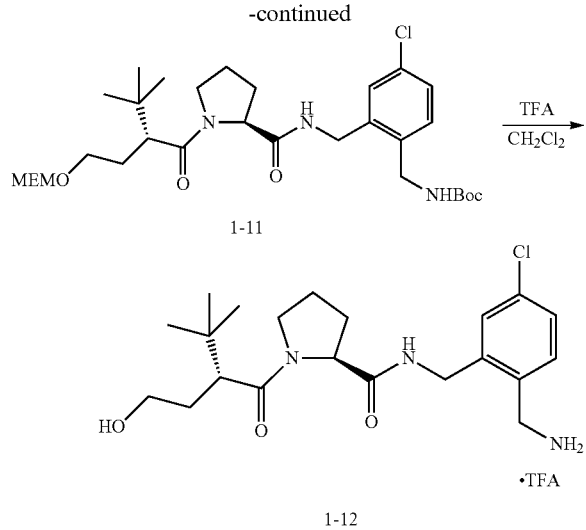

(R)-4-Benzyl-3-(3,3-dimethylbutanoyl)oxazolidin-2-one (1-3)

A solution of tert-butylacetyl chloride 1-2 (8.6 mL, 62.1 mmol) in anhydrous THF (50 mL) was added dropwise to the mixture of (R)-4-benzyloxazolidin-2-one 1-1 (10.0 g, 56.4 mmol), $Et_3N$ (17.4 mL, 124 mmol) and DMAP (0.86 g, 7.04 mmol) in anhydrous THF (100 mL) at 0° C., and the reaction mixture was stirred at the same temperature for 3 h. Water (200 mL) was added to quench the reaction, and the mixture was extracted with EtOAc (2×200 mL). The organic layer was washed with brine (200 mL), dried over anhydrous $Na_2SO_4$, filtered, and concentrated under reduced pressure. The residue was purified by combiflash (silica gel; 40-70% $CH_2Cl_2$/hexanes) to provide acylated intermediate 1-3.

(R)-tert-Butyl-3-[(R)-4-benzyl-2-oxooxazolidine-3-carbonyl]-4,4-dimethylpentanoate (1-5)

A solution of sodium hexamethyldisilazide (1M in THF, 17.9 mL, 17.9 mmol) was added dropwise to a stirred solution of imide intermediate 1-3 (4.50 g, 16.3 mmol) in THF (60 mL) at −78° C., and reaction mixture was stirred at −78° C. for 3.5 h. A solution of tert-butyl bromo acetate 1-4 (7.2 mL, 49.0 mmol) in THF (20 mL) was added dropwise to the said mixture and mixture was again stirred at −78° C. for 18 h. The reaction mixture was quenched by $NH_4Cl$ (sat. aq., 30 mL) and warmed to room temperature. The reaction mixture was diluted with water and extracted with MTBE (2×100 mL). The combined organic layers were washed with brine solution (100 mL), dried over anhydrous $Na_2SO_4$, filtered, and concentrated under reduced pressure. The residue was purified by combiflash (silica gel; eluent: 20-30% EtOAc/hexanes) to provide alkylated intermediate 1-5.

(R)-3-[(R)-4-Benzyl-2-oxooxazolidine-3-carbonyl]-4,4-dimethylpentanoic acid (1-6)

TFA (5 mL, 65.3 mmol) was added to the solution of tert-butyl ester intermediate 1-5 (3.3 g, 8.48 mmol) in $CH_2Cl_2$ (20 mL), and the reaction mixture was stirred at room temperature for 5 h. The solvent was removed under reduced pressure and the residue was azeotroped with toluene (2 ×20 mL) and dried over high vacuum pump for 2 h to provide acid 1-6.

(R)-4-Benzyl-3-[(R)-2-(2-hydroxyethyl)-3,3-dimethylbutanoyl]oxazolidin-2-one (1-7)

The 2.0 M solution of $BH_3 \cdot Me_2S$ in THF (19.1 mL, 57.3 mmol) was added dropwise to the solution of acid 1-6 (2.8 g, 8.40 mmol) in THF (20 mL), and the reaction mixture was stirred at room temperature for 5 h. The reaction was quenched by slow addition of MeOH (30 mL) at 0° C. and mixture was stirred at room temperature for 30 min. The solvent was removed under reduced pressure and residue was purified by combiflash (silica gel; eluent: 50-60% EtOAc/hexanes) to provide alcohol intermediate 1-7.

(R)-4-Benzyl-3-{(R)-2-[2-{(2-methoxyethoxy)methoxy}ethyl]-3,3-dimethylbutanoyl}oxazolidin-2-one (1-8)

MEM-Cl (0.71 mL, 6.2 mmol) and DIPEA (0.63 mL, 3.41 mmol) were added to the solution of alcohol 1-7 (1.0 g, 3.1 mmol) in THF (20 mL), and the reaction mixture was stirred at 50° C. for 16 h. The reaction was quenched by water (20 mL) and extracted with EtOAc (2×25 mL). The combined organic extract was washed with brine solution (25 mL), water (25 mL), dried over anhydrous $Na_2SO_4$, filtered and concentrated under reduced pressure. The residue was purified by combiflash (silica gel; eluent: 25-30% EtOAc/hexanes) to provide protected alcohol 1-8.

(R)-2-[2-{(2-Methoxyethoxy)methoxy}ethyl]-3,3-dimethylbutanoic acid (1-9)

The solution of LiOH (0.51 g, 15 mmol) in water (2 mL) was added dropwise to the solution of alcohol intermediate 1-8 (1.35 g, 3 mmol) in THF (15 mL) and $H_2O_2$ (257 mg, 6 mmol; 30% solution) at 0° C. and reaction mixture was stirred at room temperature for 3 days. The solvent was removed under reduced pressure and mixture was diluted with water (20 mL), and extracted with EtOAc (5×30 mL). The combined organic extract was washed with brine solution (25 mL), dried over anhydrous $Na_2SO_4$, filtered and concentrated under reduced pressure. The residue was purified by reverse phase combiflash (C18; eluent: 40-50% acetonitrile/water) to provide protected acid 1-9.

tert-Butyl-4-chloro-2-[{(S)-1-{(R)-2-[2-{(2-methoxyethoxy)methoxy}ethyl]-3,3-dimethylbutanoyl)pyrrolidine-2-carboxamido}methyl]benzylcarbamate (1-11)

The mixture of acid 1-9 (0.10 g, 0.40 mmol), amine 1-10 (0.148 g, 0.40 mmol), EDC (0.084 g, 0.44 mmol) and HOBt (0.059 g, 0.44 mmol) in DMF (5 mL) was stirred at room temperature for 16 h. The reaction was quenched with water (10 mL) and extracted with EtOAc (3×20 mL). The combined organic extract was washed with brine solution (20 mL), water (20 mL), dried over anhydrous $Na_2SO_4$, filtered and concentrated under reduced pressure. The residue was purified by reverse phase combiflash (C18; eluent: 60-70% acetonitrile/water) to provide 1-11.

(S)—N-{2-(Aminomethyl)-5-chlorobenzyl}-1-{(R)-2-(2-hydroxyethyl)-3,3-dimethylbutanoyl}pyrrolidine-2-carboxamide (1-12)

The 50% solution of TFA (6 mL) in $CH_2Cl_2$ was added to the solution of 1-11 (0.075 g, 0.13 mmol) in $CH_2Cl_2$ (1 mL)

and reaction mixture was stirred at room temperature for 2 h. The solvent was removed under reduced pressure and residue was azeotroped with toluene (2×5 mL) and crude product was purified by reverse phase combiflash (C18; eluent: 30-35% acetonitrile/water) to provide 1-12. ¹H NMR (MeOD-d₄, 400 MH$_z$) (δ) ppm: 7.47 (d, J=1.6 Hz, 1H), 7.42-7.36 (m, 2H), 4.46-4.31 (m, 3H), 4.27-4.19 (m, 2H), 3.86-3.80 (m, 1H), 3.71-3.67 (m, 1H), 3.59-3.50 (m, 2H), 2.62 (dd, J=2.8 Hz, J=10.8 Hz, 1H), 2.20-2.15 (m, 1H), 1.98-1.92 (m, 3H), 1.88-1.68 (m, 2H), 0.98 (s, 9H).

EXAMPLE 2

Preparation of (S)—N-[2-(Aminomethyl)-5-chlorobenzyl]-1-[4-(trifluoromethyl)-1H-pyrrole-2-carbonyl]pyrrolidine-2-carboxamide-2,2,2-trifluoroacetate (2-11)

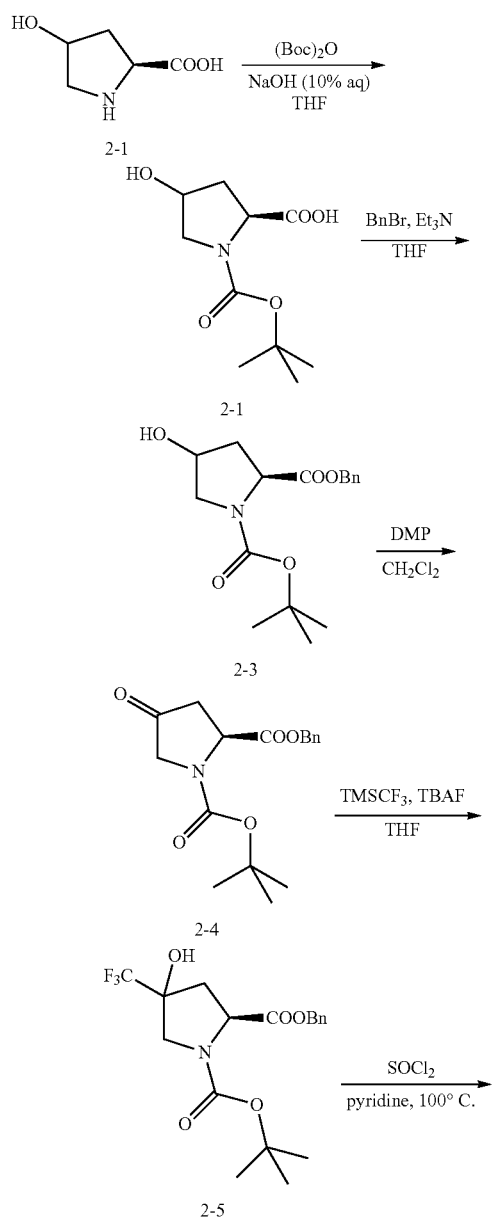

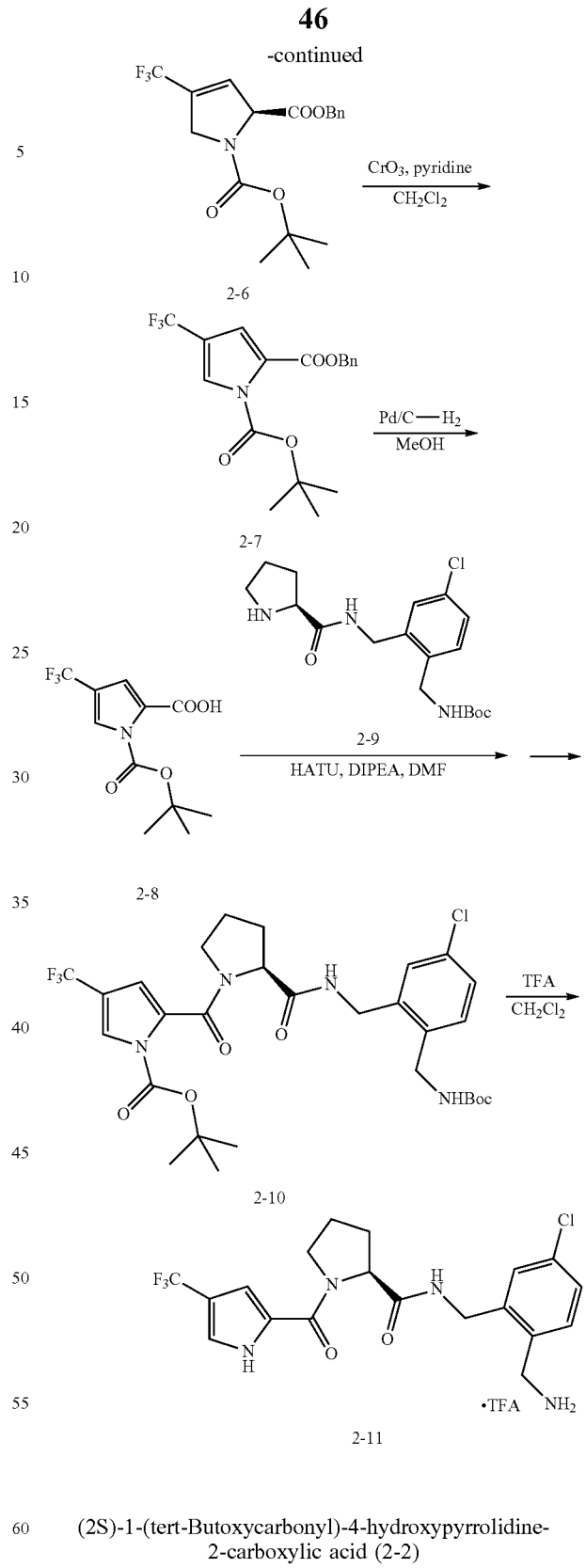

(2S)-1-(tert-Butoxycarbonyl)-4-hydroxypyrrolidine-2-carboxylic acid (2-2)

A solution of di-tert-butyldicarbonate (29.9 g, 137.4 mmol) in THF (30 mL) was added to the mixture of trans-4-hydroxy-L-proline 2-1 (15.0 g, 114.5 mmol) and 10% aqueous NaOH (10 g, 252 mmol) in THF (100 mL) and reaction mixture was stirred at room temperature for 16 h.

Organic solvent was removed at reduced pressure and mixture was diluted with water (200 mL). The aqueous layer was washed with MTBE (200 mL), acidified to pH 2 with 10% aqueous KHSO$_4$, and extracted with EtOAc (3×200 mL). The combined organic layers were washed with brine solution (200 mL), water (200 mL), dried over anhydrous Na$_2$SO$_4$, filtered and concentrated under reduced pressure to provide Boc protected proline 2-2.

(2S)-2-Benzyl-1-tert-butyl-4-hydroxypyrrolidine-1,2-dicarboxylate (2-3)

Benzyl bromide (16.0 mL, 135 mmol) was added dropwise to the mixture of Boc proline intermediate 2-2 (24.0 g, 104 mmol) and Et$_3$N (18.1 mL, 135 mmol) in THF (500 mL) at 0° C. and reaction mixture was stirred at same temperature for 30 min and then at room temperature for 16 h. The solvent was removed at reduced pressure and residue was dissolved in EtOAc and washed with 1N HCl (300 mL), water (300 mL), aqueous saturated NaHCO$_3$ solution (300 mL) and water (300 mL). The organic layer dried over anhydrous Na$_2$SO$_4$, filtered and concentrated under reduced pressure. The oil was purified by column chromatography (silica gel; eluent: 25-30% EtOAc/hexanes) to provide benzyl ester intermediate 2-3.

(S)-2-Benzyl 1-tert-butyl 4-oxopyrrolidine-1,2-dicarboxylate (2-4)

Dess-Martin periodinane (55.4 g, 130 mmol) was added in portions to the solution of hydroxyl proline intermediate 2-3 (21.0 g, 65.4 mmol) in CH$_2$Cl$_2$ (200 mL) at 0° C. The mixture was warmed to room temperature and stirred at same temperature for 3 h. The reaction mixture was diluted with CH$_2$Cl$_2$ (200 mL), washed with 1:1 mixture of saturated aqueous NaHCO$_3$ (200 mL) solution and saturated aqueous Na$_2$S$_2$O$_3$ (200 mL) solution. The organic layer was dried over anhydrous Na$_2$SO$_4$, filtered and concentrated under reduced pressure to provide ketone 2-4.

(2S)-2-Benzyl 1-tert-butyl 4-hydroxy-4-(trifluoromethyl)pyrrolidine-1,2-dicarboxylate (2-5)

(Trifluoromethyl)trimethylsilane (2.0 mL, 13.7 mmol) and TBAF (0.5 mL, cat) was added dropwise to the solution of ketone intermediate 2-4 (4.0 g, 12.5 mmol) in THF (60 mL) at 0° C. and reaction mixture was stirred at room temperature for 20 h. The reaction was quenched with saturated aqueous NH$_4$Cl$_4$ solution (50 mL) and stirred for 15 min. TBAF (20 mL, 1.0 M in THF) was added and reaction mixture was stirred at room temperature for 1.5 h. The organic layer was separated and aqueous layer was extracted with MTBE (3×100 mL). The combined organic extract was washed with brine solution (200 mL), water (200 mL), dried over anhydrous Na$_2$SO$_4$, filtered and concentrated under reduced pressure. The residue was purified by combiflash (silica gel; eluent: 20% EtOAc/hexanes) to provide the hydroxyl trifluoromethyl proline intermediate 2-5.

(S)-2-Benzyl-1-tert-butyl 4-(trifluoromethyl)-1H-pyrrole-1,2(2H, 5H)-dicarboxylate (2-6)

A mixture of hydroxyl trifluoromethyl proline intermediate 2-5 (1.9 g, 4.88 mmol), SOCl$_2$ (5 mL, 68.8 mmol) in anhydrous pyridine (65 mL) was stirred at 90° C. for 1 h. The reaction was cooled to room temperature and quenched with water (50 mL) and extracted with MTBE (2×100 mL). The combined organic extract was washed with 1M HCl (50 mL), saturated NaHCO$_3$ solution (50 mL), water (50 mL), and brine solution (50 mL). The organic layer was dried over anhydrous Na$_2$SO$_4$, filtered and concentrated under reduced pressure. The residue was purified by combiflash (silica gel; 20% EtOAc/hexanes) to obtain intermediate 2-6.

2-Benzyl-1-tert-butyl-4-(trifluoromethyl)-1H-pyrrole-1,2-dicarboxylate (2-7)

A solid CrO$_3$ (1.65 g, 16.5 mmol) was added in portions to the mixture of the pyridine (3.5 mL) and CH$_2$Cl$_2$ (10 mL) at 0° C. and mixture was stirred at same temperature for 20 min. A solution of dihydropyrrole intermediate 2-6 (0.30 g, 0.80 mmol) in CH$_2$Cl$_2$ (3 mL) was added and mixture was warmed to room temperature followed by stirring at 90° C. for 2 h. The solvent was removed under reduced pressure and residue was washed with MTBE (4×20 mL). The combined organic extract was washed with 1M HCl (20 mL), saturated aqueous NaHCO$_3$ (20 mL), water (30 mL) and dried over anhydrous Na$_2$SO$_4$, filtered and concentrated. The residue was purified by combiflash (silica gel; eluent: 20% EtOAc/hexanes) to provide pyrrole 2-7.

1-(tert-Butoxycarbonyl)-4-(trifluoromethyl)-1H-pyrrole-2-carboxylic acid (2-8)

Pd/C (0.044 g, 20% by wt) was added to the solution of the benzyl ester intermediate 2-7 (0.22 g, 0.59 mmol) in EtOAc (20 mL) and reaction mixture was stirred under H$_2$ atmosphere (1 atm) at room temperature for 16 h. The mixture was diluted with EtOAc (25 mL) and filtered over pad of celite. The filerate was dried over anhydrous Na$_2$SO$_4$, filtered and concentrated under educed pressure to provide acid 2-8.

(S)-tert-Butyl 2-(2-{(2-[{(tert-butoxycarbonyl)amino}methyl]-5-chlorobenzyl)carbamoyl}pyrrolidine-1-carbonyl)-4-(trifluoromethyl)-1H-pyrrole-1-carboxylate (2-10)

The mixture of acid 2-8 (110 mg, 0.39 mmol), amine 2-9 (0.144 g, 0.39 mmol), HATU (0.448 g, 1.18 mmol) and DIPEA (0.41 mL, 2.36 mmol) in DMF (5 mL) was stirred at room temperature for 4 h. The reaction was quenched with water (20 mL) and extracted with EtOAc (3×20 mL). The combined organic extract was dried over anhydrous Na$_2$SO$_4$, filtered, and concentrated under reduced pressure. The residue was purified by reverse phase combiflash (C18, eluent: 60-70 acetonitrile/water) to provide 2-10.

(S)—N-{2-(Aminomethyl)-5-chlorobenzyl}-1-{4-(trifluoromethyl)-1H-pyrrole-2-carbonyl}pyrrolidine-2-carboxamide-2,2,2-trifluoroacetate (2-11)

A 50% solution of TFA (5 mL) in CH$_2$Cl$_2$ was added to the solution of 2-10 (0.10 g, 0.16 mmol) in CH$_2$Cl$_2$ (1 mL) and mixture was stirred at room temperature for 3 h. The solvent was removed under reduced pressure, the residue was azeotroped with toluene (2×20 mL) and dried over high vacuum pump. The crude product was purified by reverse phase combiflash (C18; 20-30% acetonitrile/water) to obtain 2-11 as white solid. $^1$H NMR (CD$_3$CN, 400 MHz) (δ) ppm: 11.06 (brs, 1H), 7.91-7.82 (m, 4H), 7.36 (d, J=8 Hz, 1H), 7.27 (dd, J=2 Hz, J=23 Hz, 2H), 7.23 (s, 2H), 6.84 (s, 1H), 4.32 (dd, J=6 Hz, J=16.8 Hz, 1H), 4.30 (quat, J=4.8 Hz, 1H), 4.18 (dd, J=5.2 Hz, J=14.6 Hz, 1H), 4.10 (s, 2H), 3.79-3.72 (m, 2H), 2.08-1.90 (m, 3H).

EXAMPLE 3

Preparation of (S)-Ethyl-5-[2-{(2-(aminomethyl)-5-chlorobenzyl)carbamoyl}-pyrrolidine-1-carbonyl]-1H-pyrrole-2-carboxylate-2,2,2-trifluoroacetate (3-5)

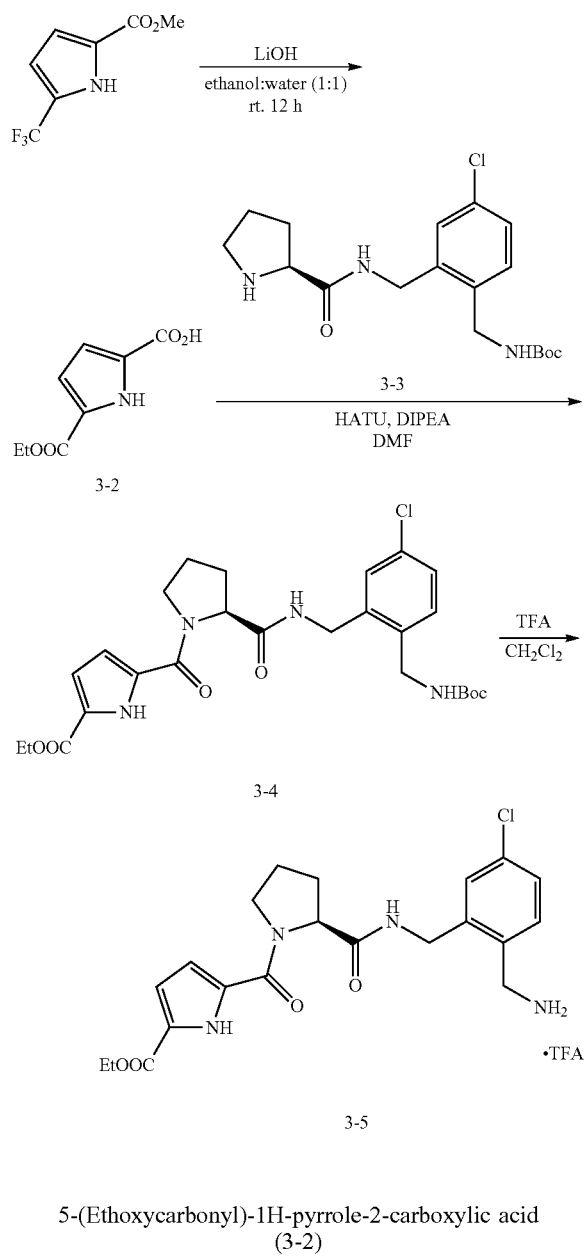

5-(Ethoxycarbonyl)-1H-pyrrole-2-carboxylic acid (3-2)

To a solution of methyl-5-(trifluoromethyl)-1H-pyrrole-2-carboxylate (3-1, 0.05 g, 0.26 mmol) in EtOH:H$_2$O (1:1, 2.0 mL) was added LiOH (0.031 g, 1.29 mmol) and mixture was allowed to stir at room temperature for 106 h. The reaction mixture was concentrated under reduced pressure and residue was dissolved in water (5 mL) and acidified with 2M aqueous HCl solution to pH 3.0 and extracted with EtOAc (2×20 mL). The combined organic layers were washed with brine (10 mL) dried over anhydrous Na$_2$SO$_4$, and concentrated under reduced pressure. The residue was purified by column chromatography (silica gel, 20% EtOAc/hexanes) to provide acid 3-2.

(S)-Ethyl-5-(2-{(2-[{(tert-butoxycarbonyl) amino}methyl]-5-chlorobenzyl) carbamoyl}pyrrolidine-1-carbonyl)-1H-pyrrole-2-carboxylate (3-4)

HATU (0.228 g, 0.60 mmol) was added in portion to the solution of amine 3-3 (0.20 g, 0.54 mmol), acid 3-2 (0.10 g, 0.65 mmol) and DIPEA (0.19 mL, 1.09 mmol) in DMF (2.0 mL) at 0° C. and reaction mixture was stirred at room temperature for 2 h. The reaction mixture was quenched with water (30 mL) and extracted with EtOAc (2×30 mL). The combined organic layer washed with saturated aqueous NaHCO$_3$ solution (15 mL), water (2×50 mL), brine (20 mL), dried over anhydrous Na$_2$SO$_4$, filtered and concentrated under reduced pressure. The residue was purified by column chromatography (silica gel, ethylacetate/hexanes: 2:3) to provide amide 3-4.

(S)-Ethyl-5-[2-{(2-(aminomethyl)-5-chlorobenzyl) carbamoyl}pyrrolidine-1-carbonyl]-1H-pyrrole-2-carboxylate (3-5)

A mixture of amide 3-4 (0.02 mg, 0.038 mmol) and TFA (0.43 µL, 0.57 mmol) in CH$_2$Cl$_2$ (2.0 mL) and water (10 µL) was stirred at room temperature for 16 h. The solvent and volatiles were removed under reduced pressure and residue was purified by reverse phase combiflash column chromatography (C18, eluent: 0-20% acetonitrile/water) to provide 3-5. $^1$H NMR (300 MHz, CDCl$_3$): δ 7.73, (d, J=8.4 Hz, 1H), 7.66 (d, J=8.4 Hz, 2H), 7.57-7.50 (m, 1H), 7.41-7.34 (m, 1H), 5.0 (s, 2H), 1.37 (s, 9H).

EXAMPLE 4

Preparation of (S)—N-{2-(Aminomethyl)-5-chlorobenzyl}-1-{5-(trifluoromethyl)-1H-pyrrole-2-carbonyl}pyrrolidine-2-carboxamide (4-5)

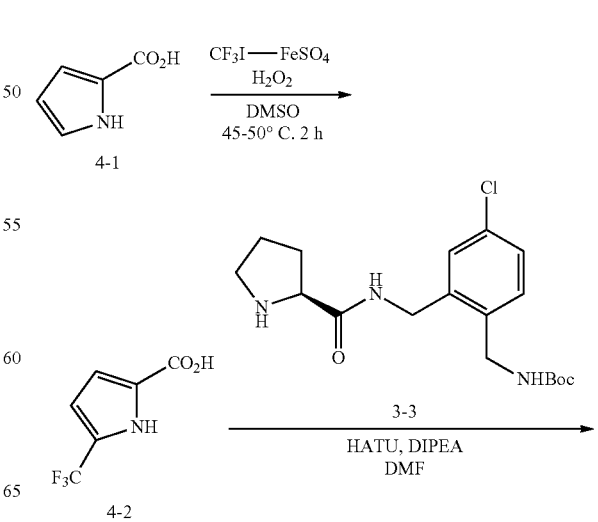

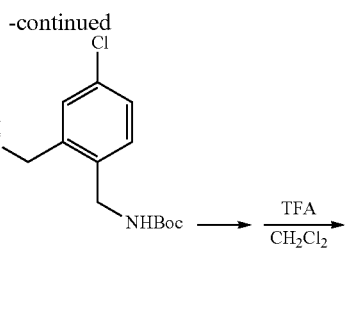

4-4

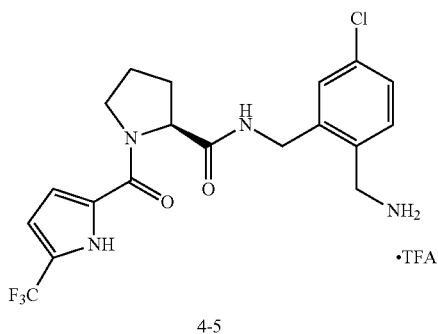

4-5

5-(Trifluoromethyl)-1H-pyrrole-2-carboxylic acid (4-2)

A solution of H$_2$SO$_4$ in DMSO (9.45 mL, 1.0 mol/L), solution of CF$_3$I in DMSO (11.0 mL, 3 mol/L) and aqueous solution of FeSO$_4$ (3.75 mL, 1.0 mol/L) was added in sequence to a solution of pyrrole-2-carboxylic acid 4-1 (1.0 g, 9.0 mmol) in DMSO (30 ml) at room temperature. Thereafter, H$_2$O$_2$ (1.02 mL, 18.00 mmol, 30% in water) was added dropwise to the mixture and stirred at room temperature for 30 min. The reaction mixture was diluted with water (100 mL), extracted with EtOAc (3×100 mL). The combined organic extracts were washed with water (50 mL), brine (50 mL), dried over anhydrous Na$_2$SO$_4$, filtered and concentrated under reduced pressure. The residue was purified by column chromatography (silica gel; eluent: EtOAc/hexanes, 3:2) to provide 5-(trifluoromethyl)-/H-pyrrole-2-carboxylic acid 4-2.

(S)-tert-Butyl-4-chloro-2-[{1-(5-(trifluoromethyl)-1H-pyrrole-2-carbonyl)pyrrolidine-2-carboxamido}methyl]benzylcarbamate (4-4)

HATU (0.228 g, 0.60 mmol) was added in portion to the mixture of amine 4-3 (0.20 g, 0.54 mmol), acid 4-2 (0.107 g, 0.60 mmol) and DIPEA (0.084 g, 0.65 mmol) in DMF (2.0 mL) and reaction mixture was stirred at 2 h. The reaction mixture was diluted with EtOAc (30 mL), washed with saturated aqueous NaHCO$_3$ solution (15 mL), water (2×50 mL), brine (20 mL) and dried over anhydrous Na$_2$SO$_4$. The organic layer was concentrated under reduced pressure. The residue was purified by column chromatography (silica gel, ethylacetate-hexanes, 2:3) to amide 4-4 as amorphous off white solid.

(S)—N-{2-(Aminomethyl)-5-chlorobenzyl}-1-{5-(trifluoromethyl)-1H-pyrrole-2-carbonyl}pyrrolidine-2-carboxamide (4-5)

A mixture of Boc protected amine 4-4 (0.182 g, 0.34 mmol) and TFA (0.26 mL, 3.44 mmol) in CH$_2$Cl$_2$ (2.0 mL) and water (50 μL) was stirred at room temperature for 16 h. The solvent and volatiles were removed at reduced pressure and residue was purified by reverse phase combiflash column chromatography (C18: eluent: 0-20% acetonitrile/water) to provide 4-5. $^1$H NMR (400 MHz, MeOD): δ 7.47 (s, 1H), 7.43 (d, J=8.3 Hz, 1H), 7.39 (d, J=8.3 Hz, 1H), 6.79 (d, J=3.6 Hz, 1H), 6.63 (d, J=3.6 Hz, 1H), 4.59 (d, J=15.1 Hz, 1H), 4.55-4.49 (m, 1H), 4.31 (d, J=15.1 Hz, 1H), 4.29-4.19 (m, 2H), 4.00-3.88 (m, 2H), 2.36-2.21 (m, 1H), 2.20-1.90 (m, 3H).

EXAMPLE 5

Preparation of (S)—N-{2-(Aminomethyl)-5-chlorobenzyl}-1-(4-nicotinoyl-1H-pyrrole-2-carbonyl)pyrrolidine-2-carboxamide-bis(2,2,2-trifluoro acetate) (5-9)

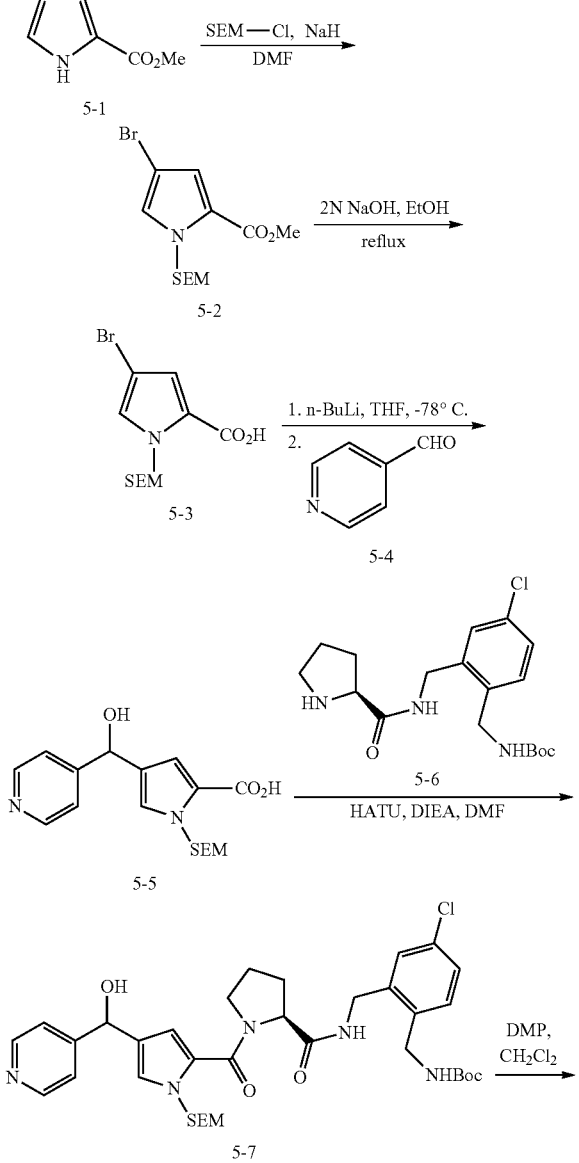

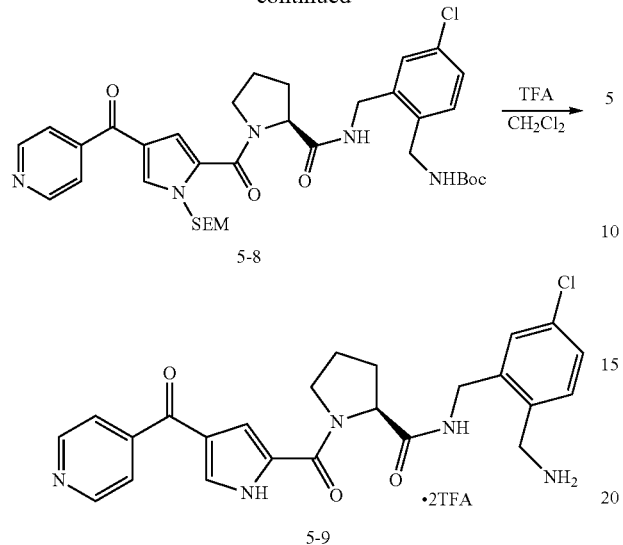

Methyl-4-bromo-1-[{2-(trimethylsilyl) ethoxy}methyl]-1H-pyrrole-2-carboxylate (5-2)

A solution of 4-bromo-1H-pyrrole-2-carboxylate 5-1 (1.0 g, 4.9 mmol) in DMF (2 mL) was added dropwise to the mixture of sodium hydride (0.22 g, 9.8 mmol) in DMF (5 mL) at 0° C. and mixture was stirred at same temperature for 30 min. SEM-Cl(0.95 mL, 5.39 mmol) was added dropwise and mixture was further stirred at room temperature for 14 h. The reaction mixture was quenched with ice-water (30 mL) and extracted with EtOAc (3×50 mL). The combined organic extract was washed with water (100 mL), brine (50 mL), dried over anhydrous Na$_2$SO$_4$, filtered and concentrated under reduced pressure. The residue was purified by reverse phase combiflash column chromatography (C18: eluent: 10-100% acetonitrile/water) to obtain pyrrole ester 5-2.

4-Bromo-1-[{2-(trimethylsilyl)ethoxy}methyl]-1H-pyrrole-2-carboxylic acid (5-3)

A solution of NaOH (0.24 g, 6.0 mmol) in water (3 mL) was added dropwise to a solution of ester 5-2 (0.3 g, 0.90 mmol) in ethanol (3 mL) and mixture was heated to reflux for 5 h. The organic solvent was removed under reduced pressure and the mixture was diluted with water (25 mL) and washed with MTBE (25 mL). The aqueous layer was acidified with 1M aqueous HCl to pH 2 and extracted with EtOAc (3×50 mL). The combined organic extract were washed with brine solution (25 mL), dried over anhydrous Na$_2$SO$_4$, filtered and concentrated. The residue was purified by reverse phase combiflash column chromatography (C18; eluent: 10-100% acetonitrile/water) to obtain amide 5-3.

4-{Hydroxyl(pyridine-4-yl)methyl}-1-[{2-(trimethylsilyl)ethoxy}methyl]-1H-pyrrole-2-carboxylic acid (5-5)

A solution of n-BuLi (1.6M in hexanes, 0.73 mL, 1.17 mmol) was added dropwise to a solution of bromopyrrole acid 5-3 (0.15 g, 0.47 mmol) in anhydrous THF (3 mL) at −78° C. and mixture was stirred at same temperature for 1 h. A solution of aldehyde 5-4 (0.066 mL, 0.70 mmol) in THF (5 mL) was added dropwise and mixture was stirred at −78° C. for 4 h. The mixture was quenched with water (30 mL) at 0° C. and allowed to warm to room temperature. The reaction mixture was diluted with water (30 mL), neutralized to pH 5-6 with 1M aqueous HCl and extracted with EtOAc (3×50 mL). The combined organic layers were washed with brine (25 mL), dried over anhydrous Na$_2$SO$_4$, filtered and concentrated. The residue was purified by reverse phase combiflash column chromatography (C18: eluent: acetonitrile/water) to obtain amide 5-5.

tert-Butyl-4-chloro-2-[{(2S)-1-(4-(hydroxy(pyridin-4-yl)methyl)-1-((2-(trimethyl silyl)ethoxy)methyl)-1H-pyrrole-2-carbonyl)pyrrolidine-2-carboxamido}methyl]benzylcarbamate (5-7)

The mixture of acid 5-5 (0.025 g, 0.072 mmol), amine 5-6 (0.026 g, 0.072 mmol), HATU (0.055 g, 0.144 mmol), DIPEA (0.038 mL, 0.216 mmol) in DMF (2 mL) was stirred at room temperature for 6 h. The reaction mixture was diluted with EtOAc (50 mL) and washed with saturated aqueous NaHCO$_3$ solution (20 mL), brine solution (2×20 mL). The organic layer was separated, dried over anhydrous Na$_2$SO$_4$, filtered and concentrated under redcued pressure. The residue was purified by reverse phase combiflash column chromatography (C18; eluent: 10-100% acetonitrile/water) to obtain amide 5-7.

(S)-tert-Butyl-4-chloro-2-[{1-(4-isonicotinoyl-1-((2-(trimethylsilyl)ethoxy)methyl)-1H-pyrrole-2-carbonyl)pyrrolidine-2-carboxamido}methyl]benzylcarbamate (5-8)

Dess-Martin Periodinane (0.067 g, 0.158 mmol) was added in portions to a solution of alcohol 5-7 (0.10 g, 0.144 mmol) in CH$_2$Cl$_2$ (2 mL) and mixture was stirred at room temperature for 2 h. The reaction mixture was diluted with CH$_2$Cl$_2$ (20 mL), cooled to 0° C. and quenched with 5% aqueous solutions of Na$_2$SO$_3$ and NaHCO$_3$ (20 mL, 1:1) and mixture was stirred at room temperature for 30 min. The organic layer was separated and aqueous layer was extracted with CH$_2$Cl$_2$ (2×25 mL). The combined organic layers were washed with water (25 mL), brine (25 mL), dried over anhydrous Na$_2$SO$_4$, filtered and concentrated under redcued pressure. The residue was purified by reverse phase combiflash column chromatography (C18; eluent: 10-100% acetonitrile/water) to obtain amide 5-8.

(S)—N-{2-(Aminomethyl)-5-chlorobenzyl}-1-(4-nicotinoyl-1H-pyrrole-2-carbonyl) pyrrolidine-2-carboxamide-bis(2,2,2-trifluoroacetate) (5-9)

Trifluoro acetic acid (1.0 mL, 13.06 mmol) was added to the solution of 5-8 (0.05 g, 0.07 mmol) in CH$_2$Cl$_2$ (1 mL) and reaction mixture was stirred at room temperature for 24 h. Volatile by-products were removed at reduced pressure residue. The residue was purified by reverse phase combiflash column chromatography (C18; eluent: 10-100% acetonitrile:water) to obtain 5-9. $^1$H NMR (MeOD-d$_4$, 300 MH$_Z$) (δ) ppm: 8.74-8.72 (d, J=5.7 Hz, 2H), 7.73-7.71 (m, 2H), 7.56-7.24 (m, 5H), 4.51-4.39 (m, 2H), 4.38-4.23 (m, 3H), 3.97-3.93 (m, 2H), 2.30-1.92 (m, 4H).

EXAMPLE 6

Preparation of (2S)-N-{2-(Aminomethyl)-5-chlorobenzyl}-1-[4-{hydroxyl(pyridine-4-yl)methyl}-1H-pyrrole-2-carbonyl]pyrrolidine-2-carboxamide-bis(2,2,2-trifluoroacetate) (6-2)

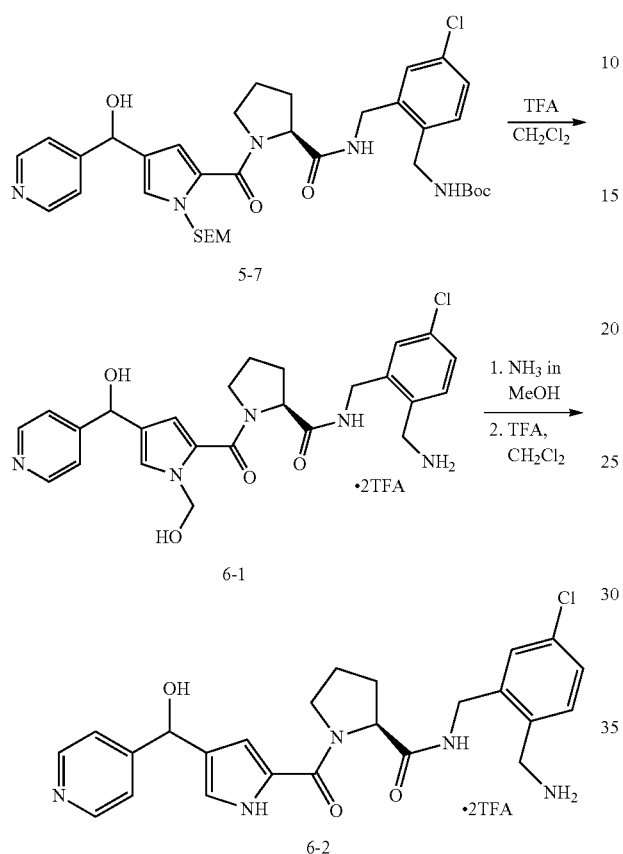

(2S)-N-{2-(Aminomethyl)-5-chlorobenzyl}-1-{4-hydroxy(pyridine-4-yl)methyl}-1-(hydroxymethyl)-1H-pyrrole-2-(carbonyl)pyrrolidine-2-carboxamide-bis(2,2,2-trifluoroacetate (6-1)

Trifluoro acetic acid (0.30 mL, 3.91 mmol) was added to the solution of boc-amine 5-7 (0.20 g, 0.28 mmol) in $CH_2Cl_2$ (2 mL) and reaction mixture was stirred at room temperature for 2.5 h. The solvent and volatiles were removed at reduced pressure and crude intermediate 6-1 was used in the next step without purification.

(2S)-N-{2-(Aminomethyl)-5-chlorobenzyl}-1-[4-{hydroxy(pyridine-4-yl)methyl}-1H-pyrrole-2-carbonyl]pyrrolidine-2-carboxamide (6-2)

A mixture of intermediate 6-1 (from above step) and $NH_3$ solution (7N in methanol, 2 mL) was stirred at room temperature for 1 h. The organic solvent was removed under reduced pressure and water (10 mL) was added to the mixture. The solid separated was filtered, washed with hexanes, and dried under high vacuum. The solid was dissolved in $CH_2Cl_2$ (2 mL) and trifluoro acetic acid (0.3 mL) was added and mixture was stirred for 20 min. The solvent and volatiles were removed under reduced pressure. The residue purified by semi-preparative HPLC (C18; eluent: 10-90% acetonitrile:water) to obtain 6-2. $^1$H NMR (MeOD-$d_4$, 300 MHz) (δ) ppm: 8.73-8.50 (m, 2H), 8.08-7.90 (m, 2H), 7.62-7.35 (m, 3H), 7.15-6.85 (m, 1H), 6.58-6.50 (m, 1H), 5.99-5.78 (m, 1H), 4.64-4.49 (m, 2H), 4.37-4.28 (m, 3H), 3.88-3.67 (m, 2H), 2.24-1.93 (m, 4H).

EXAMPLE 7

Preparation of (S)—N-{2-(Aminomethyl)-5-chlorobenzyl}-1-{4-(pyridin-4-ylmethyl)-1H-pyrrole-4-carbonyl}pyrrolidine-2-carboxamide-bis(2,2,2-trifluoroacetate) (7-1)

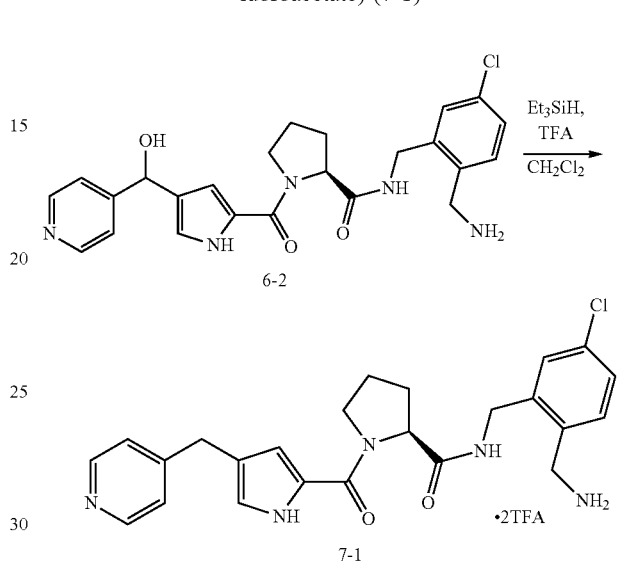

(S)—N-{2-(Aminomethyl)-5-chlorobenzyl}-1-{4-(pyridin-4-ylmethyl)-1H-pyrrole-2-carbonyl}pyrrolidine-2-carboxamide-bis(2,2,2-trifluoroacetate) (7-1)

Trifluoro acetic acid (2.0 mL, 26.12 mmol) and $Et_3SiH$ (0.10 mL, 0.64 mmol) was added dropwise to a solution of 6-2 (0.15 g, 0.216 mmol) in $CH_2Cl_2$ (2 mL) and mixture was stirred at room temperature for 14 h. The solvent and volatiles were removed at reduced pressure residue. The residue was purified by semi-preparative HPLC (column: eluent: 10-90% acetonitrile:water) to obtain 7-1. $^1$H NMR (MeOD-$d_4$, 300 MHz) (δ) ppm: 8.63 (brs, 2H), 7.80 (brs, 2H), 7.46-7.39 (m, 3H), 6.93 (br. s, 1H), 6.68 (brs, 1H), 4.62-4.50 (m, 2H), 4.37-4.14 (m, 5H), 3.95-3.80 (m, 2H), 2.26-1.98 (m, 4H).

EXAMPLE 8

Preparation of (S)—N-{2-(aminomethyl)-5-chlorobenzyl}-1-(4-nicotinoyl-1H-pyrrole-2-carbonyl)pyrrolidine-2-carboxamide-bis(2,2,2-trifluoro acetate (8-8)

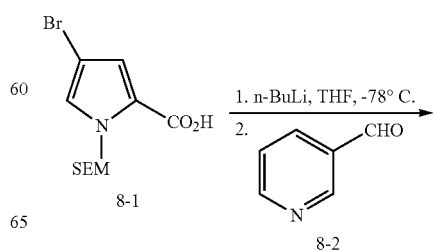

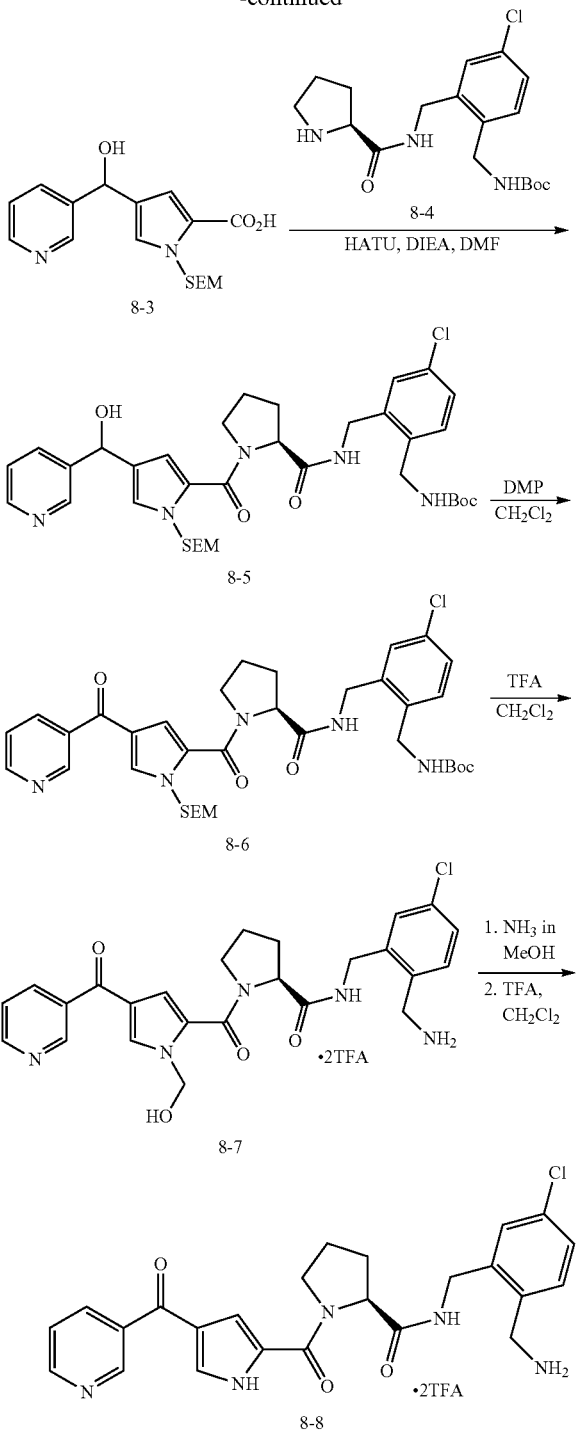

THF (5 mL) was added dropwise and mixture was stirred at −78° C. for 4 h. The mixture was quenched with water (30 mL) at 0° C. and allowed to warm to room temperature. The reaction mixture was diluted with water (30 mL), neutralized to pH 5-6 with 1M aqueous HCl and extracted with EtOAc (3×50 mL). The combined organic layers were washed with brine (25 mL), dried over anhydrous Na$_2$SO$_4$, filtered and concentrated. The residue was purified by reverse phase combiflash column chromatography (C18: eluent: acetonitrile/water) to obtain acid 8-3.

tert-Butyl-4-chloro-2-[{(2S)-1-[4-{hydroxy(pyridine-3-yl)methyl}-1-{(2-(trimethyl silyl)ethoxy}methyl}-1H-pyrrole-2-carbonyl]pyrrolidine-2-carboxamido}methyl]benzylcarbamate (8-5)

The mixture of acid 8-3 (0.50 g, 1.44 mmol), amine 8-4 (0.53 g, 1.44 mmol), HATU (0.82 g, 2.15 mmol), DIPEA (0.63 mL, 3.6 mmol) in DMF (10 mL) was stirred at room temperature for 2 h. The reaction mixture was diluted with EtOAc (100 mL) and washed with saturated aqueous NaHCO$_3$ solution (50 mL), brine solution (2×25 mL). The organic layer was separated, dried over anhydrous Na$_2$SO$_4$, filtered and concentrated under reduced pressure. The residue was purified by reverse phase combiflash column chromatography (C18; eluent: 10-100% acetonitrile:water) to obtain amide 8-5.

(S)-tert-Butyl-4-chloro-2-[{1-(4-nicotinoyl-1-[{2-(trimethylsilyl)ethoxy}methyl]-1H-pyrrole-2-carbonyl)pyrrolidine-2-carboxamido}methyl]benzylcarbamate (8-6) Dess-Martin Periodinane (0.067 g, 0.157 mmol) was added in portions to a solution of alcohol 8-5 (0.10 g, 0.14 mmol) in CH$_2$Cl$_2$ (8 mL) and reaction mixture was stirred at room temperature for 2 h. The reaction mixture was diluted with CH$_2$Cl$_2$ (50 mL), cooled to 0° C. and added quenched with 5% aqueous solutions of sodium thiosulphate and sodium bicarbonate (50 mL, 1:1). The mixture was stirred at room temperature for 30 min. The organic layer was separated and aqueous layer was extracted with CH$_2$Cl$_2$ (2×25 mL). The combined organic layers were washed with water (25 mL), brine (25 mL), dried over anhydrous Na$_2$SO$_4$, filtered and concentrated under redcued pressure to obtain ketone 8-6. The residue was used in the next step without further purification.

(S)—N-{2-(Aminomethyl)-5-chlorobenzyl}-1-{1-(hydroxymethyl)-4-nicotinoyl-1H-pyrrole-2-carbonyl}pyrrolidine-2-carboxamide-bis(2,2,2-trifluoroacetate) (8-7)

Trifluoro acetic acid (1.0 mL, 13.06 mmol) was added to the solution of ketone 8-6 (0.098 g, 1.41 mmol) in CH$_2$Cl$_2$ (1 mL) and reaction mixture was stirred at room temperature for 48 h. The solvent and volatiles were removed at reduced pressure residue. The residue was purified by reverse phase combiflash column chromatography (C18; eluent: 10-100% acetonitrile:water) to obtain amine 8-7.

(S)—N-{2-(Aminomethyl)-5-chlorobenzyl}-1-(4-nicotinoyl-1H-pyrrole-2-carbonyl) pyrrolidine-2-carboxamide-bis(2,2,2-trifluoroacetate) (8-8)

NH$_3$ solution (7N in MeOH, 2 mL) was added dropwise to a solution of intermediate 8-7 (0.08 g, 0.11 mmol) in methanol (1.0 mL) at 0° C. The reaction mixture was warmed to room temperature and stirred for 2 h. The solvent and volatiles were removed and residue was purified by 4-{Hydroxyl(pyridine-3-yl)methyl}-1-[{2-(trimethylsilyl)ethoxy}methyl]-1H-pyrrole-2-carboxylic acid (8-3)

A solution of n-BuLi (1.6M solution in hexanes, 4.88 mL, 7.81 mmol) was added dropwise to a solution of 4-bromo-1-[{2-(trimethylsilyl)ethoxy}methyl]-1H-pyrrole-2-carboxylic acid 8-1 (1.0 g, 3.12 mmol) in anhydrous THF (5 mL) at −78° C. and mixture was stirred at same temperature for 1 h. A solution of aldehyde 8-2 (0.44 mL, 4.68 mmol) in reverse phase combiflash column chromatography (C18; eluent: 10-100% acetonitrile:water) to obtain pyrrole amine (0.045 g, crude) as off-white solid.

Trifluoro acetic acid (0.023 mL, 0.30 mmol) was added to a solution of above amine in $CH_2Cl_2$ (1 mL) and mixture was stirred at room temperature for 30 min. The solvent and volatiles were removed under reduced pressure and residue was purified by reverse phase combiflash column chromatography (C18; eluent: 10-100% acetonitrile:water) to obtain 8-8. $^1$H NMR (MeOD-$d_4$, 300 MH$_Z$) (δ) ppm: 8.94 (s, 1H), 8.75-8.74 (d, J=3.6 Hz, 1H), 8.35-8.17 (m, 1H), 7.67-7.58 (m, 2H), 7.48-7.37 (m, 2H), 7.25 (s, 1H), 7.10-6.67 (m, 1H), 4.57-4.35 (m, 3H), 4.24 (brs, 2H), 3.98-3.94 (m, 2H), 2.42-1.93 (m, 4H).

EXAMPLE 9

Preparation of (2S)-N-{2-(Aminomethyl)-5-chlorobenzyl}-1-[4-{hydroxy(pyridine-3-yl}methyl]-1H-pyrrole-2-carbonyl)pyrrolidine-2-carboxamide (9-2)

pressure residue. The residue was purified by reverse phase combiflash column chromatography (C18; eluent: 10-100% acetonitrile:water) to obtain 9-1 as a white solid.

(2S)-N-{2-(Aminomethyl)-5-chlorobenzyl}-1-[4-{hydroxy(pyridine-3-yl)methyl}-1H-pyrrole-2-carbonyl]pyrrolidine-2-carboxamide (9-2)

$NH_3$ solution (7N in MeOH, 3 mL) was added dropwise to a solution of intermediate 8 (0.12 g, 0.24 mmol) in methanol (1.0 mL) at 0° C. The reaction mixture was warmed to room temperature and stirred for 2 h. The solvent and volatiles were removed and residue was purified by reverse phase semi preparative HPLC (C18; eluent: 10-100% acetonitrile/water) to obtain pyrrole amine 9-2. $^1$H NMR (MeOD-$d_4$, 400 MH$_Z$) (δ) ppm: 8.72-8.20 (m, 2H), 7.98-7.60 (m, 1H), 7.39-7.11 (m, 5H), 6.98-6.70 (m, 1H), 6.62-5.81 (m, 1H), 4.50-4.42 (m, 2H), 4.18-4.02 (m, 3H), 3.90-3.71 (m, 2H), 2.30-1.89 (m, 4H).

EXAMPLE 10

Preparation of (S)—N-{2-(Aminomethyl)-5-chlorobenzyl}-1-(4-picolinoyl-1H-pyrrole-2-carbonyl)pyrrolidine-2-carboxamide-bis(2,2,2-trifluoro acetate) (10-7)

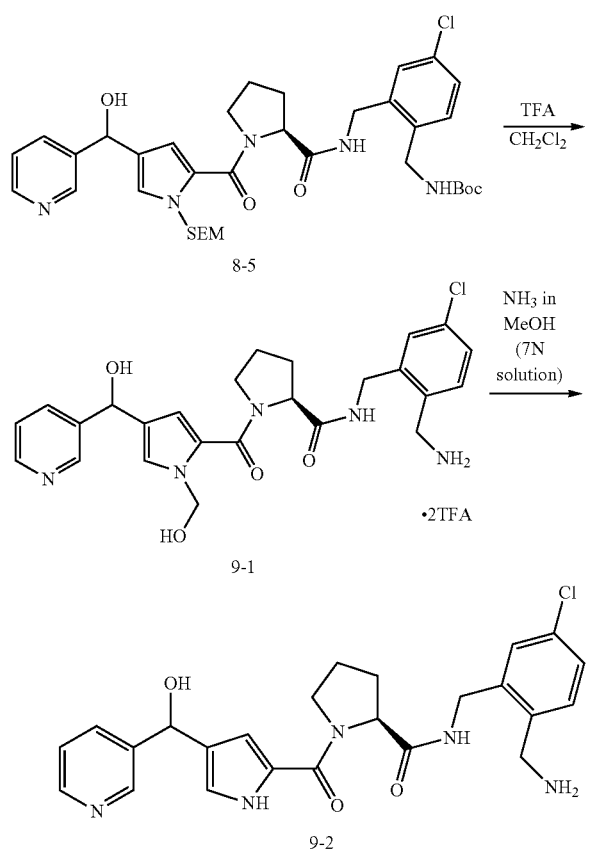

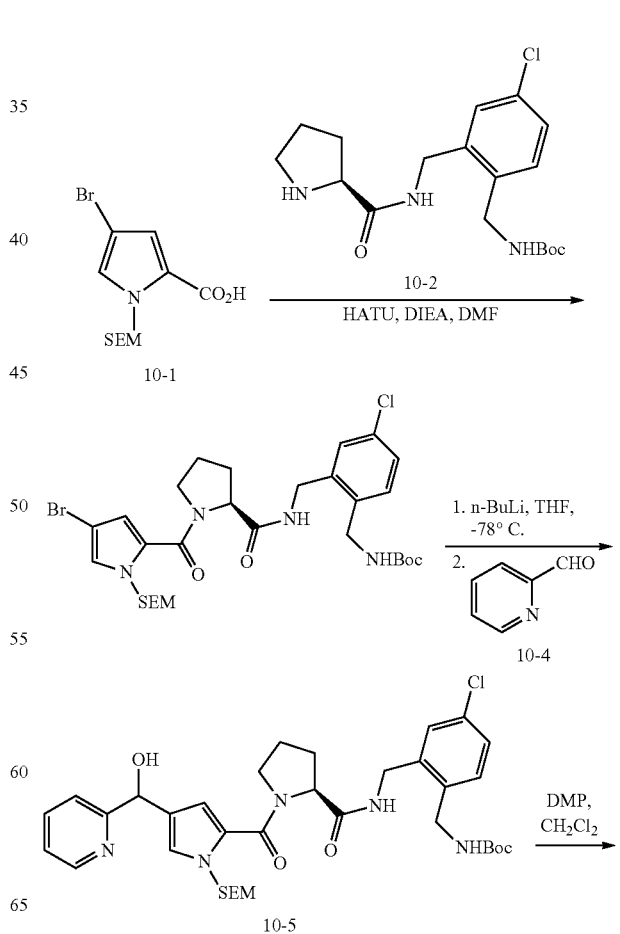

(2S)-N-{2-(Aminomethyl)-5-chlorobenzyl}-1-{4-hydroxy(pyridine-3-yl)methyl}-1-(hydroxymethyl)-1H-pyrrole-2-carbonyl)pyrrolidine-2-carboxamide-bis(2,2,2-trifluoroacetate (9-1)

Trifluoro acetic acid (1.0 mL, 13.06 mmol) was added to the solution of 8-5 (0.30 g, 0.43 mmol) in $CH_2Cl_2$ (1 mL) and reaction mixture was stirred at room temperature for 14 h. The solvent and volatiles were removed at reduced -continued

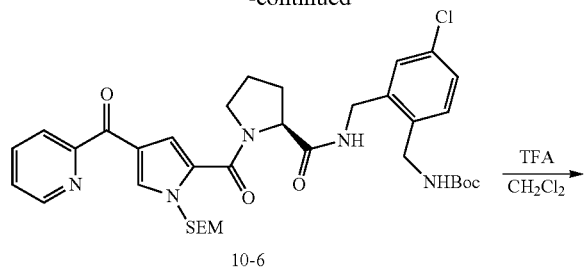

10-6 in CH₂Cl₂ (5 mL) and mixture was stirred at room temperature for 2 h. The reaction mixture was diluted with CH₂Cl₂ (50 mL), cooled to 0° C. and quenched with 5% aqueous solutions of sodium thiosulphate and sodium bicarbonate (50 mL, 1:1). The reaction mixture was stirred at room temperature for 30 min. The organic layer was separated and aqueous layer was extracted with CH₂Cl₂ (2×50 mL). The combined organic layers were washed with water (50 mL), brine (25 mL), dried over anhydrous Na₂SO₄, filtered and concentrated under reduced pressure to obtain amide 10-6 as pale yellow solid.

(S)—N-{2-(Aminomethyl)-5-chlorobenzyl}-1-(4-picolinoyl-1H-pyrrole-2-carbonyl) pyrrolidine-2-carboxamide-bis(2,2,2-trifluoroacetate) (10-7)

Trifluoro acetic acid (2.0 mL, 26.10 mmol) was added to a solution of 10-6 (0.07 g, 0.10 mmol) in CH₂Cl₂ (2 mL) and reaction mixture was stirred at room temperature for 2 h. The solvent and volatiles were removed at reduced pressure residue and residue was purified by reverse phase combiflash column chromatography (C18; eluent: 10-100% acetonitrile:water) to obtain 10-7. $^1$H NMR (MeOD-d₄, 400 MH$_Z$) (δ) ppm: 8.71-8.70 (d, J=4.0 Hz, 1H), 8.20 (brs, 1H), 8.05-8.0 (m, 2H), 7.62-7.58 (m, 1H), 7.47-7.40 (m, 3H), 7.22-6.94 (m, 1H), 4.57-4.51 (m, 2H), 4.38-4.34 (d, J=15.2 Hz, 1H), 4.29-4.25 (m, 2H), 4.03-3.97 (m, 2H), 2.28-1.95 (m, 4H).

10-7

(S)-tert-Butyl-2-[{1-(4-bromo-1-((2-(trimethylsilyl)ethoxy)methyl)-1H-pyrrole-2-carbonyl)pyrrolidine-2-carboxamido}methyl]-4-chlorobenzylcarbamate (10-3)

A mixture of acid 10-1 (0.87 g, 2.72 mmol), amine 10-2 (1.0 g, 2.72 mmol), HATU (1.55 g, 4.9 mmol), DIPEA (1.20 mL, 6.80 mmol) in DMF (5 mL) was stirred at room temperature for 2 h. The reaction mixture was diluted with EtOAc (100 mL) and washed with saturated aqueous NaHCO₃ solution (50 mL), brine solution (2×25 mL). The organic layer was separated, dried over anhydrous Na₂SO₄, filtered and concentrated under reduced pressure. The residue was purified by reverse phase combiflash column chromatography (C18; eluent: 10-100% acetonitrile/water) to obtain amide 10-3 as pale yellow solid.

tert-Butyl-4-chloro-2-[{(2S)-1-(4-(hydroxy(pyridin-2-yl)methyl)-1-((2-(trimethyl silyl)ethoxy)methyl)-1H-pyrrole-2-carbonyl)pyrrolidine-2-carboxamido}methyl]benzylcarbamate (10-5)

A solution of n-BuLi (1.6M in hexanes, 0.70 mL, 1.12 mmol) was added dropwise to a solution of bromopyrrole 10-3 (0.50 g, 0.75 mmol) in anhydrous THF (5 mL) at −78° C. and mixture was stirred at same temperature for 1 h. A solution of aldehyde 10-4 (0.107 g, 1.12 mmol) in THF (5 mL) was added dropwise and mixture was stirred at −78° C. for 4 h. The mixture was quenched with water (30 mL) at 0° C. and allowed to warm to room temperature. The reaction mixture was diluted with water (30 mL), neutralized to pH 5-6 with 1M aqueous HCl and extracted with EtOAc (3×50 mL). The combined organic layers were washed with brine (25 mL), dried over anhydrous Na₂SO₄, filtered and concentrated. The residue was purified by reverse phase combiflash column chromatography (C18; eluent: 10-100% acetonitrile/water) to obtain amide 10-5 as pale yellow solid.

(S)-tert-Butyl-4-chloro-2-[{1-(4-picolinoyl-1-{(2-(trimethylsilyl)ethoxy}methyl)-1H-pyrrole-2-carbonyl)pyrrolidine-2-carboxamido}methyl]benzylcarbamate (10-6)

Dess Martin periodinane (0.053 g, 0.126 mmol) was added in potion to a solution of 10-5 (0.08 g, 0.115 mmol)

EXAMPLE 11

Preparation of (2S)-N-{2-(Aminomethyl)-5-chlorobenzyl}-1-[4-{hydroxyl(pyridine-2-yl)methyl}-1H-pyrrole-2-carbonyl]pyrrolidine-2-carboxamide (11-2)

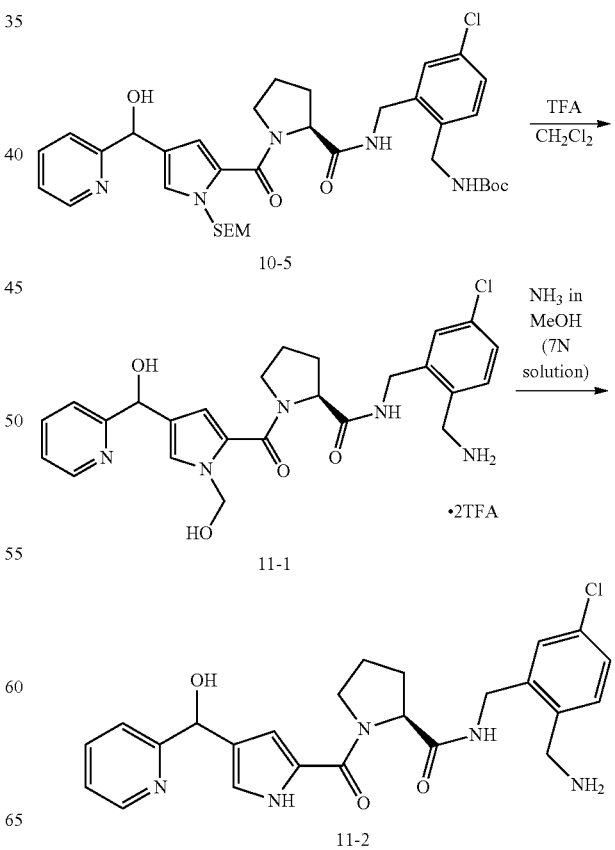

(2S)-N-{2-(Aminomethyl)-5-chlorobenzyl}-1-[4-{hydroxyl(pyridine-2-yl)methyl)}-1-(hydroxylmethyl)-1H-pyrrole-2-carbonyl]pyrrolidine-2-carboxamide-bis(2,2,2-trifluoroacetate) (11-1)

Trifluoro acetic acid (1.0 mL, 13.06 mmol) was added to the solution of 10-5 (0.58 g, 0.83 mmol) in CH$_2$Cl$_2$ (1 mL) and reaction mixture was stirred at room temperature for 14 h. The solvent and volatiles were removed at reduced pressure residue and residue was purified by reverse phase combiflash column chromatography (C18; eluent: 10-100% acetonitrile/water) to obtain 11-1 as a white solid.

(2S)-N-{2-(Aminomethyl)-5-chlorobenzyl}-1-[4-{hydroxyl(pyridin-2-yl)methyl}-1H-pyrrole-2-carbonyl]pyrrolidine-2-carboxamide (11-2)

A solution of NH$_3$ (7N in MeOH; 5 mL) was added dropwise to a solution of 11-1 (0.52 g, 0.71 mmol) in methanol (1 mL) and reaction mixture was warmed to room temperature and further stirred for 1 h at same temperature. The solvent was removed at reduced pressure and residue was purified by reverse phase semi-preparative HPLC (C18; eluent: 10-100% acetonitrile/water) to obtain 11-2. $^1$H NMR (MeOD-d$_4$, 300 MH$_Z$) (δ) ppm: 8.46-8.45 (d, J=4.2 Hz, 1H), 7.90-7.85 (m, 1H), 7.66-7.30 (m, 5H), 6.88-6.70 (m, 2H), 5.91-5.30 (m, 1H), 4.51-4.22 (m, 5H), 3.86-3.77 (m, 2H), 2.24-1.85 (m, 4H).

EXAMPLE 12

Preparation of (S)—N-{2-(Aminomethyl)-5-chlorobenzyl}-1-{4-(pyridin-2-ylmethyl)-1H-pyrrole-2-carbonyl}pyrrolidine-2-carboxamide-bis(2,2,2-trifluoroacetate) (12-1)

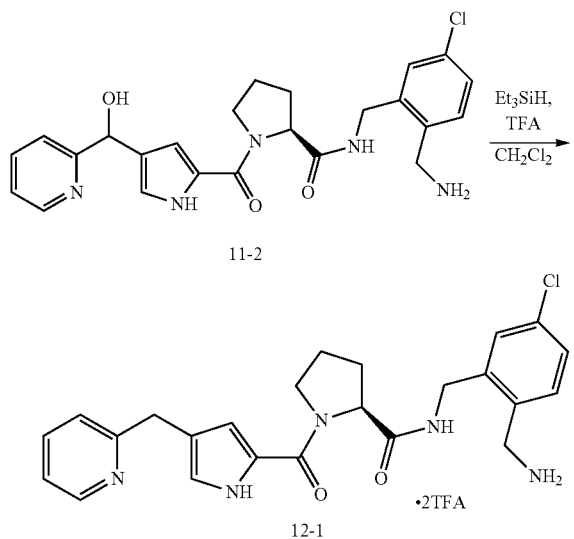

Trifluoro acetic acid (1.0 mL, 13.06 mmol) and Et$_3$SiH (0.08 mL, 0.51 mmol) was added to a solution of 11-2 (0.08 g, 0.17 mmol) in CH$_2$Cl$_2$ (2 mL) and mixture was stirred at room temperature for 14 h. The solvent and volatiles were removed at reduced pressure residue and residue was purified by reverse phase combiflash column chromatography (C18; eluent: 10-100% acetonitrile:water) to obtain 12-1. $^1$H NMR (MeOD-d$_4$, 300 MH$_Z$) (δ) ppm: 8.62-8.60 (m, 1H), 8.36-8.25 (m, 1H), 7.79-7.39 (m, 5H), 6.94-6.64 (m, 2H), 4.50-4.22 (m, 7H), 3.88-3.80 (m, 2H), 2.25-1.85 (m, 4H).

EXAMPLE 13

Preparation of (S)—N-{2-(Aminomethyl)-5-chlorobenzyl)-1-{4-(pyridin-4-yl)-1H-pyrrole-2-carbonyl) pyrrolidine-2-carboxamide-bis(2,2,2-trifluoroacetate) (13-10)

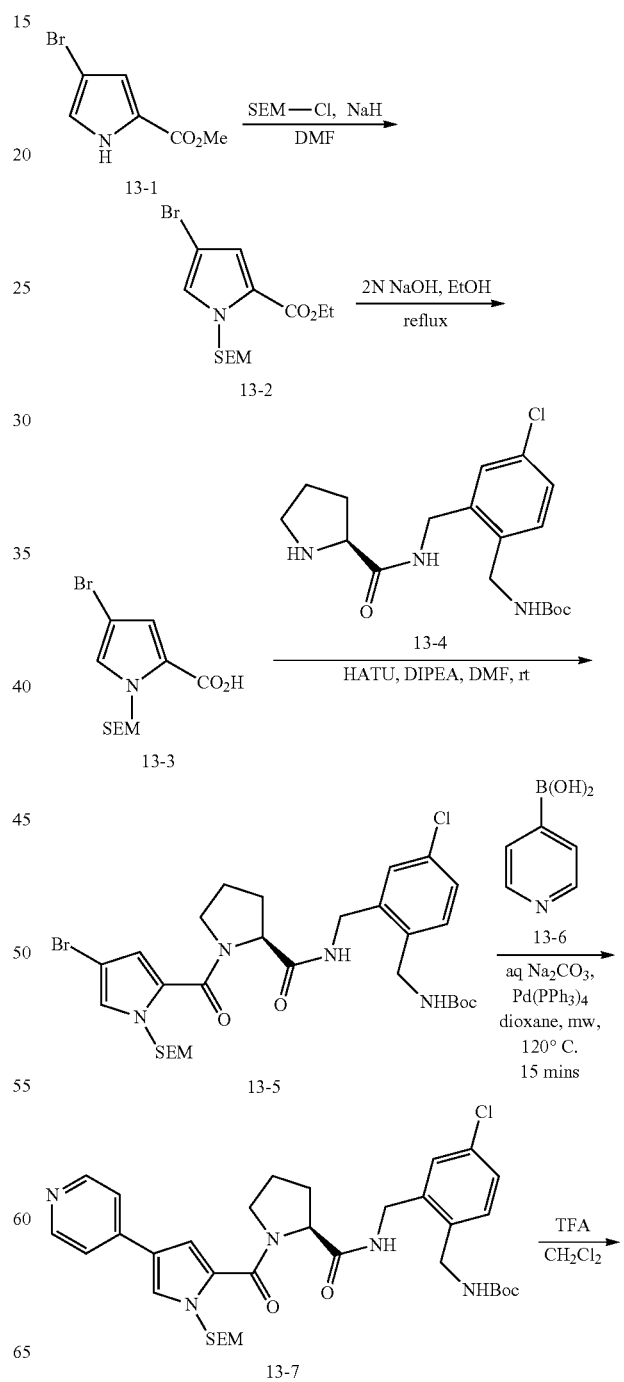

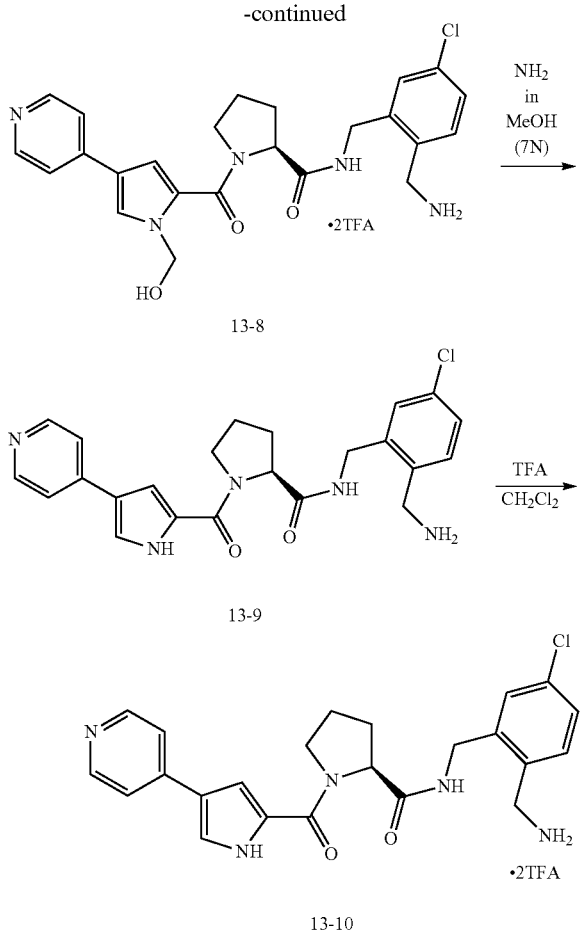

Ethyl-4-bromo-1-{(2-trimethylsilyl)ethoxy}methyl-1H-pyrrole-2-carboxylate (13-2) A solution of Methyl-4-bromo-1H-pyrrole-2-carboxylate 13-1 (5.0 g, 24.50 mmol) in DMF (5 mL) was added dropwise to the suspension of NaH (1.87 g, 49.01 mmol) in DMF (50 mL) at 0° C. and mixture was stirred for 30 min. Thereafter, SEM-Cl (4.76 mL, 26.96 mmol) was added and mixture was stirred at room temperature for 14 h. The mixture was quenched with ice-water (50 mL) and extracted with EtOAc (3×100 mL). The combined organic extract was washed with water (100 mL), brine (50 mL) and dried over $Na_2SO_4$, filtered, and evaporated under reduced pressure. The residue was purified by reverse phase combiflash column chromatography (C18; eluent: 10-100% acetonitrile/water) to obtain SEM protected pyrrole ester 13-2.

4-Bromo-1-{(2-(trimethylsilyl)ethoxy)methyl}-1H-pyrrole-2-carboxylic acid (13-3)

A solution of NaOH (2.0 g, 52.39 mmol) in water (10 mL) was added dropwise to a solution of pyrrole ester 13-2 (3.5 g, 10.47 mmol) in ethanol (30 mL) and mixture was heated to reflux for 6 h. The solvent was removed at reduced pressure, residue was diluted with water (50 mL) and washed with MTBE (25 mL). The aqueous layer was acidified with 1N aqueous HCl (10 mL) to pH 3 and extracted with EtOAc (3×100 mL). The combined organic extract were washed with brine solution (25 mL), dried over anhydrous $Na_2SO_4$, filtered and concentrated to provide acid 13-3.

(S)-tert-Butyl-[2-[{1-(4-bromo-1-[{2-(trimethylsilyl)ethoxy}methyl]-1H-pyrrole-2-carbonyl}pyrrolidine-2-carboxamido]methyl]-4-chlorobenzylcarbamate (13-5)

DIPEA (4.5 mL, 25.78 mmol) was added dropwise to the mixture of acid 13-3 (3.3 g, 10.31 mmol), amine 13-4 (3.78, 10.31) and HATU (5.8 g, 15.46 mmol) in DMF (30 mL) at 0° C., and mixture was stirred at room temperature 4 h. The reaction mixture was diluted with EtOAc (100 mL) and washed with saturated aqueous $NaHCO_3$ solution (50 mL), brine solution (2×50 mL). The organic layer was separated, dried over anhydrous $Na_2SO_4$, filtered and concentrated under reduced pressure. The residue was purified by reverse phase combiflash column chromatography (C18; eluent: 10-100% acetonitrile/water) to obtain amide 13-5.

(S)-tert-Butyl-4-chloro-2-[[1-{4-(pyridin-4-yl)-1-[{2-(trimethylsilyl)ethoxy}methyl]-1H-pyrrole-2-carbonyl}pyrrolidine-2-carboxamido]methyl]benzylcarbamate (13-7)

A mixture of 13-5 (0.37 g, 0.55 mmol), 4-pyridyl boronic acid 13-6 (0.13 g, 1.10 mmol), $Pd(PPh_3)_4$ (0.12 g, 0.11 mmol) and aqueous $Na_2CO_3$ (0.29 g, 2.76 mmol) in degassed 1,4-dioxane (10 mL), was heated in microwave at 120° C. for about 15 min. The reaction mixture was diluted with $H_2O$ (10 mL) extracted with EtOAc (2×20 mL). The combined organic layers were washed with brine (2×10 mL), dried over anhydrous $Na_2SO_4$, filtered and concentrated under reduced pressure. The residue was purified by combiflash column chromatography (silica gel; eluent: MeOH/$CH_2Cl_2$) to obtain intermediate I3-7.

(S)—N-(2-(aminomethyl)-5-chlorobenzyl)-1-(1-(hydroxymethyl)-4-(pyridin-4-yl)-1H-pyrrole-2-carbonyl)pyrrolidine-2-carboxamide (13-8)

A 50% solution of TFA in $CH_2Cl_2$ (2 mL) was added to the solution of 13-7 (0.12 g, 0.18 mmol) in $CH_2Cl_2$ (1 mL) and mixture was stirred at room temperature for 16 h. The solvent and volatiles were removed at reduced pressure to provide 13-8.

(S)—N-{2-(Aminomethyl)-5-chlorobenzyl}-1-{4-(pyridin-4-yl)-1H-pyrrole-2-carbonyl}pyrrolidine-2-carboxamide (13-9)

A mixture of 13-8 (0.12 g, 0.18 mmol) and 7N solution of ammonia in methanol (2 mL) was stirred at room temperature for 2 h. The solvent was removed under reduced pressure and the residue was purified by combiflash column chromatography (silica gel; eluent: 6% MeOH, 2% $NH_4OH$, $CH_2Cl_2$) to obtain 13-9.

(S)—N-{2-(Aminomethyl)-5-chlorobenzyl}-1-{4-(pyridin-4-yl}-1H-pyrrole-2-carbonyl}pyrrolidine-2-carboxamide (13-10)

A mixture of Trifluoro acetic acid (0.0056 mL, 0.07 mmol) and intermediate I3-9 (16 mg, 0.03 mmol) and in $CH_2Cl_2$ (1 mL) was stirred at room temperature for 20 min. The solvent was removed under reduced pressure and residue was triturated with diethyl ether (3 mL), filtered to obtain 13-10. $^1$H NMR (MeOD-$d_4$, 400 MHz) (δ) ppm: 8.58-8.57 (d, 2H), 8.19-8.17 (d, 2H), 7.95 (s, 1H), 7.55-7.40 (m, 4H), 4.58-4.54 (d, 1H), 4.36-4.38 (d, 2H), 4.29-4.27 (d, 2H), 4.06-0.99 (m, 2H), 2.31-2.28 (m, 1H), 2.19-2.16 (m, 1H), 2.14-2.07 (m, 1H), 1.95-2.01 (m, 1H).

EXAMPLE 14

Preparation of (S)—N-{2-(Aminomethyl)-5-chlorobenzyl}-1-{4-(pyridin-3-yl)-1H-pyrrole-2-carbonyl}pyrrolidine-2-carboxamide bis(2,2,2-trifluoroacetate) (14-5)

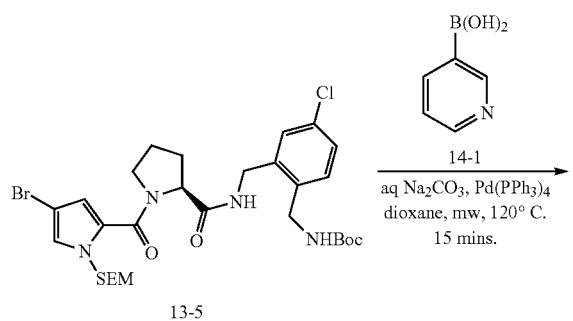
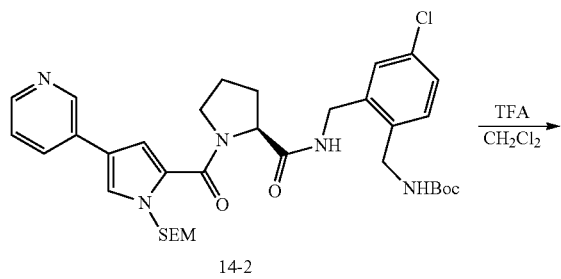
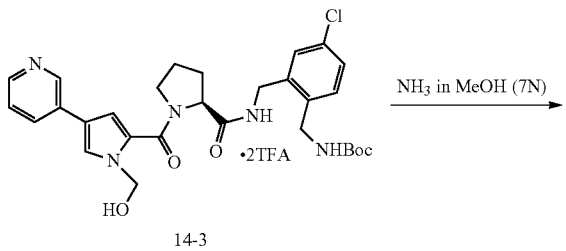
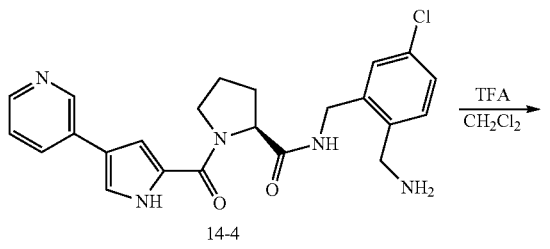

(S)-tert-Butyl-4-chloro-2-[1-{4-(pyridin-3-yl)-1-{(2-(trimethylsilyl)ethoxy}methyl]-1H-pyrrole-2-carbonyl)pyrrolidine-2-carboxamido)methyl)benzylcarbamate (14-2)

A mixture of bromopyrrole 13-5 (0.40 g, 0.59 mmol), 3-pyridyl boronic acid 14-1 (0.14 g, 1.19 mmol) and aqueous $Na_2CO_3$ (0.31 g, 2.99 mmol) and $Pd(PPh_3)_4$ (0.13 g, 0.11 mmol in 1,4-dioxane (5 mL, degassed) was heated at 120° C. in microwave for 15 min. The reaction mixture was diluted with water (20 mL) extracted with EtOAc (2×50 mL). The combined organic layers were washed with brine solution (2×20 mL), dried over anhydrous $Na_2SO_4$, filtered and concentrated under reduced pressure. The residue was purified by combiflash column chromatography (silica gel; eluent: $MeOH/CH_2Cl_2$) to obtain intermediate 14-2 as pale yellow solid.

(S)—N-{2-(Aminomethyl)-5-chlorobenzyl}-1-{1-(hydroxymethyl)-4-(pyridin-3-yl)-1H-pyrrole-2-carbonyl) pyrrolidine-2-carboxamide (14-3)

A 50% solution of TFA in $CH_2Cl_2$ (4 mL) was added dropwise to a solution of Boc-amine 14-2 (0.14 g, 0.20 mmol) in $CH_2Cl_2$ (1 mL) and mixture was stirred at room temperature for 3 h. The solvent and volatiles were removed at reduced pressure to provide amine 14-3 as off-white solid.

(S)—N-{2-(Aminomethyl)-5-chlorobenzyl}-1-{4-(pyridin-3-yl)-1H-pyrrole-2-carbonyl}pyrrolidine-2-carboxamide (14-4)

A mixture of intermediate 14-3 (0.120 g, 0.25 mmol) and ammonia solution (7N solution in methanol; 2 mL) was stirred at room temperature for 2 h. The solvent and volatiles were removed at reduced pressure and residue was purified by combiflash column chromatography (silica gel: eluent: MeOH, $CH_2Cl_2$, $NH_4OH$) to obtain intermediate 14-4 as off-white solid.

(S)—N-{2-(Aminomethyl)-5-chlorobenzyl}-1-{4-(pyridin-3-yl)-1H-pyrrole-2-carbonyl}pyrrolidine-2-carboxamide (14-5)

Trifluoro acetic acid (0.005 mL, 0.07 mmol) was added dropwise to a solution of intermediate 14-4 (0.016 g, 0.03 mmol) in $CH_2Cl_2$ and mixture was at room temperature for 20 min. The solvent and volatiles were removed at reduced pressure, residue was stirred with diethyl ether (3 mL) for 5 min and filtered to obtain 14-5. $^1H$ NMR (MeOD-$d_4$, 400 $MH_z$) (δ) ppm: 9.03 (s, 1H), 8.64-8.62 (d, 1H), 8.53-8.52 (d, 1H), 7.85-30 (m, 6H), 4.57-4.54 (d, 2H), 4.36-4.38 (d, 2H), 4.29-4.27 (d, 2H), 4.04-4.01 (m, 2H), 2.32-2.27 (m, 1H), 2.16-2.08 (m, 1H), 2.13-2.00 (m, 1H), 1.99-1.94 (m, 1H).

EXAMPLE 15

Preparation of (S)—N-[{2-(Aminomethyl)-5-chlorobenzyl}-1-{4-(pyridin-2-yl)-1H-pyrrole-2-carbonyl}]pyrrolidine-2-carboxamide bis (2,2,2-trifluoroacetate) (15-8)

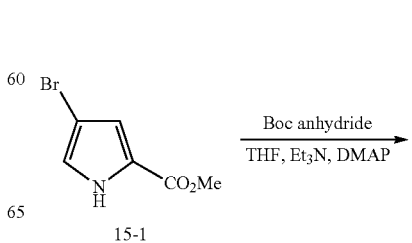

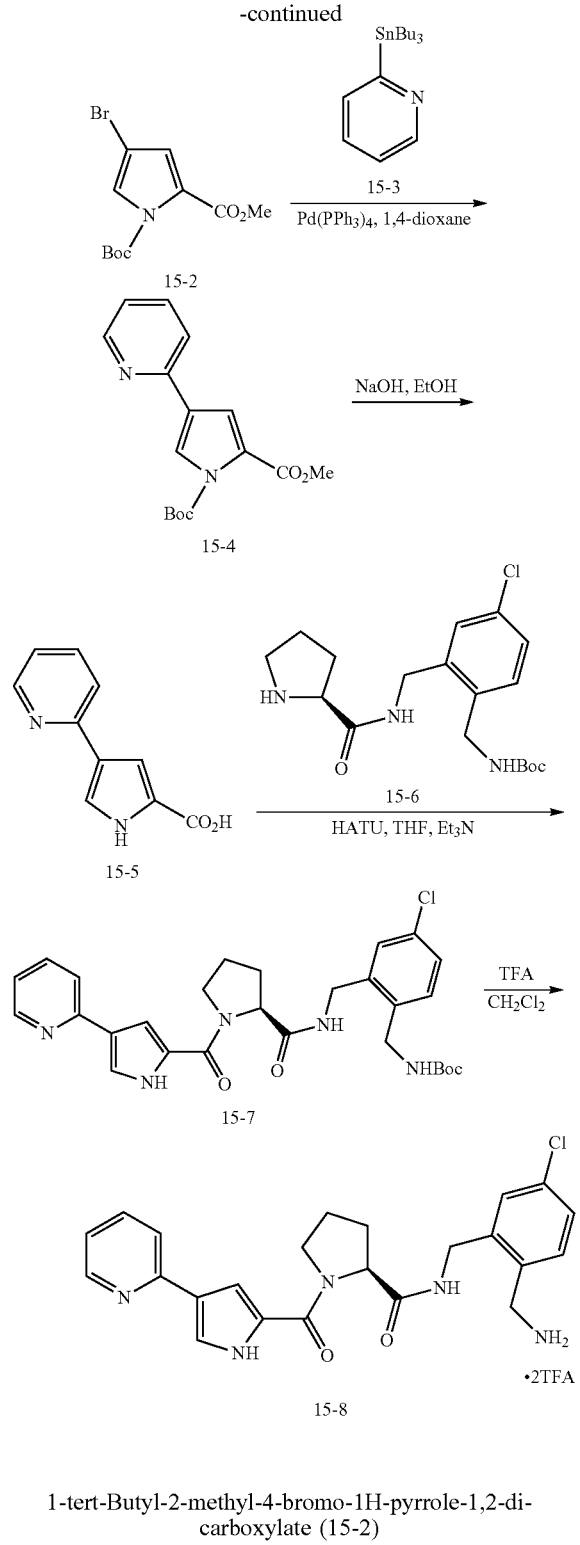

1-tert-Butyl-2-methyl-4-bromo-1H-pyrrole-1,2-dicarboxylate (15-2)

A solution of Boc anhydride (0.83 g, 3.82 mmol) in THF (3 mL) was added dropwise to the mixture of pyrrole 15-1 (0.65 g, 3.18 mmol), Et$_3$N (0.9 mL, 6.37 mmol) and DMAP (0.039 g, 0.31 mmol) in THF (5 mL) at 0° C. and mixture was stirred at room temperature for 16 h. The reaction was quenched by saturated aqueous NH$_4$Cl solution (50 mL) and extracted with ethyl acetate (2×50 mL). The combined organic extract was washed with water (30 mL), brine (30 mL), dried over anhydrous Na$_2$SO$_4$, filtered and concentrated under reduced pressure. The residue was purified by column chromatography (silica gel: eluent: 0-50% EtOAc/hexanes) to obtain Boc pyrrole 15-2 as colorless oil.

1-tert-Butyl-2-methyl 4-(pyridin-2-yl)-1H-pyrrole-1,2-dicarboxylate (15-4)

2-(Tributylstannyl)pyridine 15-3 (0.31 g, 0.723 mmol) and triethyl amine (0.18 mL, 1.32 mmol) was added to the degassed solution of bromo pyrrole 15-2 (0.2 g, 0.66 mmol) in 1,4 dioxane (2 mL). Pd(PPh$_3$)$_4$ (0.15 g, 0.13 mmol) was added to the mixture and reaction mixture was subjected to microwave irradiation at 120° C. for 1 h. The reaction mixture was diluted with water (25 mL) and extracted with EtOAc (2×50 mL). The combined organic layers was washed with brine (20 mL), dried over anhydrous Na$_2$SO$_4$, filtered and concentrated under reduced pressure. The residue was purified by column chromatography (silica gel; eluent: 0-30% EtOAc/hexanes) to obtain 15-4 as hygroscopic off-white solid.

4-(Pyridin-2-yl)-1H-pyrrole-2-carboxylic acid (15-5)

A solution of NaOH (0.046 g, 1.16 mmol) in water (1 mL) was added dropwise to a stirred solution of 15-4 (0.07 g, 0.23 mmol) in ethanol (2 mL) and reaction mixture was heated at 80° C. for 16 h. The mixture was cooled to room temperature and organic solvent was removed under reduced pressure. The residue was dissolved in water (10 mL), acidified with 1% aqueous citric acid solution to pH 4, and extracted with ethyl acetate (7×20 ml). The combined organic extract was dried over anhydrous Na$_2$SO$_4$, filtered and concentrated under reduced pressure to obtain acid 15-5 as off-white solid.

(S)-tert-Butyl-4-chloro-2-[{1-{4-(pyridin-2-yl)-1H-pyrrole-2-carbonyl}pyrrolidine-2-carboxamido}methyl]benzylcarbamate (15-7)

Triethyl amine (0.1 mL, 0.34 mmol) was added to the stirred solution of acid 15-5 (0.06 g, 0.32 mmol) amine 15-6 (0.23 g, 0.64 mmol) and HATU (0.13 g, 0.35 mmol) in THF (5 mL) and mixture was stirred at room temperature for 16 h. The reaction was quenched with 1% aqueous citric acid solution (20 mL) and extracted with ethyl acetate (2×50 mL). The combined organic extract was washed with saturated NaHCO$_3$ solution (20 mL), water (20 mL) and brine (20 mL). The organic layer was dried over anhydrous Na$_2$SO$_4$, filtered and concentrated under reduced pressure. The residue was purified by reverse phase column chromatography (C18; eluent: 10-80% acetonitrile/water) to obtain amide 15-7 as off-white solid.

(S)—N-[{2-(aminomethyl)-5-chlorobenzyl}-1-{4-(pyridin-2-yl)-1H-pyrrole-2-carbonyl}]pyrrolidine-2-carboxamide (15-8)

A mixture of amide 15-7 (0.05 g, 0.10 mmol), trifluoroacetic acid (0.2 mL, 2.61 mmol) in CH$_2$Cl$_2$ (2 mL) was stirred at room temperature for 1 h. The solvent and volatiles were removed at reduced pressure and triturated with diethyl ether. The solid was dissolved in water (3 mL) and lyophilized to obtain 15-8. $^1$H NMR (MeOD-d$_4$, 400 MHz) (δ) ppm: 8.55-8.56 (d, J=5.6 Hz, 1H), 8.31-8.35 (dd, J=7.6 Hz, J=7.2 Hz, 1H), 8.19-8.20 (d, J=8.0 Hz, 1H), 7.91 (s, 1H), 7.62-7.65 (t, J=6.8 Hz, 1H), 7.49 (s, 2H), 7.38-7.44 (m, 2H), 4.53-4.59 (m, 2H), 4.34-4.38 (d, J=8.0 Hz, 1H), 4.25 (s, 2H), 3.92-4.08 (m, 2H), 2.26-2.33 (m, 1H), 2.06-2.21 (m, 2H), 1.88-2.01 (m, 1H).

EXAMPLE 16

Preparation of (S)—N-{2-(aminomethyl)-5-chlorobenzyl}-1-{(S)-2-(hydroxymethyl)-3,3-dimethylbutanoyl}pyrrolidine-2-carboxamide-2,2,2-trifluoroacetate (16-9)

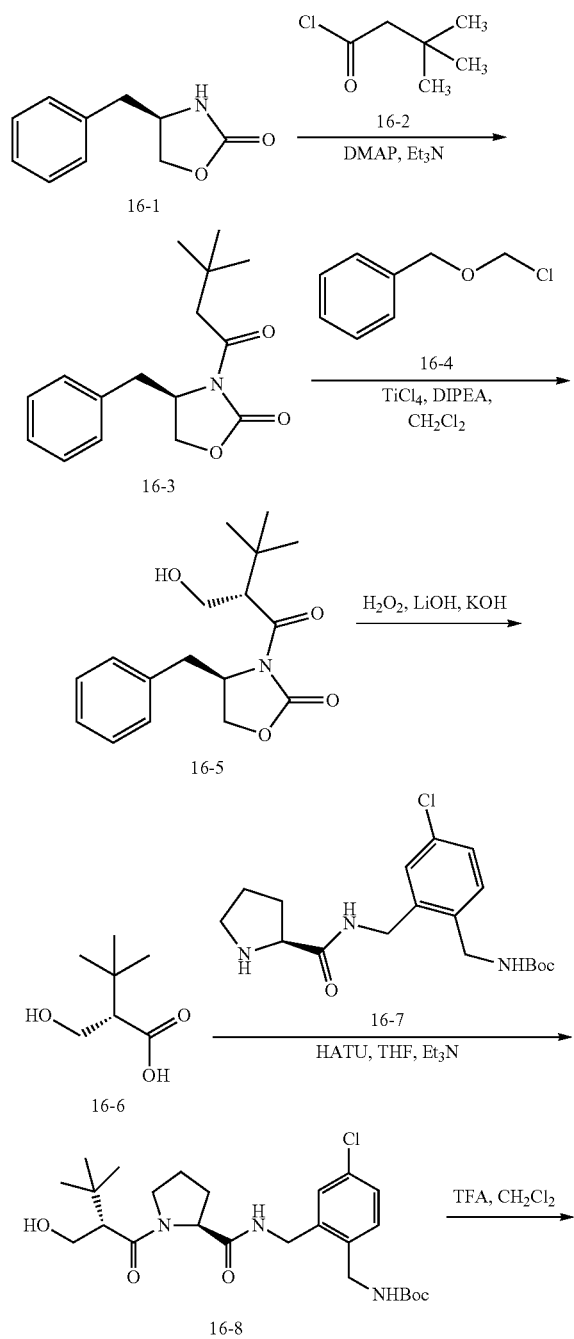

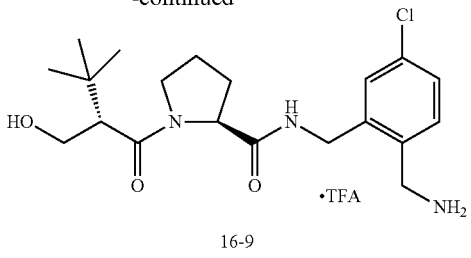

(R)-4-Benzyl-3-(3,3-dimethylbutanoyl)oxazolidin-2-one (16-3)

A solution of tert-butylacetyl chloride 16-2 (4.3 ml, 0.031 mol) in THF (25 ml) was added dropwise to a mixture of Benzyl-2-oxazolidinone 16-1 (5.0 g, 0.028 mol), triethylamine (8.7 ml, 0.062 mol) and DMAP (0.34 g, 0.0028 mol) in THF (25 ml) at 0° C. and the mixture was stirred at room temperature for 1 h. The reaction was quenched by water (100 mL) and extracted with EtOAc (3×100 mL). The combined organic extract was washed with 2M aqueous HCl (2×50 mL), water (2×100 mL), brine solution (100 mL), dried over Na$_2$SO$_4$ and concentrated under reduced pressure. The residue was purified by column chromatography (silica gel; eluent: EtOAc/hexanes 10-80%) to obtain 16-3 as a white solid.

(R)-4-Benzyl-3-{(S)-2-(hydroxymethyl)-3,3-dimethylbutanoyl}oxazolidin-2-one (16-5)

Titanium tetrachloride (4.8 g, 0.025 mol) was added drop wise to the solution of imide 16-3 (6.6 g, 0.024 mol) in CH$_2$Cl$_2$ (75 ml) at 0° C. and the mixture was stirred for 20 min. Thereafter, DIPEA (8.35 ml, 0.048 mmol) was added drop wise at 0° C. followed by addition of benzyl chloromethyl ether 16-4 (6.6 ml, 0.048 mol) after 5 min and mixture was stirred for 4 h. Reaction was quenched with saturated aqueous NH$_4$Cl solution (25 mL) and extracted with CHCl$_3$ (3×100 mL). The combined organic layer washed with water (2×100 mL), brine (50 mL) and dried over anhydrous Na$_2$SO$_4$, filtered and concentrated under reduced pressure. The residue was purified column chromatography (silica gel; eluent: 10-90% EtOAc/hexanes) to protected hydroxyl acid 16-5 as off-white solid.

(S)-2-(Hydroxymethyl)-3,3-dimethylbutanoic acid (16-6)

A 30% aqueous hydrogen peroxide (0.6 ml, 5.38 mmol) and lithium hydroxide (0.064 g, 2.69 mmol) was added to the solution of imide 16-5 (0.82 g, 2.69 mmol) in mixture of THF/water (3:1, 4 mL) at 0° C. and the mixture was stirred at room temperature for 16 h. Then aqueous potassium hydroxide solution (0.15 g in 0.75 ml water) was added and the mixture was heated under reflux for 3 h. Reaction mixture was cooled to room temperature, quenched with 10% aqueous sodium sulphite solution (20 ml) and washed with CH$_2$Cl$_2$ (2×100 mL). The aqueous layer was acidified to pH 2 using 1M aqueous HCl and extracted with chloroform (3×100 mL). The combined organic layer washed with water (2×100 mL) and brine (50 mL) and dried over anhydrous Na$_2$SO$_4$, filtered and concentrated under reduced pressure to hydroxyl acid 16-6 as off-white solid.

tert-Butyl-4-chloro-2-[{(S)-14(S)-2-(hydroxymethyl)-3,3-dimethylbutanoyl)pyrrolidine-2-carboxamido}methyl]benzylcarbamate (16-8)

Triethylamine (0.23 ml, 1.64 mmol) was added dropwise to the solution of acid 16-6 (0.08 g, 0.55 mmol), amine 16-7 (0.21 g, 0.55 mmol) and HATU (0.23 g, 0.603 mmol) in THF (5 ml) and mixture was stirred at room temperature for 16 h. The reaction was quenched by 1% aqueous citric acid solution (10 mL), diluted with water (50 mL) and extracted with EtOAc (3×50 mL). The combined organic extract was washed with saturated aqueous $NaHCO_3$ solution (2×50 mL), brine (50 mL), dried over anhydrous $Na_2SO_4$, filtered and concentrated under reduced pressure. The residue was purified by reverse phase column chromatography to give obtain 16-8 as off-white solid.

(S)—N-{2-(Aminomethyl)-5-chlorobenzyl}-1-{(S)-2-(hydroxymethyl)-3,3-dimethylbutanoyl}pyrrolidine-2-carboxamide (16-9)

Trifluoroacetic acid (0.3 mL, 3.91 mmol) was added to the solution of Boc protected amine 16-8 (0.11 g, 0.22 mmol) in $CH_2Cl_2$ (1 mL), and reaction mixture was stirred at room temperature for 1 h. The solvent and volatiles were removed at reduced pressure and residue was dried under high vacuum. The crude product was purified by reverse phase combiflash column chromatography (C18; eluent: acetonitrile:water) to obtain 16-9. $^1$H NMR (MeOD-d$_4$, 400 MHz) (δ) ppm: 7.35-7.46 (m, 3H), 4.33-4.46 (m, 3H), 4.19-4.27 (dd, J=13.6 Hz, J=3.6 Hz, 2H), 3.65-3.89 (m, 4H), 2.79-2.83 (dd, J=10.4, J=4.4 Hz, 1H), 2.19-2.24 (m, 1H), 1.93-2.01 (3H, m), 0.99 (9H, s).

EXAMPLE 17

Preparation of (S)—N-{5-Chloro-2-(hydroxymethyl)benzyl}-1-{(R)-2-hydroxy-3,3-dimethylbutanoyl}pyrrolidine-2-carboxamide (17-5)

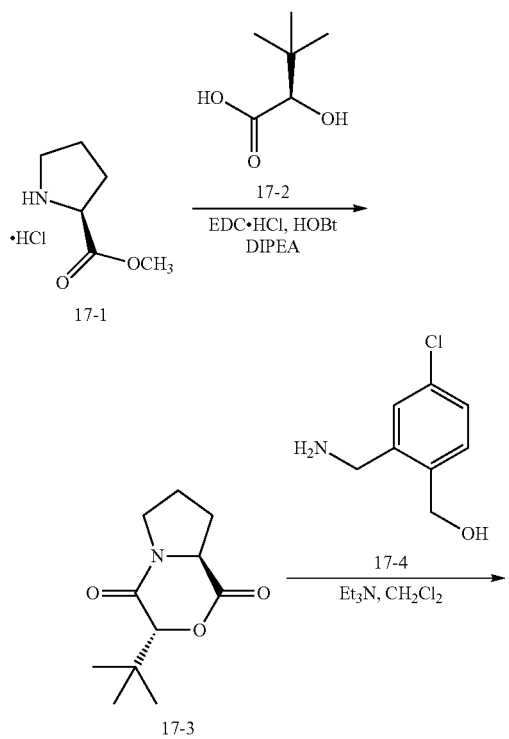

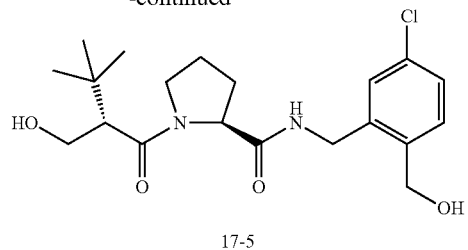

(3R,8aS)-3-(tert-Butyl)-tetrahydro-1H-pyrrolo[2,1-c][1,4]oxazine-1,4(3H)-dione (17-3)

A mixture of (S)-methyl pyrrolidine-2-carboxylate hydrochloride 17-1 (0.25 g, 1.51 mmol), (R)-2-hydroxy-3,3-dimethylbutanoic acid 17-2 (0.22 g, 1.66 mmol), EDCI.HCl (0.37 g, 1.96 mmol) and HOBt (0.20 g, 1.51 mmol) and Et$_3$N (0.42 mL, 3.02 mmol) in DMF (3 mL) was stirred under nitrogen at room temperature for 1 h. The reaction mixture was diluted with water (5 mL) and extracted with EtOAc (2×25 mL). The combined organic layer was washed with brine (20 mL), dried over $Na_2SO_4$ and concentrated under reduced pressure and the residue was purified by reverse phase flash chromatography (silica gel; eluent: 0%-50% EtOAc/hexanes) to afford lactone 17-3 as light yellow solid.

(S)—N-{5-Chloro-2-(hydroxymethyl)benzyl}-1-{(R)-2-hydroxy-3,3-dimethyl butanoyl}pyrrolidine-2-carboxamide (17-5)

Amine 17-4 (0.17 g, 1.02 mmol) was added to the mixture of lactone 17-3 (0.18 g, 0.85 mmol) and Et$_3$N (3 mL) in $CH_2Cl_2$ (3 mL) and mixture was stirred under nitrogen at room temperature for 48 h. The reaction was quenched with water (5 mL) and extracted with $CH_2Cl_2$ (3×50 mL). The combined organic layer was washed with brine (15 mL), dried over $Na_2SO_4$ and concentrated under reduced pressure. The residue was purified by reverse phase flash chromatography (C18; eluent: 10%-40% acetonitrile:water) to afford 17-5. $^1$H NMR (DMSO-d$_6$, 400 MH$_Z$) (δ) ppm: 8.27-8.45 (m, 1H), 7.26-7.39 (m, 3H), 5.18-5.20 (t, J=8.0 Hz, 1H), 4.64-4.66 (d, J=8.0 Hz, 1H), 4.50-4.55 (m, 2H), 4.26-4.33 (m, 3H), 3.89-3.91 (d, J=8.0 Hz, 1H), 3.63-3.70 (m, 2H), 1.74-2.07 (m, 4H), 0.92 (s, 9H).

EXAMPLE 18

Preparation of (5)-N-{2-(Aminomethyl)-5-chlorobenzyl}-1-(6-oxo-1,6-dihydropyridine-2-carbonyl)pyrrolidine-2-carboxamide-2,2,2-trifluoroacetate (18-4)

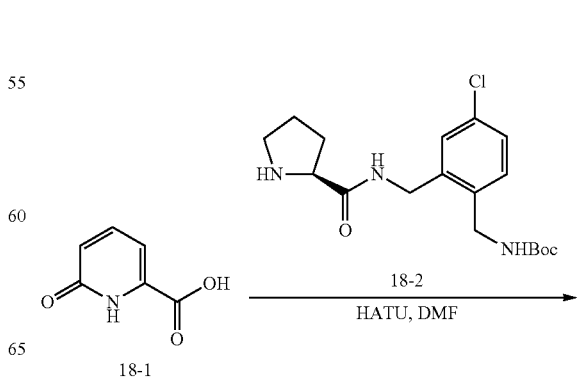

75

-continued

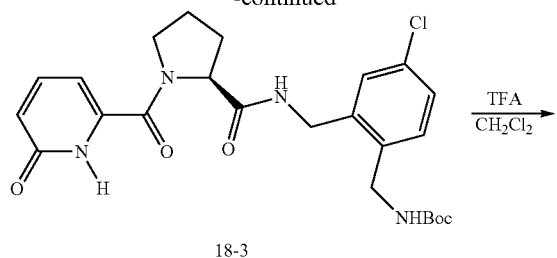

18-3

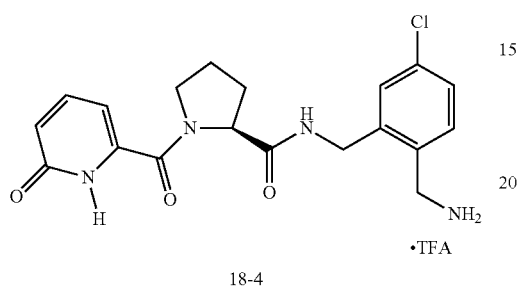

18-4

(S)-tert-Butyl-4-chloro-2-[{1-(6-oxo-1,6-dihydro-pyridine-2-carbonyl) pyrrolidine-2-carboxamido}methyl]benzylcarbamate (18-3)

The mixture of acid 18-1 (39.8 mg, 0.28 mmol), amine 18-2 (0.10 g, 0.28 mmol), HATU (0.11 g, 0.30 mmol) and Et$_3$N (0.1 mL, 0.82 mmol) in DMF (2 mL) was stirred at room temperature for 2 h. The reaction mixture was quenched with water (20 mL) and extracted with EtOAc (3×25 mL). The combined organic extracts was washed with aqueous saturated NaHCO$_3$ solution (20 mL) and 1N aqueous HCl (20 mL), brine solution (20 mL), dried over anhydrous Na$_2$SO$_4$, filtered and concentrated under reduced pressure. The residue was purified by silica gel column chromatography (eluent: 70% EtOAc/hexanes) to get amide 18-3 as a light brown solid.

(S)—N-{2-(Aminomethyl)-5-chlorobenzyl}-1-(6-oxo-1,6-dihydropyridine-2-carbonyl) pyrrolidine-2-carboxamide-2,2,2-trifluoroacetate (18-4)

Trifluoroacetic acid (50% solution in CH$_2$Cl$_2$, 2 mL) was added to Boc protected amine 18-3 (75.0 mg, 0.15 mmol) in CH$_2$Cl$_2$ (1 mL) and reaction was stirred at 0° C. for 2 h. The reaction mixture was concentrated under reduced pressure and residue by reverse phase combiflash chromatography (C18; 10-100% acetonitrile/water) to get 18-4. $^1$H NMR (MeOD-d$_4$, 400 MHz) (δ) ppm: 7.12-7.67 (m, 4H), 6.34-6.80 (m, 2H), 4.63-4.67 (d, J=16 Hz, 1H), 4.46-4.49 (t, J=12 Hz, 1H), 4.18-4.33 (m, 3H), 3.69-3.79 (m, 2H), 2.30-2.36 (m, 1H), 1.92-2.09 (m, 3H).

76

EXAMPLE 19

Preparation of (2S)-N-{2-(Aminomethyl)-5-chlorobenzyl}-1-(5-hydroxy-6,7-dihydro-5H-cyclopenta[b]pyridine-5-carbonyl}pyrrolidine-2-carboxamide-2,2,2-trifluoroacetate (19-4)

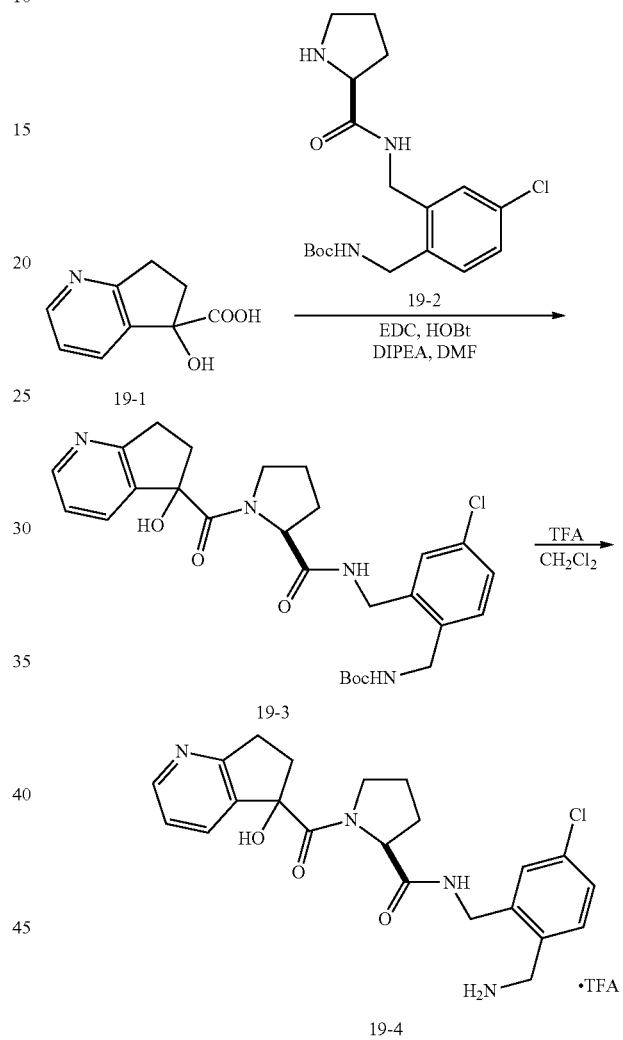

tert-Butyl-4-chloro-2-[{(2S)-1-(5-hydroxy-6,7-dihydro-5H-cyclopenta[b]pyridine-5-carbonyl)pyrrolidine-2-carboxamido}methyl]benzylcarbamate (19-3)

A mixture of acid 19-1* (0.40 g, 2.2 mmol), amine 19-2 (0.82 g, 2.2 mmol), EDC (0.85 g, 4.4 mmol) and HOBt (0.30 g, 2.2 mmol) in DMF (10 mL) was stirred at room temperature for 16 h. The mixture was diluted with water (30 mL) and extracted with EtOAc (3×20 mL). The combined organic extract was washed with water (2×30 mL), brine (30 mL), dried over anhydrous Na$_2$SO$_4$, filtered and concentrated under reduced pressure. The residue was purified by reverse phase combiflash (C18: 10-100% acetonitrile/water) to obtain amide 19-3 as white solid.

(2S)-N-{2-(Aminomethyl)-5-chlorobenzyl}-1-(5-hydroxy-6,7-dihydro-5H-cyclopenta[b]pyridine-5-carbonyl)pyrrolidine-2-carboxamide-2,2,2-trifluoroacetate (19-4)

A 50% solution of TFA (5 mL) was added to the solution of amide 19-3 (0.12 g, 0.22 mmol) in CH$_2$Cl$_2$ (1 mL) and reaction mixture was stirred at room temperature for 3 h. The solvent was removed at reduced pressure and residue was azeotroped with toluene (2×20 mL) and purified by reverse phase combiflash (C18; 30% acetonitrile/water) to provide 19-4 as white solid. $^1$H NMR (MeOD, 300 MH$_Z$) (δ) ppm (mixture of diastereomers): 8.59 (s, 1H), 7.33-8.21 (m, 5H), 4.52-4.68 (m, 1H), 4.39-4.49 (m, 2H), 4.19-4.34 (m, 3H), 3.90-4.19 (m, 1H), 3.70-3.76 (m, 1H), 3.14-3.25 (m, 1H), 2.69-2.88 (m, 1H), 2.16-2.54 (m, 2H), 1.81-2.17 (m, 4H).

*Acid 19-1 was prepared according to procedure described in Example 26.

EXAMPLE 20

Preparation of (2S)-N-(2-(Aminomethyl)-5-chlorobenzyl)-1-(7-hydroxy-6,7-dihydro-5H-cyclopenta[b]pyridine-7-carbonyl)pyrrolidine-2-carboxamide-bis(2,2,2-trifluoroacetate) (20-8)

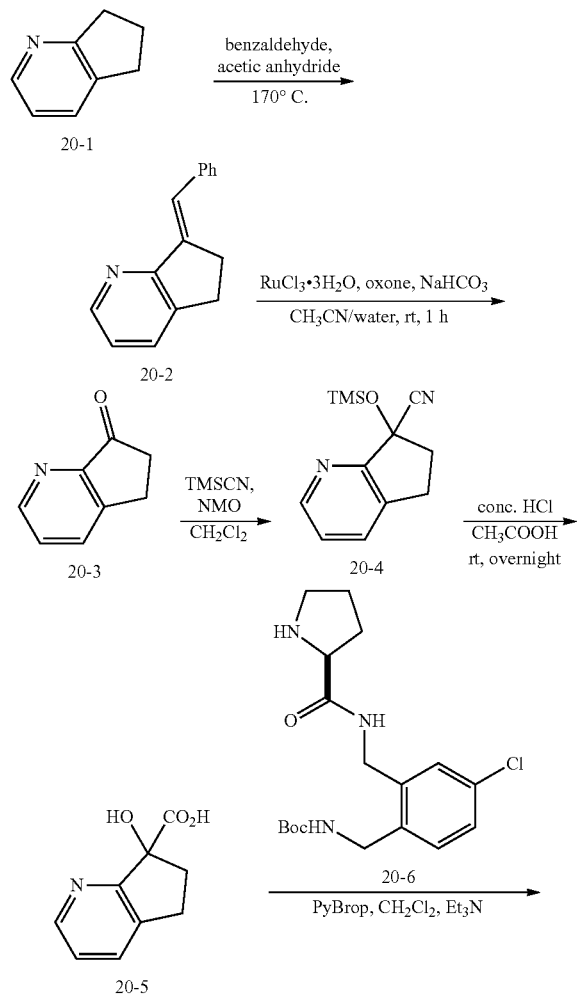

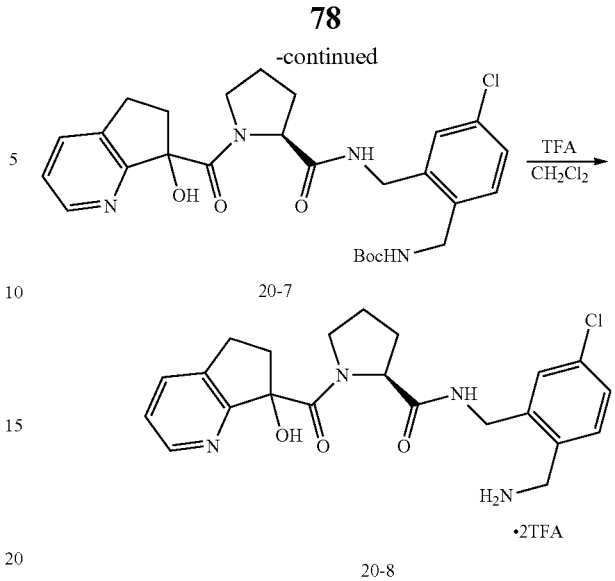

(E)-7-Benzylidene-6,7-dihydro-5H-cyclopenta[b]pyridine (20-2)

The mixture 2,3-cyclopenteno pyridine 20-1 (5.0 g, 42.01 mmol), benzaldehyde (6.75 mL, 63.86 mmol) and acetic anhydride (8 mL) was refluxed at 170° C. for 15 h under nitrogen. The solvent and volatile byproduct were removed at reduced pressure and the residue was purified by flash chromatography (silica gel; 0-5% EtOAc/hexanes) to afford alkene 20-2 as brown solid.

5H-Cyclopenta[b]pyridin-7(6H)-one (20-3)

A solution of RuCl$_3$.H$_2$O (0.264 g, 1.014 mmol) in CH$_3$CN/water (15 mL; 1:2) was added to the stirred solution of alkene 20-2 (6.0 g, 28.98 mmol) in CH$_3$CN (450 mL). Thereafter, a mixture of oxone (26.7 g, 43.47 mmol) and NaHCO$_3$ (0.373 g, 4.44 mmol) was added in portions over a period of 15 min. Reaction mixture was stirred at room temperature for 1 h. The mixture was quenched by saturated Na$_2$SO$_3$ solution (200 mL) and extracted with CH$_2$Cl$_2$ (2×250 mL). The combined organic layers were washed with water (200 mL), brine (200 mL) and dried over anhydrous Na$_2$SO$_4$, filtered and concentrated under reduced pressure to afford ketone 20-3 as light green solid.

7-{(Trimethylsilyl)oxy}-6,7-dihydro-5H-cyclopenta[b]pyridine-7-carbonitrile (20-4)

NMO (0.66 g, 5.63 mmol) and TMSCN (3.7 mL, 28.16 mmol) was added to the solution of ketone 20-3 (2.5 g, 18.77 mmol) in CH$_2$Cl$_2$ (25 mL) and mixture was stirred at room temperature for 1 h. The reaction was quenched with saturated aqueous NH$_4$Cl solution (20 mL) and extracted with CH$_2$Cl$_2$ (2×50 mL). The combined organic layers were washed with water (50 mL), brine (50 mL) and dried over Na$_2$SO$_4$, filtered and concentrate at reduced pressure. The residue was purified by flash chromatography (silica gel; eluent: 0-10% EtOAc/hexanes) to afford TMS protected cyanohydrin 20-4 as colorless oil.

7-Hydroxy-6,7-dihydro-5H-cyclopenta[b]pyridine-7-carboxylic acid (20-5)

To a stirred solution of cyanohydrin 20-4 (0.5 g, 2.15 mmol) in AcOH (1 mL), was added conc. HCl (1.5 mL) and mixture was stirred at room temperature for 16 h. The solvent and volatiles were removed at reduced pressure and residue was azeotroped with toluene (15 mL). The crude solid was washed with EtOAc (15 mL) and CH$_2$Cl$_2$ (15 mL) to afford acid hydroxyl acid 20-5 as white hygroscopic solid.

tert-Butyl-4-chloro-2-[{(2S)-1-(7-hydroxy-6,7-di-hydro-5H-cyclopenta[b]pyridine-7-carbonyl)pyrrolidine-2-carboxamido}methyl]benzylcarbamate (20-7)

PyBrOP (0.508 g, 1.089 mmol) was added in portions to the mixture of amine 20-6 (0.2 g, 0.544 mmol), acid 20-5 (0.23 g, 1.089 mmol), and triethyl amine (0.45 mL, 3.269 mmol) in CH$_2$Cl$_2$ (5 mL) at 0° C. The mixture was stirred at room temperature for 2 h at room temperature. The reaction was quenched with aqueous saturated NaHCO$_3$ solution (20 mL) and extracted with CH$_2$Cl$_2$ (2×20 mL). The combined organic layers were washed with water (15 mL), brine (15 mL) and dried over anhydrous Na$_2$SO$_4$, filtered amd concentrate at reduced pressure. The residue was purified by reverse phase flash chromatography (C18; eluent: 10%-40% water/acetonitrile) to afford Boc protected amide 20-7 as white solid.

(2S)-N-{2-(Aminomethyl)-5-chlorobenzyl}-1-(7-hydroxy-6,7-dihydro-5H-cyclopenta[b]pyridine-7-carbonyl}pyrrolidine-2-carboxamide-bis-2,2,2-trifluoroacetate (20-8)

A 50% solution of TFA in CH$_2$Cl$_2$ (2 mL) was added to the solution of Boc protected amine 20-7 (0.07 g, 0.163 mmol) in CH$_2$Cl$_2$ (1 mL) and reaction mixture was stirred under at room temperature for 1 h. The solvent and volatiles were removed at reduced pressure and the residue was azeotroped with toluene (5 mL). The solid was washed with ether (2×5 mL), filtered and dried under high vacuum to afford 20-8. $^1$H NMR (MeOD-d$_4$, 300 MHz) (δ) ppm: 8.51 (d, J=5.1 Hz, 1H), 8.08 (d, J=7.81 Hz, 1H), 7.36-7.61 (m, 3H), 4.32-4.51 (m, 3H), 4.13-4.29 (m, 3H), 3.52-3.60 (m, 1H), 3.17-3.23 (m, 1H), 2.98-3.11 (m, 1H), 2.80-2.89 (m, 1H), 2.34-2.41 (m, 1H), 2.19-2.25 (m, 2H), 1.81-2.04 (m, 3H).

EXAMPLE 21

Preparation of (2S)-N-{2-(Aminomethyl)-5-chlorobenzyl}-1-(1,3-dihydroisobenzofuran-1-carbonyl)pyrrolidine-2-carboxamide-2,2,2-trifluoroacetate (21-6)

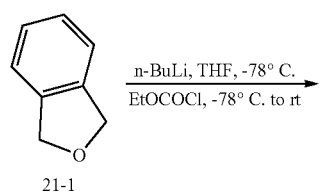

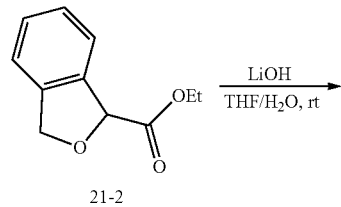

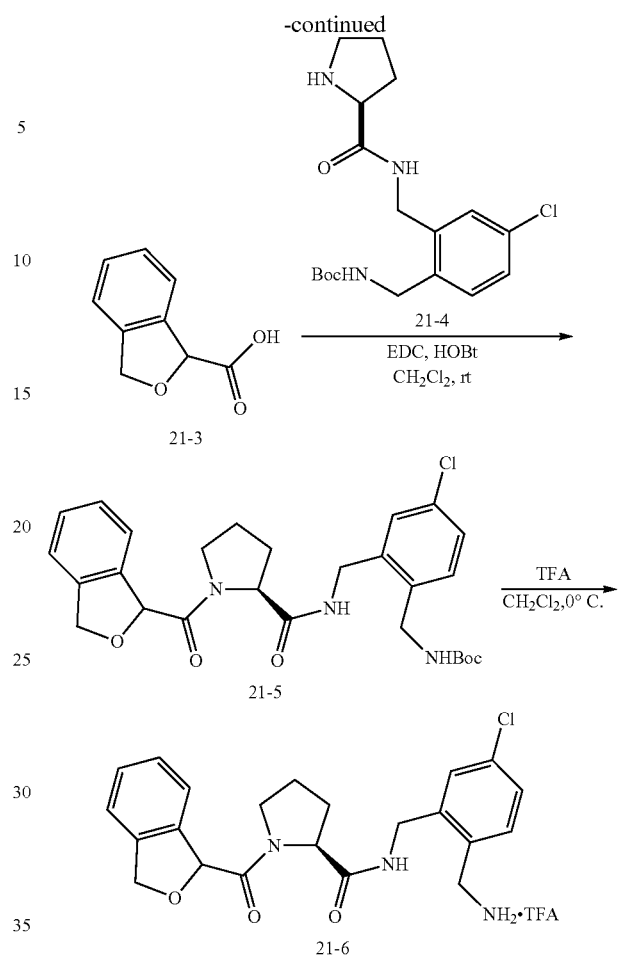

Ethyl-1,3-dihydroisobenzofuran-1-carboxylate (21-2)

A 2M solution of n-BuLi in cyclohexane (10 mL, 20.0 mmol) was added to a stirred solution of 1,3-dihydroisobenzofuran 21-1 (2.0 g, 16.7 mmol) in anhydrous THF (50 mL) at −78° C. and reaction mixture was stirred at same temperature for 2 h. Ethylchloroformate (3.2 mL, 33.4 mmol) was added dropwise to the mixture. The reaction was slowly allowed to warm to room temperature over a period of 15 h and was quenched with water (20 mL). The solvent was removed under reduced pressure and the residue was extracted with EtOAc (3×50 mL). The organic layer was washed with brine solution (50 mL), dried over anhydrous Na$_2$SO$_4$, filtered and concentrated under reduced pressure. The residue was purified by column chromatography (silica: eluent: 15% EtOAc/Hexanes) to provide ester 21-2 as yellow oil.

1,3-Dihydroisobenzofuran-1-carboxylic acid (21-3)

A solution of LiOH•H$_2$O (0.72 g, 18.48 mmol) in water (3 mL) was added to the solution of ester 21-2 (0.71 g, 3.70 mmol) in THF (3 mL) and MeOH (2 mL) at 0° C. and reaction mixture was stirred at room temperature for 16 h. Solvent was removed at reduced pressure and obtained residue was dissolved in water (10 mL) and acidified with 2M aqueous HCl to pH 4-5. The aqueous layer was extracted with EtOAc (3×20 mL). The combined organic layer was dried over anhydrous Na$_2$SO$_4$, filtered and concentrated under reduced pressure. The residue was purified by reverse phase combiflash chromatography (C18; 10-100% acetonitrile/water) to get acid 21-3 as a pale yellow solid.

tert-Butyl-4-chloro-2-[{(2S)-1-(1,3-dihydroisobenzofuran-1-carbonyl)pyrrolidine-2-carboxamido}methyl]benzylcarbamate (21-5)

Amine 21-4 (0.33 g, 0.91 mmol) was added to a solution of acid 21-3 (0.15 g, 0.91 mmol), EDCI (0.34 g, 1.82 mmol), HOBt (0.24 g, 1.82 mmol), and DIPEA (0.30 mL, 1.82 mmol) in CH$_2$Cl$_2$ (2 mL) at 0° C. and the reaction mixture was stirred for 5 h at room temperature. The reaction mixture was diluted with CH$_2$Cl$_2$ (20 mL), washed with saturated NaHCO$_3$ solution (20 mL) and 0.5M aqueous HCl (10 mL) successively. The organic layer was separated and washed with brine solution (10 mL), dried over anhydrous Na$_2$SO$_4$, filtered and concentrated under reduced pressure. The residue was purified by column chromatography (silica gel; 50% EtOAc/hexanes) to get amide 21-5 as pale yellow semi solid.

(2S)-N-(2-(Aminomethyl)-5-chlorobenzyl)-1-(1,3-dihydroisobenzofuran-1-carbonyl)pyrrolidine-2-carboxamide-2,2,2-trifluoroacetate (21-6)

A 50% solution of trifluoroacetic acid (4 mL) was added to the solution of Boc protected amine 21-5 (0.22 g, 0.42 mmol) in CH$_2$Cl$_2$ (1 mL) and mixture was stirred at 0° C. for 30 min. The reaction mixture was concentrated under reduced pressure and residue was triturated with diethyl ether to afford amine salt 21-6. $^1$HNMR (DMSO-d$_6$, 1:1 mixture of diastereomers, 400 MHz) (δ) ppm: 8.57-8.52 (m, 1H), 8.17 (bs, 3H), 7.45-7.27 (m, 7H), 5.88-5.87 (m, 1H), 5.22-5.07 (m, 2H), 4.41-4.25 (m, 3H), 4.18-4.07 (m, 2H), 3.88-3.60 (m, 2H), 2.13-2.08 (m, 1H), 2.03-1.89 (m, 2H), 1.81-1.68 (m, 1H).

EXAMPLE 22

(2S)-N-{2-(Aminomethyl)-5-chlorobenzyl}-1-(2,2-dioxido-1,3-dihydrobenzo[a]thiophene-1-carbonyl)pyrrolidine-2-carboxamide-2,2,2-trifluoroacetate-2,2,2-trifluoroacetate (22-10)

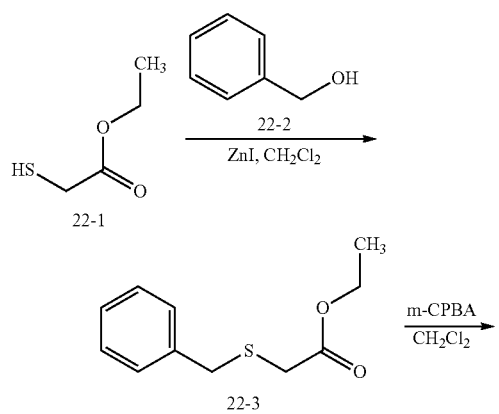

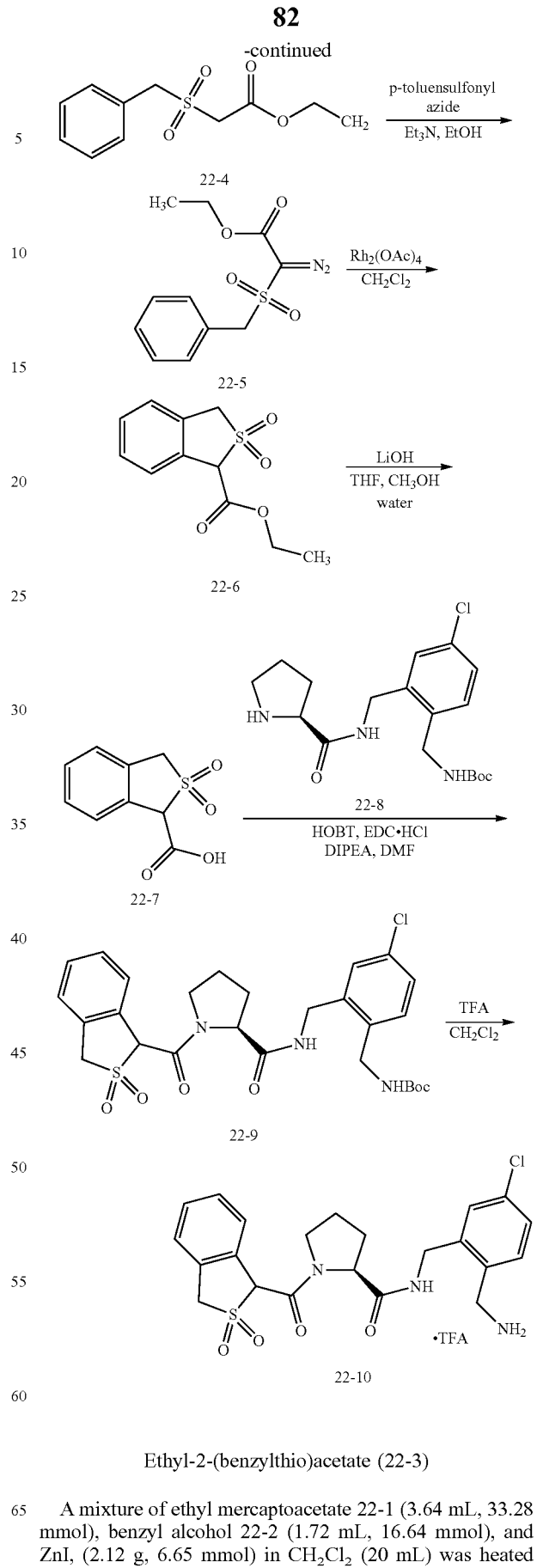

Ethyl-2-(benzylthio)acetate (22-3)

A mixture of ethyl mercaptoacetate 22-1 (3.64 mL, 33.28 mmol), benzyl alcohol 22-2 (1.72 mL, 16.64 mmol), and ZnI$_2$ (2.12 g, 6.65 mmol) in CH$_2$Cl$_2$ (20 mL) was heated under reflux for 3 h. The reaction mixture was diluted with CH₂Cl₂ (80 mL), washed with water (3×50 mL), brine (50 mL), dried over anhydrous Na₂SO₄, filtered and concentrated under reduced pressure to obtain 22-3 as a colorless oil.

Ethyl-2-(benzylsulfonyl)acetate (22-4)

To a solution of 22-3 (0.20 g, 0.95 mmol) in CH₂Cl₂ (5 mL) was added m-CPBA (0.41 g, 2.38 mmol) at 0° C. The reaction mixture was warmed to room temperature and stirred for 14 h. The solvent was removed under reduced pressure and residue was dissolved in EtOAc (25 mL), washed with 10% aqueous solution of Na₂SO₃ (2×20 mL), saturated solution of NaHCO₃ (2×20 mL), brine solution (20 mL), dried over anhydrous Na₂SO₄, filtered and concentrated under reduced pressure. The residue was by purified by combiflash column chromatography (silica gel: 0-20% EtOAc/hexanes) to obtain sulfone 22-4 as off-white solid.

Ethyl-2-(benzylsulfonyl)-2-diazoacetate (22-5)

A mixture of sulfone 22-4 (0.13 g, 0.55 mmol), p-toluene sulfonylazide (0.12 g, 0.60 mmol), and triethyl amine (0.15 mL, 1.1 mmol) in EtOH (3 mL) was stirred at room temperature for 5 h. The solvent was removed under reduced pressure, residue was dissolved in EtOAc (25 mL) and washed with 5% aqueous NaOH solution (2×20 mL), water (2×20 mL), brine solution (20 mL). The organic layer was dried over anhydrous Na₂SO₄, filtered and concentrated under reduced pressure. The residue was purified by combiflash column chromatography (silica gel: 0-25% CH₂Cl₂/MeOH) to obtain diazoacetate 22-5 as off white solid.

Ethyl-1,3-dihydrobenzo[a]thiophene-1-carboxylate-2,2-dioxide (22-6)

Rhodium acetate (0.005 g, 0.01 mmol) was added to a solution of diazoacetate 5 (0.058 g, 0.216 mmol) in CH₂Cl₂ (2 mL) and mixture was stirred at room temperature for 2 h. The reaction mixture was filtered through pad of celite and washed with CH₂Cl₂ (2×25 mL). The filtrate was concentrated under reduced pressure and residue was purified by combiflash column chromatography (silica gel; 0-30% EtOAc/hexanes) to obtain dihydrobenzo[a]thiophene 22-6 as off white solid.

1,3-Dihydrobenzo[a]thiophene-1-carboxylicacid-2,2-dioxide (22-7)

A solution of LiOH•H₂O (7 mg, 0.31 mmol) in water (0.5 mL) was added to a solution of intermediate 22-6 (0.025 g, 0.10 mmol) in THF/MeOH (1 mL, 3:2) was added and stirred at room temperature for 14 h. The solvent was removed under reduced pressure, mixture was diluted with water (10 mL). The aqueous solution was washed with MTBE (10 mL), acidified with 2M aqueous HCl to pH 4-5 and extracted with EtOAc (3×25 mL). The combined organic layer was dried over anhydrous Na₂SO₄, filtered and concentrated under reduced pressure. The residue was purified by reverse phase combiflash chromatography (C18; 10-100% acetonitrile/water) to provide acid 22-7.

tert-Butyl-4-chloro-2-[{(2S)-1-(2,2-dioxido-1,3-dihydrobenzo[a]thiophene-1-carbonyl)pyrrolidine-2-carboxamido}methyl]benzylcarbamate (22-9)

A mixture of acid 7 (0.04 g, 0.19 mmol), amine 22-8 (0.076 g, 0.21 mmol), HOBT (0.025 g, 0.19 mmol), EDC•HCl (0.108 g, 0.56 mmol) and DIPEA (0.065 mL, 0.38 mmol) in anhydrous DMF (3 mL) was stirred under nitrogen at room temperature for 16 h. The reaction mixture was quenched with water (10 mL), diluted with EtOAc (25 mL) and washed with saturated NaHCO₃ aqueous solution (25 mL), brine solution (25 mL). The organic layer was separated, dried over anhydrous Na₂SO₄, filtered and concentrated. The residue was purified by combiflash column chromatography (silica gel; eluent: 0-20% EtOAc/hexanes) to obtain amide 22-9.

(2S)-N-{2-(Aminomethyl)-5-chlorobenzyl}-1-(2,2-dioxido-1,3-dihydrobenzo[a]thiophene-1-carbonyl)pyrrolidine-2-carboxamide-2,2,2-trifluoroacetate 2,2,2-trifluoroacetate (22-10)

Trifluoro acetic acid (0.50 mL, 6.50 mmol) was added to a solution of 22-9 (0.045 g, 0.08 mmol) in CH₂Cl₂ (1 mL) and reaction mixture was stirred at room temperature for 2 h. The solvent and volatiles were removed under reduced pressure and the residue was purified by reverse phase combiflash column chromatography (C18; eluent: 10-100% acetonitrile/water) to obtain 22-10.
¹H NMR (MeOD-d₄, 400 MH$_Z$) (δ) ppm: 7.51 (1H, s), 7.47-7.51 (d, J=16 Hz, 2H), 7.35-7.45 (m, 4H), 4.37-4.54 (m, 5H), 4.21-4.22 (d, J=4 Hz, 2H), 3.66-3.71 (m, 2H), 3.18-3.20 (d, J=8.0 Hz, 1H), 2.24-2.27 (m, 1H), 1.94-2.04 (m, 3H).

EXAMPLE 23

Preparation of (2S)-N-{2-(Aminomethyl)-5-chlorobenzyl}-1-(isoindoline-1-carbonyl)pyrrolidine-2-carboxamide bis(2,2,2-trifluoroacetate) (23-4)

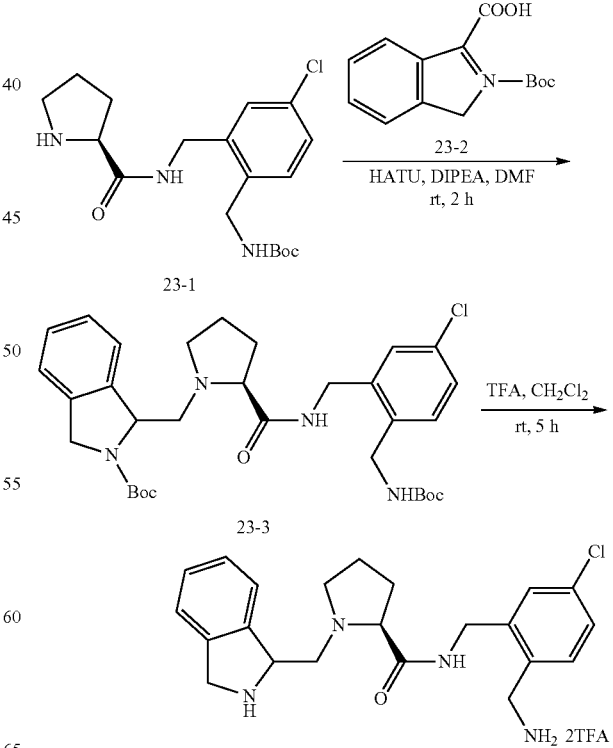

tert-Butyl-1-[(S)-2-{(2-[{(tert-butoxycarbonyl)amino}methyl]-5-chlorobenzyl)carbamoyl}pyrrolidine-1-carbonyl]isoindoline-2-carboxylate (23-2)

A mixture of acid 23-2 (1.0 g, 3.8 mmol), amine 23-1 (1.39 g, 3.8 mmol), HATU (2.9 g, 7.6 mmol), DIPEA (2 mL, 11.4 mL) in anhydrous DMF (25 mL) was stirred under nitrogen at room temperature for 2 h. The reaction mixture was diluted with EtOAc (100 mL) and washed with saturated aqueous NaHCO$_3$ solution (2×50 mL), brine solution (100 mL). The organic layer was separated, dried over anhydrous Na$_2$SO$_4$, filtered and concentrated under reduced pressure. The residue was purified by reverse phase combiflash column chromatography (C18; eluent: 10-100% acetonitrile:water) to afford amide 23-3.

(2S)-N-{2-(Aminomethyl)-5-chlorobenzyl}-1-(isoindoline-1-carbonyl) pyrrolidine-2-carboxamide bis (2,2,2-trifluoroacetate) (23-4)

Trifluoro acetic acid (8 mL, 104 mmol) was added to the solution of amide 23-3 (1.8 g, 2.94 mmol) in CH$_2$Cl$_2$ (20 mL), and reaction mixture was stirred at room temperature for 5 h. The volatiles were removed at reduced pressure and residue was purified by reverse phase combiflash column chromatography (C18; eluent: 10-100% acetonitrile:water) to obtain polar diastereomer 23-4a and non polar diastereomer 23-4b.

23-4a: $^1$H NMR (DMSO-d$_6$, 400 MHz) (δ) ppm: 10.10-8.01 (m, 5H), 7.55-7.25 (m, 7H), 5.86 (s, 1H), 4.73-4.52 (m, 3H), 4.37-4.29 (m, 2H), 4.03 (s, 2H), 3.95-3.85 (m, 2H), 2.24-1.86 (m, 4H).

23-4b: $^1$H NMR (MeOD-d$_4$, 400 MHz) (δ) ppm: 7.49-7.39 (m, 7H), 5.95 (s, 1H), 4.78 (s, 1H), 4.66 (dd, J=28.4, 14 Hz, 2H), 4.44 (dd, J=8.4, 4.4 Hz, 1H), 4.37 (d, J=15.2 Hz, 1H), 4.24 (s, 2H), 4.03 (t, J=6.4 Hz, 2H), 2.41-2.36 (m, 1H), 2.19-2.15 (m, 2H), 2.05-1.99 (m, 1H).

EXAMPLE 24

Preparation of (2S)-N-{2-(Aminomethyl)-5-chlorobenzyl}-1-(2,3-dihydrobenzofuran-3-carbonyl)pyrrolidine-2-carboxamide-2,2,2-trifluoroacetate (24-8)

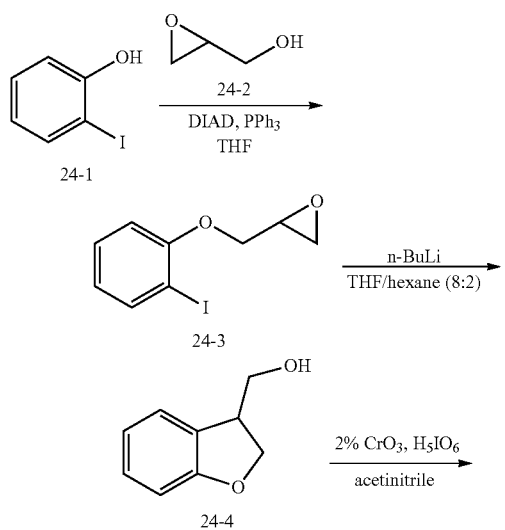

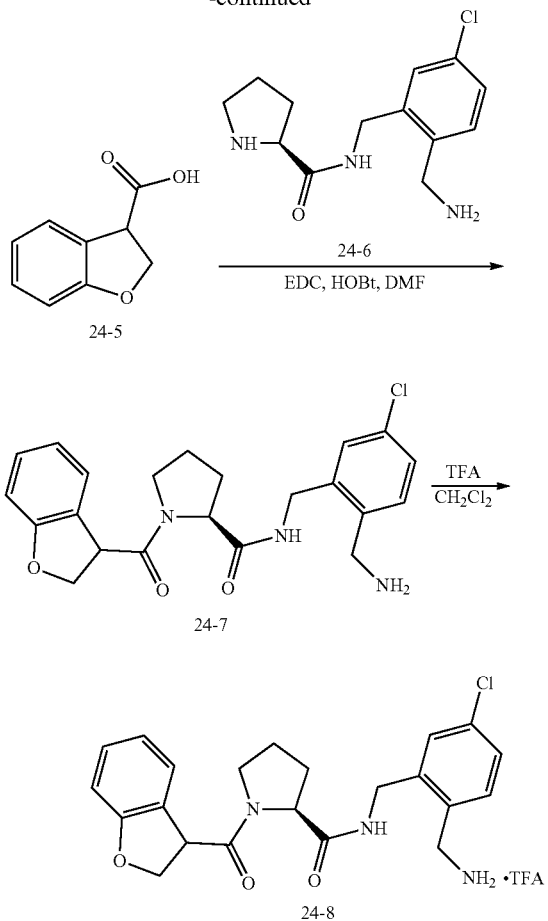

2-{(2-iodophenoxy)methyl}oxirane (24-3)

DIAD (2.18 mL, 11 mmol) was added dropwise to a solution of Iodophenol 24-1 (2.20 g, 10 mmol), epoxide 24-2 (0.82 g, 11 mmol), and PPh$_3$ (2.90 g, 11 mmol) in THF (20 mL) at 0° C. and reaction mixture was stirred at room temperature for 5 h. The mixture was diluted with water (30 mL) and extracted with EtOAc (3×30 mL). The combined organic extract was washed with brine solution (100 mL) and concentrated under reduced pressure. The residue was purified by combiflash (silica gel: 10% EtOAc/hexanes) to provide oxirane 24-3 yellow oil.

(2,3-Dihydrobenzofuran-3-yl)methanol (24-4)

A 2M solution of n-BuLi in THF (0.76 mL, 1.5 mmol) was added dropwise to the solution of oxirane 24-3 (0.28 g, 1.01 mmol) in THF (8 mL) at −90° C. and the reaction mixture was warmed to room temperature over a period of 2 h. The mixture was stirred at room temperature for 1 h and quenched with water (50 mL) and extracted with EtOAc (3×30 mL). The combined organic extract was washed with brine (30 mL), dried over anhydrous Na$_2$SO$_4$, filtered and concentrated under reduced pressure. The residue was purified by combiflash (silica gel: 30-40% EtOAc/Hexanes) to provide alcohol 24-4 as colorless oil.

2,3-Dihydrobenzofuran-3-carboxylic acid (24-5)

Chromium trioxide (2.5 mg, 2 mol %) and $H_5IO_6$ (0.58 g, 2.6 mmol) were dissolved in MeCN (8 mL) by vigorous stirring at room temperature 15 min. The solution was delivered via syringe into the pre-cooled solution of the alcohol 24-4 (0.20 g, 1.3 mmol) in $CH_2Cl_2$ (10 mL) at 0° C. over a period of 10 min and stirred at room temperature for 6 h. The reaction was quenched with water (30 mL) and aqueous layer was washed with EtOAc (2×30 mL), acidified with 1N HCl and extracted with EtOAc (3×30 mL). The combined organic extract was dried over anhydrous $Na_2SO_4$, filtered and concentrated. The residue was purified by reverse phase combiflash (C18: 10-100% acetonitrile water) to provide acid 24-5 as off white solid.

tert-Butyl-4-chloro-2-[{(2S)-1-(2,3-dihydrobenzofuran-3-carbonyl)pyrrolidine-2-carboxamido}methyl]benzylcarbamate (24-7)

A mixture of acid 5 (0.30 g, 1.8 mmol), amine 24-6 (0.67 g, 1.8 mmol), EDC (1.05 g, 5.4 mmol) and HOBt (0.24 g, 1.8 mmol) in DMF (10 mL) was stirred at room temperature for 16 h. The mixture was diluted with water (20 mL) and extracted with EtOAc (3×20 mL). The combined organic extract was washed with water (2×30 mL), brine (30 mL), dried over anhydrous $Na_2SO_4$, filtered and concentrated under reduced pressure. The residue was purified by reverse phase combiflash (C18: 10-100% acetonitrile/water) to obtain amide 24-7 as white solid.

(2S)-N-{2-(Aminomethyl)-5-chlorobenzyl}-1-(2,3-dihydrobenzofuran-3-carbonyl)pyrrolidine-2-carboxamide-2,2,2-trifluoroacetate (24-8)

A 50% solution of TFA in $CH_2Cl_2$ (5 mL) was added to the solution of amide 7 (0.20 g, 0.38 mmol) in $CH_2Cl_2$ (1 mL) and reaction mixture was stirred at room temperature for 3 h. The solvent was removed under reduced pressure and residue was azeotroped with toluene (2×20 mL) and purified by reverse phase combiflash (C18; 30% acetonitrile/water) to provide 24-8. $^1$H NMR (MeOD, 400 MH$_z$) (δ) ppm (mixture of diastereomers): 7.45-7.34 (m, 3H), 7.20-7.10 (m, 2H), 6.86-6.73 (m, 2H), 4.70-4.63 (m, 3H), 4.49-4.24 (m, 3H), 4.18 (d, J=4 Hz, 2H), 3.96-3.91 (m, 1H), 3.93-3.78 (m, 1H), 2.32-1.93 (m, 4H).

EXAMPLE 25

(2S)-N-{2-(Aminomethyl)-5-chlorobenzyl}-1-(indoline-3-carbonyl)pyrrolidine-2-carboxamide bis(2,2,2-trifluoroacetate) (25-5)

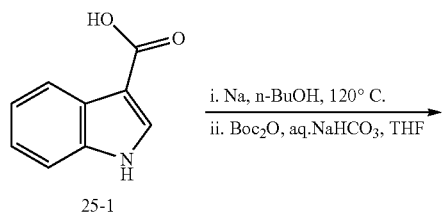

i. Na, n-BuOH, 120° C.
ii. Boc$_2$O, aq.NaHCO$_3$, THF 25-1

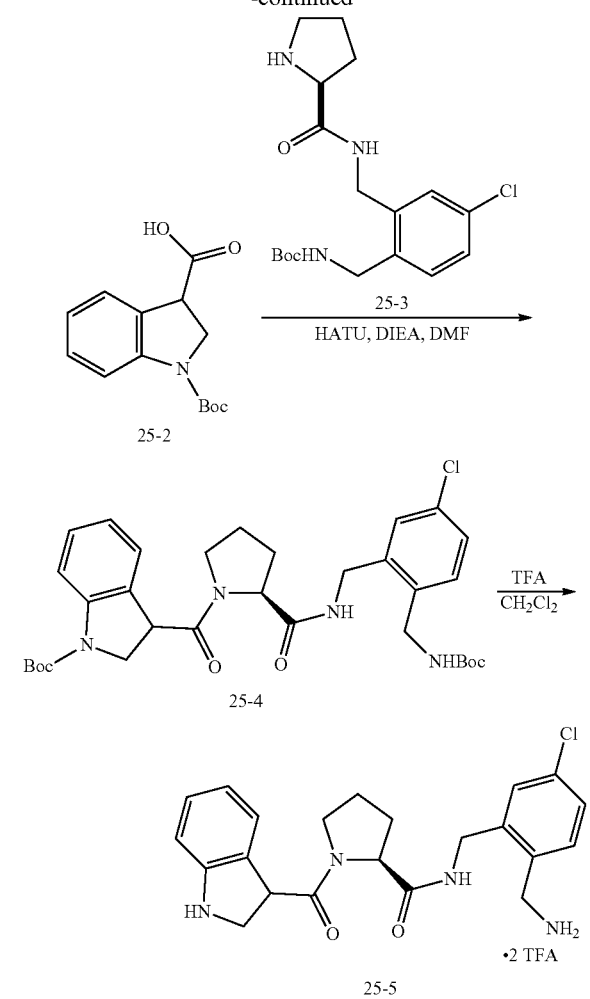

1-(tert-Butoxycarbonyl)indoline-3-carboxylic acid (25-2)

Freshly cut pieces of sodium (3.80 g, 165 mmol) were added to the solution of 1H-indole-3-carboxylic acid 25-1 (2.00 g, 12.4 mmol) in n-BuOH (60 mL) at 70° C. over a period of 1 h and the resulting mixture was refluxed at 125° C. for 2 h under nitrogen. The reaction mixture was cooled to room temperature and quenched by the careful addition of ice cold water (100 mL). The organic solvent removed under reduced pressure and mixture was diluted with water (20 mL). The aqueous layer was acidified to pH 2-3 with 2M HCl and washed with $CH_2Cl_2$ (2×100 mL). The aqueous layer was basified to pH 9-10 with aqueous NaHCO$_3$ solution. Then a solution of Boc anhydride (4.02 g, 18.1 mmol) in THF (50 mL) was added dropwise and the reaction mixture was stirred at room temperature for 15 h. THF was evaporated under reduced pressure and aqueous layer was washed with MTBE (2×100 mL). The aqueous layer acidified to pH 3-4 with saturated KHSO$_4$ solution, and extracted with EtOAc (2×100 mL). The combined organic layers were washed with brine (100 mL), dried over anhydrous Na$_2$SO$_4$ and concentrated to afford boc protected indoline-3-carboxylic acid 25-2 as a brown hygroscopic solid:

tert-Butyl 3-{(S)-2-{(2-[{(tert-butoxycarbonyl)amino}methyl]-5-chlorobenzyl)carbamoyl}pyrrolidine-1-carbonyl}indoline-1-carboxylate (25-4)

A mixture of amine 25-3 (0.25 g, 0.69 mmol), acid 25-2 (0.21 g, 0.81 mmol), HATU (0.79 g, 2.09 mmol) and DIPEA (0.36 mL, 2.09 mmol) in DMF (10 mL) was stirred under nitrogen for 3 h at room temperature. The reaction was diluted with water (40 mL) and extracted with EtOAc (3×20 mL). The combined organic layers were washed with water (2×100 mL), brine (50 mL), dried over anhydrous $Na_2SO_4$, and concentrated under reduced pressure. The residue was purified by reverse phase combiflash chromatography (C18, 2:3 $H_2O/CH_3CN$) to afford amide 25-4.

(2S)-N-{2-(Aminomethyl)-5-chlorobenzyl}-1-(indoline-3-carbonyl)pyrrolidine-2-carboxamide bis(2,2,2-trifluoroacetate) (25-5)

A 50% solution of TFA in $CH_2Cl_2$ (8 mL) was added to the solution of amide 25-4 (0.15 g, 0.24 mmol) in $CH_2Cl_2$ (2 mL) and reaction mixture was stirred under nitrogen for 2 h. The solvent was removed under reduced pressure and the residue was azeotroped with toluene (2×10 mL). A hygroscopic solid was dissolved in 1:1 acetonitrile/water (4 mL) and lyophilized for 24 h to obtain 25-5. $^1$H NMR (300 MHz, MeOD) δ 7.48-7.27 (m, 5H), 7.24-7.10 (m, 2H), 4.73 (quat, J=8.4 Hz, 1H), 4.58-4.42 (m, 1H), 4.42-4.26 (m, 2H), 4.18 (d, J=18.0, 2H), 4.05-3.81 (m, 4H), 2.40-1.91 (m, 4H).

EXAMPLE 26

Preparation of (2S)-N-{2-(Aminomethyl)-5-chlorobenzyl}-1-(5-hydroxy-6,7-dihydro-5H-cyclopenta[b]pyridine-5-carbonyl}azetidine-2-carboxamide bis(2,2,2-trifluoroacetate) (26-12)

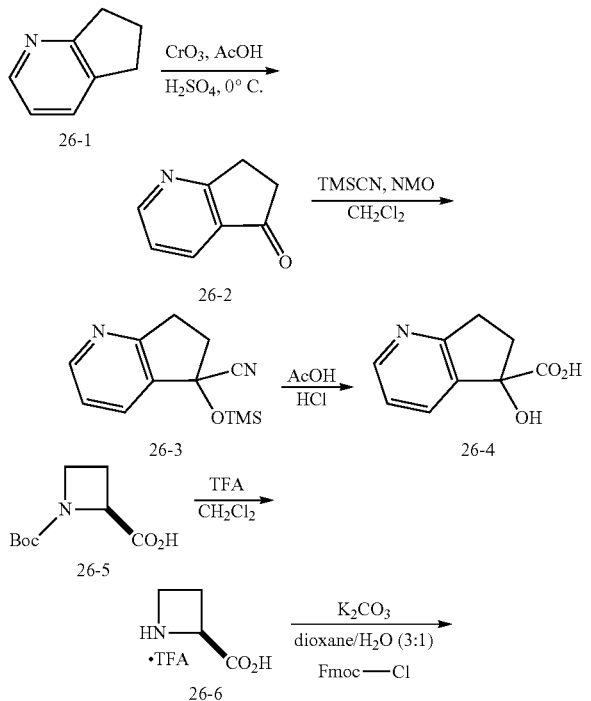

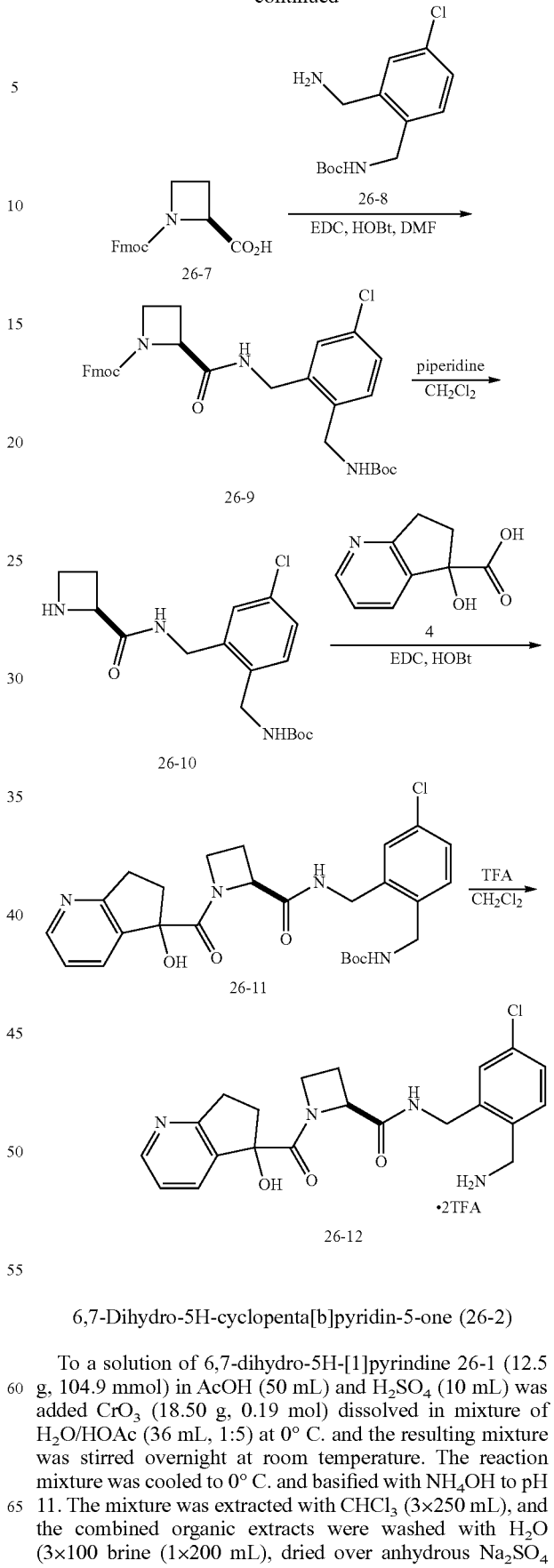

6,7-Dihydro-5H-cyclopenta[b]pyridin-5-one (26-2)

To a solution of 6,7-dihydro-5H-[1]pyrindine 26-1 (12.5 g, 104.9 mmol) in AcOH (50 mL) and $H_2SO_4$ (10 mL) was added $CrO_3$ (18.50 g, 0.19 mol) dissolved in mixture of $H_2O/HOAc$ (36 mL, 1:5) at 0° C. and the resulting mixture was stirred overnight at room temperature. The reaction mixture was cooled to 0° C. and basified with $NH_4OH$ to pH 11. The mixture was extracted with $CHCl_3$ (3×250 mL), and the combined organic extracts were washed with $H_2O$ (3×100 brine (1×200 mL), dried over anhydrous $Na_2SO_4$ and concentrated. The residue was purified by column chromatography (silica gel; 60% EtOAc/hexanes) to provide ketone 26-2 as brown oil.

5-Hydroxy-6,7-dihydro-5H-cyclopenta[b]pyridine-5-carbonitrile (26-3)

NMO (0.44 g, 0.37 mmol) and TMSCN (7.5 mmol) was added to a solution of ketone 26-2 (1.00 g, 7.5 mmol) in CH$_2$Cl$_2$ (5 mL) and the reaction mixture was stirred at room temperature for 16 h. The solvent was removed under reduced pressure and residue was purified by column chromatography (silica gel; eluent EtOAc/hexanes) to provide cyanohydrin 26-3 as oil.

5-Hydroxy-6,7-dihydro-5H-cyclopenta[b]pyridine-5-carboxylic acid (26-4)

To a stirred solution of cyanohydrin 26-3 (1.34 g, 5.76 mmol) in AcOH (3 mL), was added conc. HCl (5 mL) and reaction mixture was stirred at room temperature for 16 h. The solvent was removed under reduced pressure and the residue was azeotroped with toluene (2×15 mL) and washed with EtOAc and CH$_2$Cl$_2$ to afford acid 26-4 as off white solid.

(S)-1-[{(9H-Fluoren-9-yl)methoxy}carbonyl]azetidine-2-carboxylic acid (26-7)

A 50% solution of TFA in CH$_2$Cl$_2$ (20 mL) was added to the solution of the 1-Boc-azetidine-2-carboxylic acid 26-5 (1.00 g, 4.9 mmol) in CH$_2$Cl$_2$ (2 mL) and mixture was stirred at room temperature for 4 h. The solvent was removed under reduced pressure, residue was azetrope with toluene (2×20 mL) and dried over high vacuum pump for 2 h. The crude residue was used for next step without purification.

A solution of Fmoc-Cl (1.08 g, 4.18 mmol) in 1,4-dioxane (5 mL) was added to the mixture of above residue and K$_2$CO$_3$ (1.15 g, 8.37 mmol) in dioxane/water (20 mL, 4:1). The mixture was stirred at room temperature for 16 h. The organic solvent was removed at reduced pressure, and mixture was diluted with water (20 mL). The aqueous layer was washed with MTBE (30 mL), acidified with 10% aqueous KHSO$_4$ to pH 2 and extracted with EtOAc (3×20 mL). The combined organic extract was washed with brine solution (20 mL), dried over anhydrous Na$_2$SO$_4$ and concentrated to get acid 26-7 as white solid.

(S)-(9H-Fluoren-9-yl)methyl 2-{(2-[{(tert-butoxycarbonyl)amino}methyl]-5-chlorobenzyl)carbamoyl}azetidine-1-carboxylate (26-9)

A mixture of acid 26-7 (0.50 g, 1.78 mmol), amine 26-8 (484 mg, 1.78), EDC (1.02 g, 5.36 mmol) and HOBt (0.24 g, 1.78 mmol) in DMF:THF (1:1, 20 mL) was stirred at room temperature for 16 h. The solvent was removed under reduced pressure and the residue was purified by column chromatography (silica gel: 20-30% EtOAc/hexanes) to provide amide 26-9 as off white solid.

(S)-tert-Butyl 2-{(azetidine-2-carboxamido)methyl}-4-chlorobenzylcarbamate (26-10)

A solution of 50% piperidine in CH$_2$Cl$_2$ (5 mL) was added to the solution of Fmoc protected mine 26-9 (0.57 g, 0.98 mmol) and reaction mixture was stirred at room temperature for 1 h. The solvent was removed under reduced pressure and residue was purified by reverse phase combiflash (C18: 10-100% acetonitrile-water) to provide amine 26-10 as colorless gum.

tert-Butyl-4-chloro-2-[{(2S)-1-(5-hydroxy-6,7-dihydro-5H-cyclopenta[b]pyridine-5-carbonyl)azetidine-2-carboxamido}methyl]benzylcarbamate (26-11)

A mixture of amine 26-10 (0.20 g, 0.56 mmol), acid 26-4 (0.12 g, 0.56 mmol), EDC (0.32 g, 1.39 mmol) and HOBT (0.076 g, 0.56 mmol) in DMF (10 mL) was stirred at room temperature for 16 h. The solvent was removed at reduced pressure and residue was purified by combiflash (silica gel: 0-10% EtOAc/MeOH) to provide amide 26-11 as white solid.

(2S)-N-{2-(Aminomethyl)-5-chlorobenzyl}-1-(5-hydroxy-6,7-dihydro-5H-cyclopenta[b]pyridine-5-carbonyl)azetidine-2-carboxamide bis(2,2,2-trifluoroacetate) (26-12)

A solution of 50% TFA (5 mL) in CH$_2$Cl$_2$ (1 mL) was added dropwise to the solution of amide 26-11 (0.18 g, 0.35 mmol) and reaction mixture was stirred at room temperature for 3 h. The solvent was removed under reduced pressure, residue was azeotroped with toluene (2×10 mL) and purified by reverse phase combiflash (C18: 10% acetonitrile/water) to provide 26-12

EXAMPLE 27

Preparation of {(2S)-N-{2-(Aminomethyl)-5-chlorobenzyl}-1-(5-hydroxy-6,7-dihydro-5H-cyclopenta[c]pyridine-5-carbonyl)pyrrolidine-2-carboxamide bis(2,2,2-trifluoroacetate) (27-9)

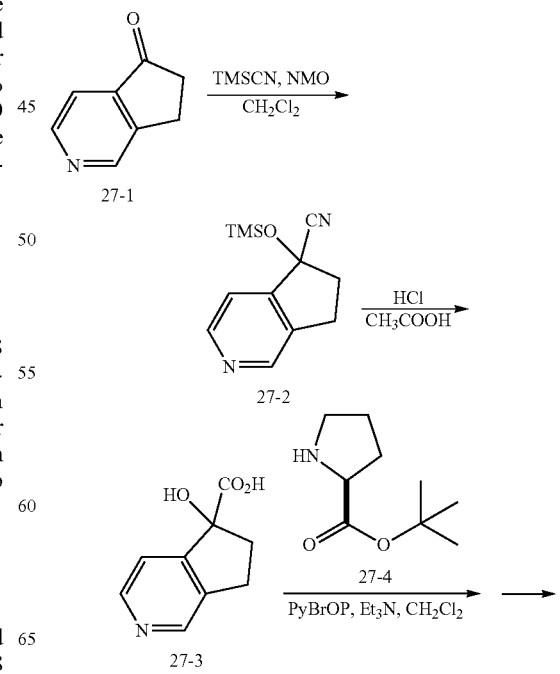

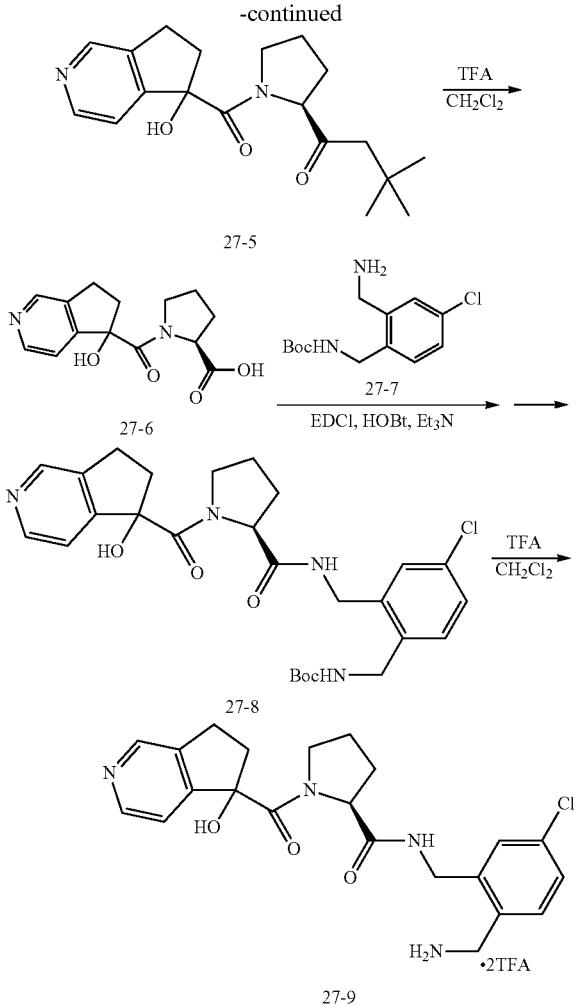

5-{(Trimethylsilyl)oxy}-6,7-dihydro-5H-cyclopenta[c]pyridine-5-carbonitrile (27-2)

NMO (0.396 g, 3.383 mmol), and TMSCN (0.67 mL, 5.057 mmol) was added to a stirred solution of ketone 27-1 (0.45 g, 3.383 mmol) in $CH_2Cl_2$ (15 mL) and the mixture was stirred at room temperature for 4 h. The reaction mixture was quenched with saturated aqueous $NH_4Cl$ solution (10 mL) and extracted with $CH_2Cl_2$ (2×15 mL). The combined organic layers were washed with water (10 mL), brine (10 mL), dried over $Na_2SO_4$, and concentrate at reduced pressure. The residue was purified by flash chromatography (silica gel; eluent: 0-10% EtOAc/hexanes) to afford cyanohydrin 27-2 as colorless oil.

7-Hydroxy-6,7-dihydro-5H-cyclopenta[b]pyridine-7-carboxylic acid (27-3)

To a stirred solution of cyanohydrin 27-2 (0.6 g, 3.631 mmol) in $CH_3COOH$ (2 mL) was added con. HCl (2 mL) and the mixture was heated at 60° C. for 16 h under nitrogen. The solvent was removed under reduced pressure, the residue was azeotroped with toluene (2×10 mL) and washed with EtOAc (20 mL) and $CH_2Cl_2$ (20 mL) to afford acid 27-3 as white hygroscopic solid.

(2S)-tert-Butyl 1-(5-hydroxy-6,7-dihydro-5H-cyclopenta[c]pyridine-5-carbonyl)pyrrolidine-2-carboxylate (27-5)

PyBrOP (2.08 g, 4.469 mmol) was added in portions to a solution of amine 27-4 (0.464 g, 2.23 mmol), acid 27-3 (0.400 g, 2.23 mmol), and triethyl amine (1.5 mL, 11.17 mmol) in $CH_2Cl_2$ (5 mL) at 0° C. and the mixture was stirred at room temperature for 2 h. The reaction was quenched with saturated $NaHCO_3$ solution (5 mL) and extracted with $CH_2Cl_2$ (2×20 mL). The combined organic layers was washed with water (20 mL), brine (20 mL) and dried over $Na_2SO_4$, concentrate under reduced pressure. The crude was purified reverse phase flash chromatography (C18 column; 10-60% acetonitrile-water) to afford amide 27-5 as a white solid.

(2S)-1-(5-Hydroxy-6,7-dihydro-5H-cyclopenta[c]pyridine-5-carbonyl)pyrrolidine-2-carboxylic acid (27-6)

Trifluoroacetic acid (2 mL, 50% solution in $CH_2Cl_2$) was added to a solution of t-butyl ester 27-5 (0.12 g, 0.361 mmol) in $CH_2Cl_2$ (2 mL) and reaction mixture was stirred under nitrogen at room temperature for 2 h. The solvent was removed at reduced pressure and the residue was azeotroped with toluene (5 mL). The solid was washed with diethyl ether (2×5 mL) and dried under high vacuum to afford acid 27-6 as off-white hygroscopic solid.

tert-Butyl-4-chloro-2-[{(2S)-1-(5-hydroxy-6,7-dihydro-5H-cyclopenta[c]pyridine-5-carbonyl)pyrrolidine-2-carboxamido}methyl]benzylcarbamate (27-8)

A mixture of acid 27-6 (0.08 g, 0.289 mmol), amine 27-7 (0.078 g, 0.289 mmol), triethyl amine (0.12 mL, 0.869 mmol), EDCI (66.6 mg, 0.347 mmol), and HOBt (39.0 mg, 0.347 mmol) in DMF (10 mL) was stirred at room temperature for 16 h. The reaction was quenched with saturated $NaHCO_3$ solution (5 mL) and extracted with $CH_2Cl_2$ (2×15 mL). The combined organic layers were washed with water (15 mL), brine (15 mL) and dried over $Na_2SO_4$, concentrate at reduced pressure. The crude was purified by reverse phase flash chromatography (C18; eluent: 10%-40% water/acetonitrile) to afford Boc protected compound 27-8 as white solid.

{(2S)-N-{2-(Aminomethyl)-5-chlorobenzyl}-1-(5-hydroxy-6,7-dihydro-5H-cyclopenta[c]pyridine-5-carbonyl)pyrrolidine-2-carboxamide bis(2,2,2-trifluoroacetate) (27-9)

Trifluoroacetic acid (1 mL, 50% solution in $CH_2Cl_2$) was added to a solution of Boc protected amine 27-8 (0.025 g, 0.047 mmol) in $CH_2Cl_2$ (2 mL) and reaction mixture was stirred under nitrogen for 1 h at room temperature. The solvent was removed under reduced pressure and the residue was azeotroped with toluene (5 mL). The solid was washed with diethyl ether (2×5 mL), filtered, and dried under high vacuum to afford 27-9 as hygroscopic off-white solid. $^1$H NMR (MeOD-$d_4$, 300 MHz) (δ) ppm: 8.71 (m, 1H), 8.61-8.64 (m, 1H), 7.72-7.84 (m, 1H), 7.45-7.55 (m, 1H), 7.38-7.41 (m, 2H), 4.41-4.80 (m, 3H), 4.21-4.30 (m, 2H), 3.97-4.00 (m, 1H), 3.52-3.65 (m, 1H), 3.08-3.19 (m, 2H), 2.72-2.77 (m, 1H), 2.42-2.51 (m, 1H), 2.23-2.31 (m, 1H), 2.03-2.21 (m, 1H), 1.81-2.00 (2H, m).

EXAMPLE 28

Preparation of (2S)-N-{2-(aminomethyl)-5-chlorobenzyl}-1-(7-hydroxy-6,7-dihydro-5H-cyclopenta[c]pyridine-7-carbonyl)pyrrolidine-2-carboxamide bis (2,2,2-trifluoroacetate) (28-6)

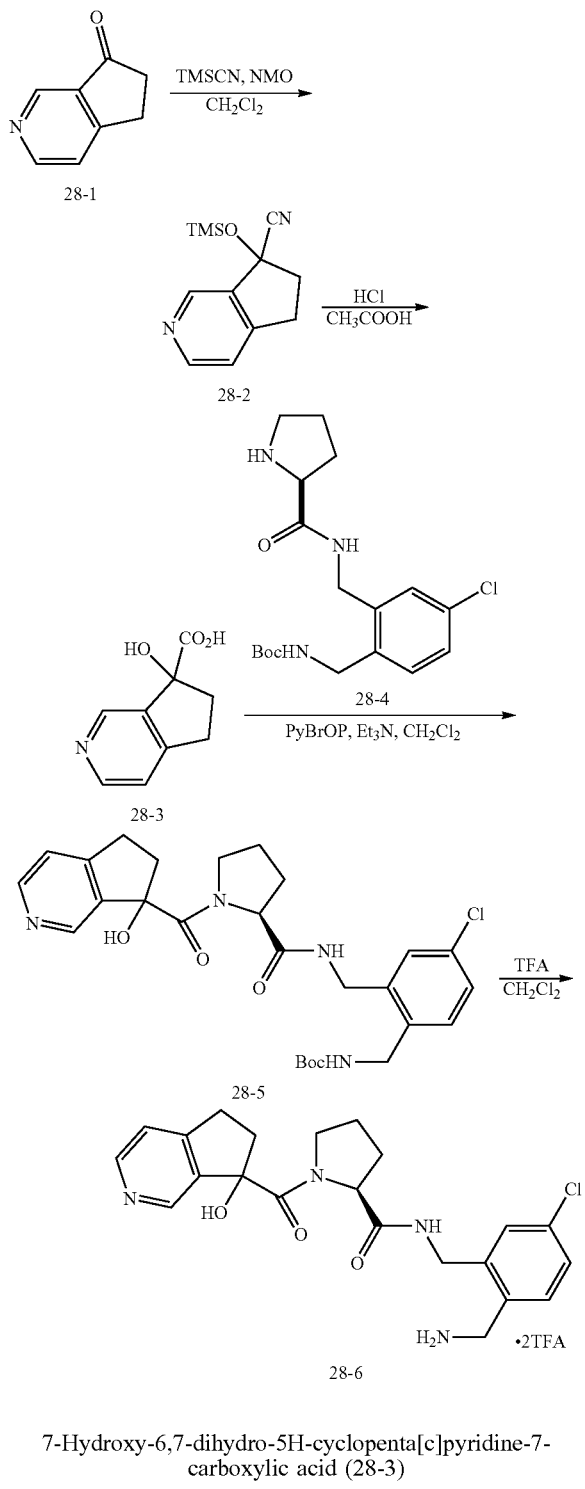

7-Hydroxy-6,7-dihydro-5H-cyclopenta[c]pyridine-7-carboxylic acid (28-3)

TMSCN (0.59 mL, 4.40 mmol) and NMO (0.103 g, 0.88 mmol) was added to a stirred solution of 5H-cyclopenta[c]pyridin-7(6H)-one 28-1 (0.5 g, 2.90 mmol) in $CH_2Cl_2$ (20 mL) and reaction mixture was stirred at room temperature for 5 h. The mixture was diluted with $CH_2Cl_2$ (50 mL) and washed with water (2×30 mL). The organic layer was dried over anhydrous $Na_2SO$, filtered and AcOH (5 mL) was added. The solvent ($CH_2Cl_2$) was removed and mixture was dissolved in AcOH (10 mL) and concentrated HCl (15 mL). The reaction mixture was stirred at room temperature for 24 h. Solvent was removed under reduced pressure and residue was reprecipitated from EtOAc to obtain hydroxyl acid 28-3 as pale yellow solid.

tert-Butyl-4-chloro-2-[{(2S)-1-(7-hydroxy-6,7-dihydro-5H-cyclopenta[c]-pyridine-7-carbonyl)pyrrolidine-2-carboxamido}methyl]benzylcarbamate (28-5)

PyBROP (3.23 g, 6.93 mmol) was added in portions to the mixture of acid 28-3 (0.75 g, 3.47 mmol), amine 28-4 (0.637 g, 1.73 mmol) and triethylamine (2.9 mL, 20.8 mmol) at 0-5° C. and the reaction mixture was stirred at same temperature for 2 h. The reaction was quenched by 1% aqueous citric acid solution (25 mL) and extracted with $CH_2Cl_2$ (100 mL). The combined organic extract were washed with saturated $NaHCO_3$ solution (50 mL), and brine (50 mL), dried over anhydrous $Na_2SO$, filtered and concentrated under reduced pressure. The residue was purified by reverse phase column chromatography followed by semi-prep HPLC to obtain amide 28-5 as sticky solid.

(2S)-N-{2-(Aminomethyl)-5-chlorobenzyl}-1-(7-hydroxy-6,7-dihydro-5H-cyclopenta[c]pyridine-7-carbonyl)pyrrolidine-2-carboxamide bis(2,2,2-trifluoroacetate) (28-6)

Trifluoroacetic acid (0.3 mL, 3.92 mmol) was added to the stirred solution of Boc protected amine 28-5 (90 mg, 0.17 mmol) in $CH_2Cl_2$ (5 mL) and reaction mixture was stirred at room temperature for 1 h. The solvent and volatiles were removed at reduced pressure and residue was dried under high vacuum. The crude compound was purified by reverse phase combiflash column chromatography (C18; eluent: 10-100% acetonitrile/water) to obtain 28-6 as yellow solid. $^1$H NMR (MeOD-$d_4$, 400 MHz) (δ) ppm: 8.60-8.68 (m, 2H), 7.86-7.97 (m, 1H), 7.50-7.65 (m, 1H), 7.31-7.46 (m, 2H), 4.18-4.53 (m, 5H), 3.93-4.07 (m, 1H), 3.56-3.83 (m, 1H), 3.32-3.44 (m, 1H), 3.12-3.27 (m, 1H), 2.65-2.82 (m, 1H), 2.46-2.56 (m, 1H), 2.21-2.33 (m, 1H), 1.83-2.17 (m, 3H).

EXAMPLE 29

Preparation of (2S)-1-(7-Amino-6,7-dihydro-5H-cyclopenta[b]pyridine-7-carbonyl)-N-(2-(aminomethyl)-5-chlorobenzyl)pyrrolidine-2-carboxamide tris(2,2,2-trifluoroacetate) (29-9)

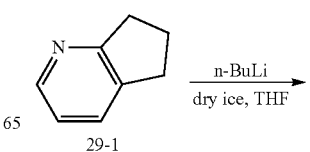

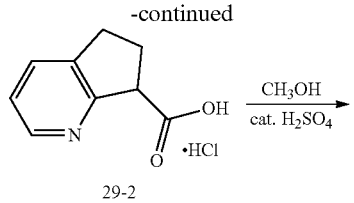

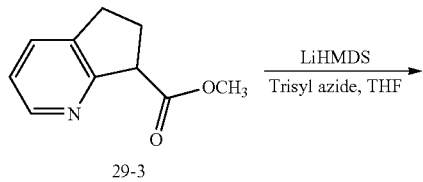

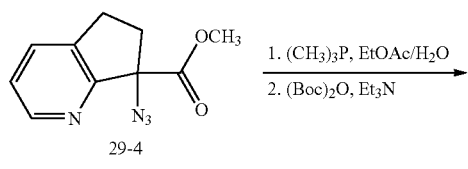

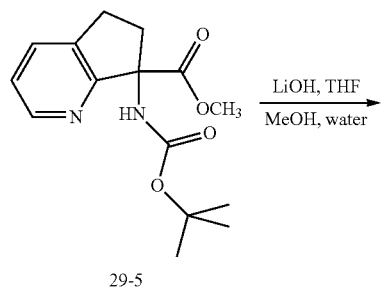

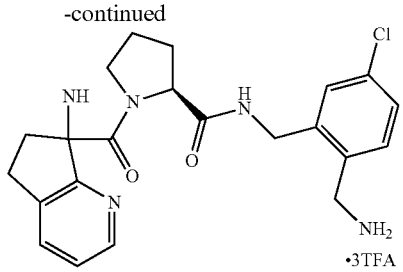

6,7-dihydro-5H-cyclopenta[b]pyridine-7-carboxylic acid (29-2)

A solution of n-BuLi (1.6 M, 78.0 mL, 126.0 mmol) in hexanes was added dropwise to a solution of 6,7-dihydro-5H-cyclopenta[b]pyridine 29-1 (10.0 g, 84.03 mmol) in anhydrous THF (15 mL) at 0° C. The reaction mixture was warmed to room temperature and stirred for additional 1 h. The mixture was poured into dry ice, and aged for 2 h. The reaction mixture was filtered off, dissolved in water (50 mL), basified to pH 14, washed with EtOAc (50 mL) and $CH_2Cl_2$ (50 mL) to remove impurities. The water layer was acidified to pH 2-3, concentrated under reduced pressure. The crude residue was dissolved in $CH_3OH$ (50 mL), filtered off the inorganic solids and the filtrate was concentrated to afford 6,7-dihydro-5H-cyclopenta[b]pyridine-7-carboxylic acid hydrochloride 29-2 as yellow solid.

Methyl-6,7-dihydro-5H-cyclopenta[b]pyridine-7-carboxylate (29-3)

To a solution of acid 29-2 (1.0 g, 6.097 mmol) in $CH_3OH$ (20 mL), was added conc. $H_2SO_4$ (catalytic) and the reaction was heated under reflux for 2 h. The solvent was removed under reduced pressure, the residue was dissolved in water (20 mL), neutralized to pH 7 and extracted with EtOAc (2×15 mL). The combined organic layers were washed with water (20 mL), brine (20 mL) and dried over $Na_2SO_4$, concentrate at reduced pressure to afford methyl ester 29-3 as colorless oil.

Methyl-7-azido-6,7-dihydro-5H-cyclopenta[b]pyridine-7-carboxylate (29-4)

A 1.0 M solution of LiHMDS (6.21 mL, 6.214 mmol) in hexanes was added dropwise to a solution of ester 29-3 (1.0 g, 84.03 mmol) in anhydrous THF (15 mL) at −20° C. under nitrogen and the mixture was stirred for 15 min. An ice cooled solution of trisyl azide (1.92 g, 6.214 mmol) in THF (5 mL) was added drop wise at −78° C. and the mixture was stirred for 10 min. The reaction mixture was quenched with water (10 mL) and extracted with EtOAc (2×20 mL). The combined organic layers were washed with brine (20 mL) and dried over anhydrous $Na_2SO_4$, filtered and concentrated under reduced pressure. The residue was purified by reverse phase flash chromatography (C18; eluent: 10%-70% water/acetonitrile) to afford azide 29-4 as light yellow solid.

Methyl-7-(tert-butoxycarbonylamino)-6,7-dihydro-5H-cyclopenta[b]pyridine-7-carboxylate (29-5)

A 1.0 M solution of trimethyl phosphine (6.12 mL, 2.064 mmol) in THF was added dropwise to a solution of azide 29-4 (0.9 g, 4.128 mmol) in EtOAc/H$_2$O mixture (20 mL, 10:1) and mixture was stirred under nitrogen at room temperature for 15 min. A solution of (Boc)$_2$O (0.9 g, 4.128 mmol) in THF (5 mL), Et$_3$N (0.57 mL, 4.128 mmol) was added and the mixture was stirred under nitrogen at room temperature for 16 h. The reaction mixture was quenched with water (15 mL) and extracted with EtOAc (2×20 mL). The combined organic layers were washed with brine (20 mL) and dried over anhydrous Na$_2$SO$_4$, filtered and concentrate under reduced pressure to afford Boc protected amine 29-5 as white solid.

7-(tert-Butoxycarbonylamino)-6,7-dihydro-5H-cyclopenta[b]pyridine-7-carboxylic acid hydrochloride acid (29-6)

A solution of LiOH (0.061 g, 2.56 mmol) in water (4 mL) was added dropwise to a solution of ester 29-5 (0.25 g, 0.856 mmol) in THF/MeOH (2:1, 6 mL) and the mixture was stirred under nitrogen for 16 h at room temperature. The solvent was removed at the reduced pressure, residue was dissolved in water (5 mL), acidified to pH 2-3 using 1N HCl and washed with EtOAc (2×10 mL). The aqueous layer was concentrated under reduced pressure. The solid residue was suspended in MeOH (20 mL), filtered, and filtrate was concentrated to afford acid 29-6 as off-white solid.

(2S)-1-{7-(tert-Butoxycarbonyl)-amino}-6,7-dihydro-5H-cyclopenta[b]pyridine-7-carbonyl)-N-{2-(aminomethyl)-5-chlorobenzyl}pyrrolidine-2-carboxamide (29-8)

PyBrOP (0.505 g, 1.08 mmol) was added in portions to a mixture of amine 29-7 (0.2 g, 0.541 mmol), acid 29-6 (0.15 g, 0.541 mmol), and triethyl amine (0.45 mL, 3.25 mmol), at 0° C. and the reaction was stirred under nitrogen for 2 h at room temperature. The reaction was quenched with saturated NaHCO$_3$ solution (5 mL) and extracted with CH$_2$Cl$_2$ (2×20 mL). The combined organic layers were washed with water (15 mL), brine (15 mL) and dried over anhydrous Na$_2$SO$_4$, filtered and concentrated under reduced pressure. The residue was purified by reverse phase flash chromatography (C18; eluent: 10%-60% water/acetonitrile) to afford non polar diastereomers 29-8a as white solid and polar diasteromer 29-8b as white solid.

(2S)-1-(7-Amino-6,7-dihydro-5H-cyclopenta[b]pyridine-7-carbonyl)-N-(2-(aminomethyl)-5-chlorobenzyl)pyrrolidine-2-carboxamide tris(2,2,2-trifluoroacetate) (29-9a)

Trifluoroacetic acid (3 mL, 50% solution in CH$_2$Cl$_2$) was added to the solution of Boc protected diasteromer 29-8a (0.05 g, 0.08 mmol) in CH$_2$Cl$_2$ (2 mL) and reaction mixture was stirred under nitrogen for 1 h at room temperature. The solvent was removed at reduced pressure and the residue was azeotroped with toluene (5 mL). The solid was washed with diethyl ether (2×5 mL), filtered and dried under high vacuum to afford 29-9a. $^1$H NMR (MeOD-d$_4$, 400 MH$_Z$) (δ) ppm: 8.52-7.53 (d, J=4.4, 1H), 7.92-7.90 (d, J=7.6, 1H), 7.39-7.55 (m, 4H), 4.61-4.65 (m, J =12, 1H), 4.50-4.53, (dd, J=3.6 Hz, J=8.4 Hz, 1H), 4.23-4.35 (m, 4H), 3.31-3.40 (m, 1H), 3.15-3.20 (m, 1H), 2.88-2.95 (m, 1H), 2.41-2.51 (m, 1H), 2.31-2.34 (m, 1H), 2.14-2.15 (m, 1H), 1.72-1.83 (s, 3H).

(2S)-1-(7-Amino-6,7-dihydro-5H-cyclopenta[b]pyridine-7-carbonyl)-N-(2-(aminomethyl)-5-chlorobenzyl)pyrrolidine-2-carboxamide tris(2,2,2-trifluoroacetate) (29-9b)

Trifluoroacetic acid (3 mL, 50% solution in CH$_2$Cl$_2$) was added to the solution of Boc protected amine 29-8b (0.04 g, 0.064 mmol) in CH$_2$Cl$_2$ (2 mL) and reaction mixture was stirred under nitrogen for 1 h at room temperature. The solvent was removed at reduced pressure and the residue was azeotroped with toluene (5 mL). The solid was washed with diethyl ether (2×5 mL) and dried under high vacuum to afford 29-9b. $^1$H NMR (MeOD-d$_4$, 400 MHz) (δ) ppm: 8.55 (d, J=1.6, 1H), 7.91 (d, J=1.6, 1H), 7.49 (dd, J=4.8 Hz, J=7.6 Hz, 1H), 7.40-7.44 (m, 2H), 1.61-1.64 (m, 1H), 4.52-4.59 (m, 2H), 4.34 (d, J=15.2 Hz, 2H), 4.25 (s, 2H), 3.31-3.40 (m, 1H), 2.99-3.03 (m, 1H), 2.47-2.51 (m, 1H), 2.07-2.27 (m, 3H), 1.78-1.88 (m, 3H).

EXAMPLE 30

Synthesis of (2S)-N-{2-(Aminomethyl)-5-chlorobenzyl}-1-(5-hydroxy-5,6,7,8-tetrahydroquinoline-5-carbonyl)pyrrolidine-2-carboxamide bis(2,2,2-trifluoroacetate)(30-6)

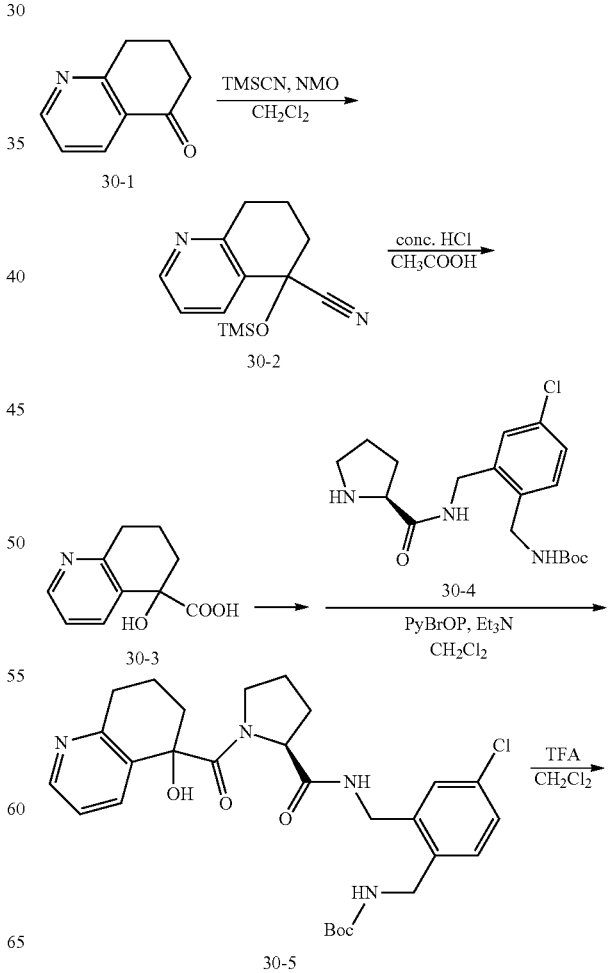

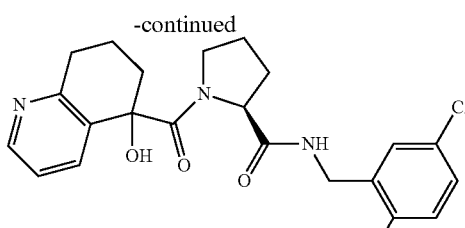

30-6

5-{(Trimethylsilyl)oxy}-5,6,7,8-tetrahydroquinoline-5-carbonitrile (30-2)

NMO (0.08 g, 0.680 mmol) and TMSCN (0.101 g, 1.020 mmol) was added to a solution of 7,8-dihydroquinolin-5 (6H)-one 30-1 (0.1 g, 0.680 mmol) in $CH_2Cl_2$ (2 mL) and the mixture was stirred under nitrogen at room temperature for 1 h. The reaction was quenched with water (10 mL) and extracted with $CH_2Cl_2$ (2×50 mL). The combined organic layers were washed with water (10 mL), brine (10 mL) and dried over anhydrous $Na_2SO_4$, and concentrated under reduced pressure. The residue was purified by flash chromatography (silica gel; eluent: 0-20% EtOAc/hexanes) to afford cyanohydrin 30-2 as a colorless oil.

5-Hydroxy-5,6,7,8-tetrahydroquinoline-5-carboxylic acid (30-3)

A mixture of cyanohydrin 30-2 (0.4 g, 1.626 mmol) in $CH_3COOH$ (5 mL) and conc. HCl (2.5 mL) was heated in sealed tube at 60° C. for 24 h. The solvent and volatiles were removed at reduced pressure and residue was azeotroped with toluene (15 mL), washed with EtOAc (15 mL) and $CH_2Cl_2$ (15 mL) to afford hydroxyl acid 30-3 as a white hygroscopic solid.

tert-Butyl-4-chloro-2-[{(2S)-1-(5-hydroxy-5,6,7,8-tetrahydroquinoline-5-carbonyl)pyrrolidine-2-carboxamido}methyl]benzylcarbamate (30-5)

PyBrOP (0.483 g, 1.036 mmol) was added to a mixture of amine 30-4 (0.190 g, 0.518 mmol), acid 30-3 (0.150 g, 0.777 mmol), and triethyl amine (0.45 mL, 3.269 mmol) in $CH_2Cl_2$ (5 mL) at 0° C. and the reaction was stirred for 2 h at room temperature under nitrogen. The reaction was quenched with saturated $NaHCO_3$ solution (5 mL) and extracted with $CH_2Cl_2$ (2×20 mL). The combined organic layers were washed with water (15 mL), brine (15 mL), dried over anhydrous $Na_2SO_4$, and concentrated under reduced pressure. The residue was purified by reverse phase flash chromatography (C18; eluent: 10%-40% acetonitrile/water) to afford Boc protected compound 30-5 as a white solid.

(2S)-N-{2-(Aminomethyl)-5-chlorobenzyl}-1-(5-hydroxy-5,6,7,8-tetrahydroquinoline-5-carbonyl) pyrrolidine-2-carboxamide (30-6)

Trifluoroacetic acid (0.5 mL, 50% solution in $CH_2Cl_2$) was added to a solution of Boc protected amine 30-5 (35 mg, 0.064 mmol) in $CH_2Cl_2$ (1 mL) and the reaction mixture was stirred under nitrogen at room temperature for 1 h. The solvent was removed at reduced pressure and the residue was azeotroped with toluene (5 mL). The solid was washed with ether (2×4 mL), filtered and dried under high vacuum to afford 30-6. $^1$H NMR (MeOD, 400 MHz) (δ) ppm: 8.60 (1H, s), 8.20-8.39 (m, 1H), 7.50-7.74 (m, 1H), 7.41-7.50 (m, 1H), 7.36-7.39 (m, 2H), 4.20-4.55 (m, 5H), 3.85-4.00 (m, 1H), 3.47-3.70 (m, 1H), 3.04-3.14 (m, 2H), 2.20-2.40 (m, 2H), 1.81-2.2.15 (m, 6H).

EXAMPLE 31

Preparation of (2S)-N-{2-(Aminomethyl)-5-chlorobenzyl}-1-(5-hydroxy-5,6,7,8-tetrahydroisoquinoline-5-carbonyl)pyrrolidine-2-carboxamide bis(2,2,2-trifluoroacetate) (31-7)

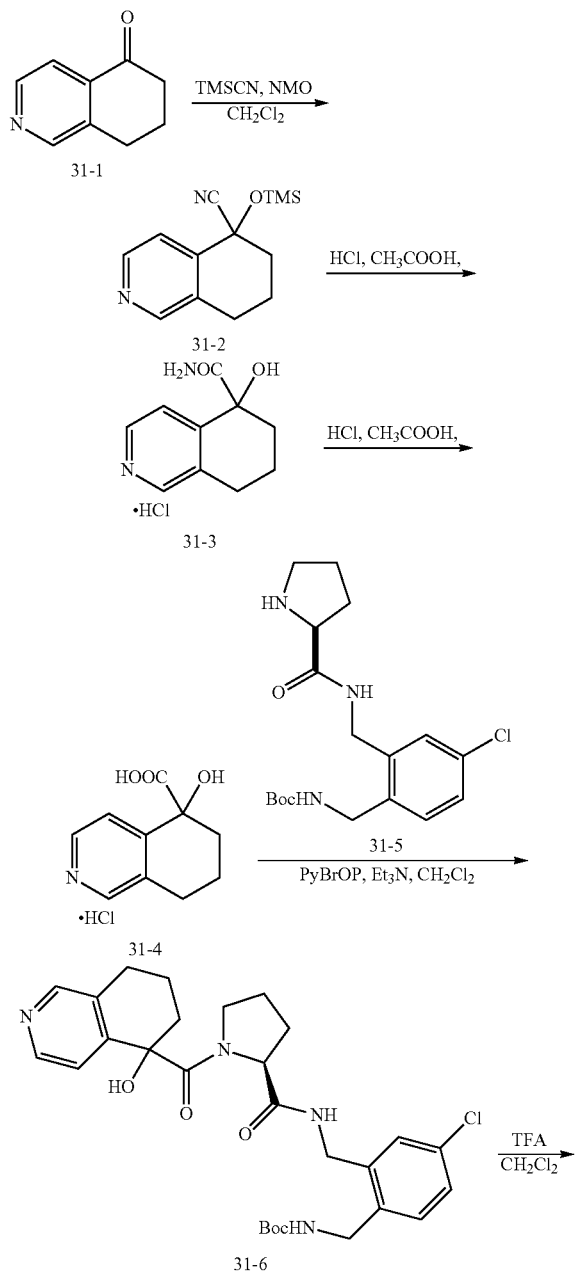

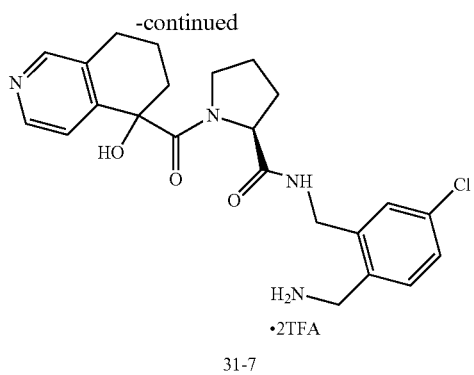

5-(Trimethylsilyloxy)-5,6,7,8-tetrahydroisoquinoline-5-carbonitrile (31-2)

NMO (0.54 g, 4.90 mmol) and TMSCN (0.9 mL, 7.40 mmol) was added to a solution of compound 31-1 (0.9 g, 4.90 mmol) in CH$_2$Cl$_2$ (20 mL) and mixture was stirred at room temperature for 2 h. The reaction was quenched with water (30 mL) and extracted with CH$_2$Cl$_2$ (100 mL). The combined organic layers were dried over anhydrous Na$_2$SO$_4$, filtered and concentrated under reduced pressure. The residue was purified by column chromatography (silica gel; 0-40% EtOAc/hexanes) to obtain cyanohydrin 31-2 as a colorless oil.

5-Hydroxy-5,6,7,8-tetrahydroisoquinoline-5-carboxamide (31-3)

To a stirred solution of compound 31-2 (0.98 g, 3.98 mmol) in acetic acid (10 mL) was added conc. HCl (15 mL) and mixture was stirred at room temperature for 16 h. The solvent was removed at reduced pressure and the residue was reprecipitated from EtOAc to obtain amide 31-3 as a yellow solid.

5-Hydroxy-5,6,7,8-tetrahydroisoquinoline-5-carboxylic acid (31-4)

A mixture of amide 31-3 (0.48 g, 2.09 mmol) in acetic acid (10 mL) and conc. HCl (15 mL) was stirred at 60° C. for 48 h. The solvent was removed at reduced pressure and residue was reprecipitated from EtOAc to obtain hydroxyl acid 31-4 as a yellow solid.

tert-Butyl-4-chloro-2-[{(2S)-1-(5-hydroxy-5,6,7,8-tetrahydroisoquinoline-5-carbonyl)pyrrolidine-2-carboxamido}methyl]benzylcarbamate (31-6)

PyBrOP (2.26 g, 4.87 mmol) was added to a mixture of hydroxyl acid 31-4 (0.56 g, 2.43 mmol), amine 31-5 (0.45 g, 1.22 mmol) and Et$_3$N (2.0 mL, 14.6 mmol) in CH$_2$Cl$_2$ (20 mL) at 5° C. The mixture was stirred at room temperature for 2 h. The reaction was quenched with 1% aqueous citric acid solution (50 mL) and extracted with CH$_2$Cl$_2$ (2×75 mL). The combined organic extracts were washed with saturated aqueous NaHCO$_3$ solution (50 mL), brine (50 mL), dried over anhydrous Na$_2$SO$_4$, filtered and concentrated under reduced pressure. The residue was purified by reverse phase column chromatography (C18; eluent: 10-100% acetonitrile/water) followed by semi-prep HPLC to obtain compound 31-6 as a hygroscopic solid (2S)-N-{2-(Aminomethyl)-5-chlorobenzyl}-1-(5-hydroxy-5,6,7,8-tetrahydroisoquinoline-5-carbonyl)pyrrolidine-2-carboxamide bis(2,2,2-trifluoroacetate) (31-7)

Trifluoroacetic acid (0.3 mL, 3.92 mmol) was added dropwise to a solution of Boc protected amine 31-6 (90 mg, 0.16 mmol) in CH$_2$Cl$_2$ (1 mL) and mixture was stirred at room temperature for 1 h. The solvent and volatiles were removed under reduced pressure and residue was purified by reverse phase combiflash column chromatography (C18; eluent: 10-100% acetonitrile/water) to obtain 31-7. $^1$H NMR (MeOD-d$_4$, 400 MHz) (δ) ppm: 8.62 (1H, s), 8.43-8.56 (1H, m), 7.86-7.88 (m, 1H), 7.33-7.57 (m, 3H), 4.20-4.57 (m, 5H), 3.85-3.99 (m, 1H), 3.51-3.74 (m, 1H), 3.40-3.48 (m, 1H), 2.90-3.03 (m, 2H), 2.33-2.44 (m, 1H), 2.19-2.25 (m, 1H), 1.76-2.10 (m, 5H).

EXAMPLE 32

Preparation of (2S)-N-{2-(aminomethyl)-5-chlorobenzyl}-1-(8-hydroxy-5,6,7,8-tetrahydroquinoline-8-carbonyl)pyrrolidine-2-carboxamide bis(2,2,2-trifluoroacetate) (32-7)

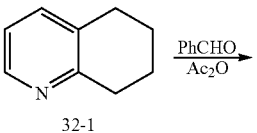

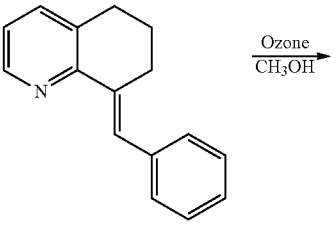

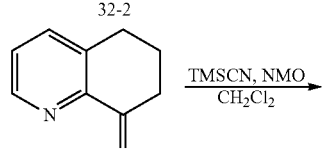

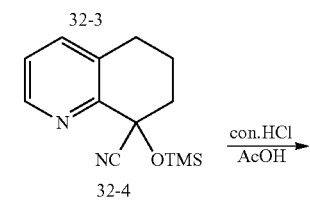

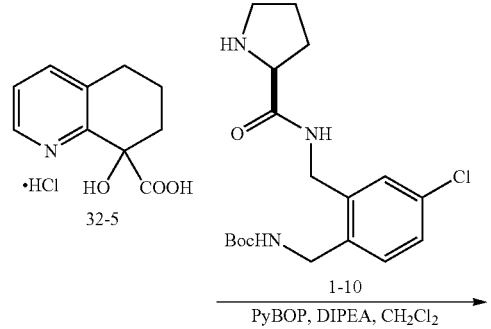

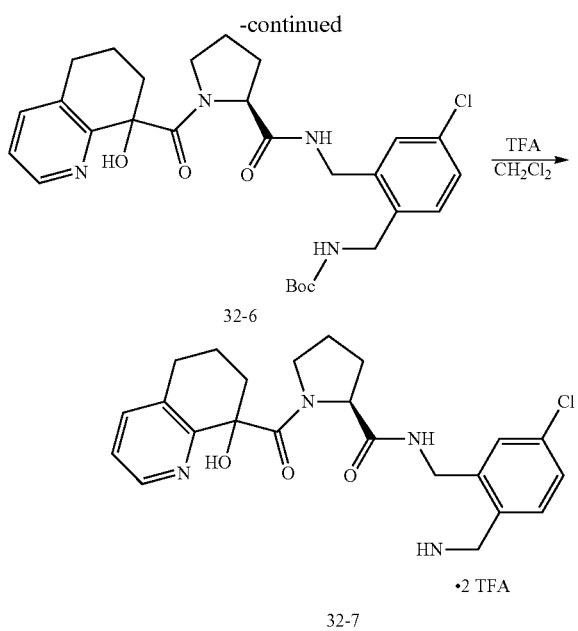

8-Benzylidene-5,6,7,8-tetrahydroquinoline (32-2)

A mixture of tetrahydroquinoline 32-1 (15.0 g, 112 mmol) and benzaldehyde (12.6 mL, 123 mmol) in acetic anhydride (25 mL) was heated at 170° C. for 18 h. The reaction mixture cooled to room temperature, neutralized to pH 7-8 with 2 N aqueous NaOH solution and extracted with EtOAc (3×200 mL). The combined organic layers were washed with brine (200 mL), dried over anhydrous $Na_2SO_4$ and concentrated under reduced pressure. The residue purified by combiflash chromatography (silica gel, 3:7 EtOAc/Hexanes) to afford intermediate 32-2 s dark brown oil.

6,7-Dihydroquinolin-8(5H)-one (32-3)

Ozone gas was purged through a solution of alkene 32-2 (10.0 g, 45.1 mmol) in $CH_3OH$ at −40° C. for 2 h. Dimethyl sulfide (12.6 mL, 270 mmol) was added to the mixture at −40° C. and reaction was slowly warmed to room temperature. After stirring for 2 h at room temperature, solvent was removed under reduced pressure. The residue purified by combiflash chromatography (silica gel, 1:1 EtOAc/Hexanes) to provide ketone 32-3 as light brown oil

8-{(Trimethylsilyl)oxy}-5,6,7,8-tetrahydroquinoline-8-carbonitrile (32-4)

Trimethylsilyl cyanide (2.94 mL, 21.9 mmol) was added dropwise to the mixture of dihydroquinolinone 32-3 (2.15 g, 14.6 mmol) and N-methylmorpholine-N-oxide (0.51 g, 4.38 mmol) in $CH_2Cl_2$ (30 mL) and reaction mixture was stirred under nitrogen for 2 h. The reaction quenched with aqueous $NH_4Cl$ solution (30 mL) and extracted with $CH_2Cl_2$ (2×50 mL). The combined organic extracts were washed with brine (50 mL), dried over anhydrous $Na_2SO_4$ and concentrated under reduced pressure. The residue purified by combiflash chromatography (silica gel, 1:5 EtOAc/Hexanes) to provide cycanohydrin 32-4 as brown oil.

8-Hydroxy-5,6,7,8-tetrahydroquinoline-8-carboxylic acid hydrochloride (32-5)

A mixture of cyanohydrin 32-4 (0.50 g, 2.17 mmol), conc HCl (5 mL) and acetic acid (5 mL) was refluxed for 24 h. The reaction mixture cooled to room temperature and concentrated under reduced pressure. The residue was azeotroped with toluene (2×10 mL) and dried under high vacuum to provide the hydroxy acid 32-5 as brown solid.

tert-Butyl-4-chloro-2-[{(2S)-1-(8-hydroxy-5,6,7,8, tetrahydro quino-line-8-carbonyl) pyrrolidine-2-carboxamido}methyl]benzylcarbamate (32-6)

DIPEA (0.24 mL, 1.30 mmol) was added to a suspension of hydrochloride salt 32-5 (0.10 g 0.43 mmol) in $CH_2Cl_2$ (10 mL) and stirred for 10 min. Thereafter, the amine 1-10 (0.17 g, 0.47 mmol) and PyBOP (0.24 g, 0.43 mmol) was added and mixture was stirred under nitrogen for 24 h. The solvent was removed under reduced pressure and the residue purified by reverse phase combiflash chromatography (C18, 1:4 $H_2O/CH_3CN$) to provide the amide 32-6 as colorless oil.

(2S)-N-{2-(Aminomethyl)-5-chlorobenzyl}-1-(8-hydroxy-5,6,7,8-tetrahydroquinoline-8-carbonyl) pyrrolidine-2-carboxamide bis(2,2,2-trifluoroacetate) (32-7)

A 50% solution Trifluoroacetic acid (6 mL) in $CH_2Cl_2$ (1 mL) was added to the solution of Boc protected 32-6 (0.10 g, 0.18 mmol) in $CH_2Cl_2$ (2 mL) and reaction mixture was stirred under nitrogen for 2 h. The solvent was removed at reduced pressure and the residue was azeotroped with toluene (6 mL). Hygroscopic solid was dissolved in 1:1 acetonitrile/water (3 mL) and lyophilized for 24 h to obtain 32-7. $^1H$ NMR (300 MHz, MeOD-$d_4$) δ 8.41 (d, J=5.10 Hz, 1H), 8.13 (d, J=8.10 Hz, 1H), 7.73-7.60 (m, 1H), 7.56-7.34 (m, 3H), 4.60-4.40 (m, 3H), 4.35-3.80 (m, 4H), 3.45-3.35 (m, 1H), 3.10-2.85 (m, 2H), 2.60-2.40 (m, 1H), 2.32-2.12 (m, 1H), 2.11-1.72 (m, 4H), 1.43-1.26 (m, 1H).

EXAMPLE 33

Preparation of (2S)-N-{2-(Aminomethyl)-5-chlorobenzyl}-1-(1,3-dihydroisobenzofuran-1-carbonyl) azetidine-2-carboxamide-2,2,2-trifluoroacetate (33-7)

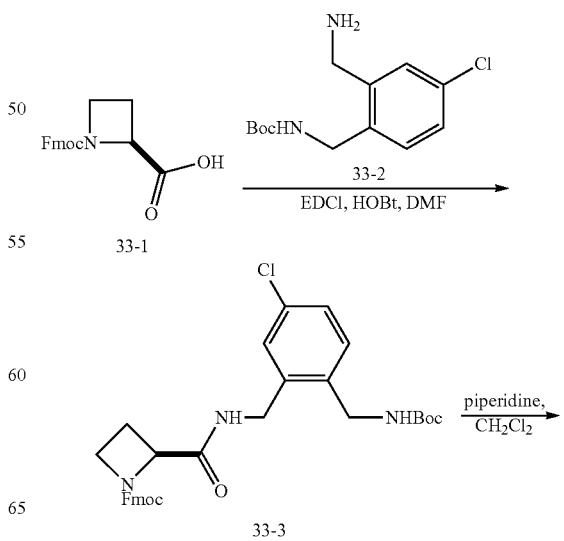

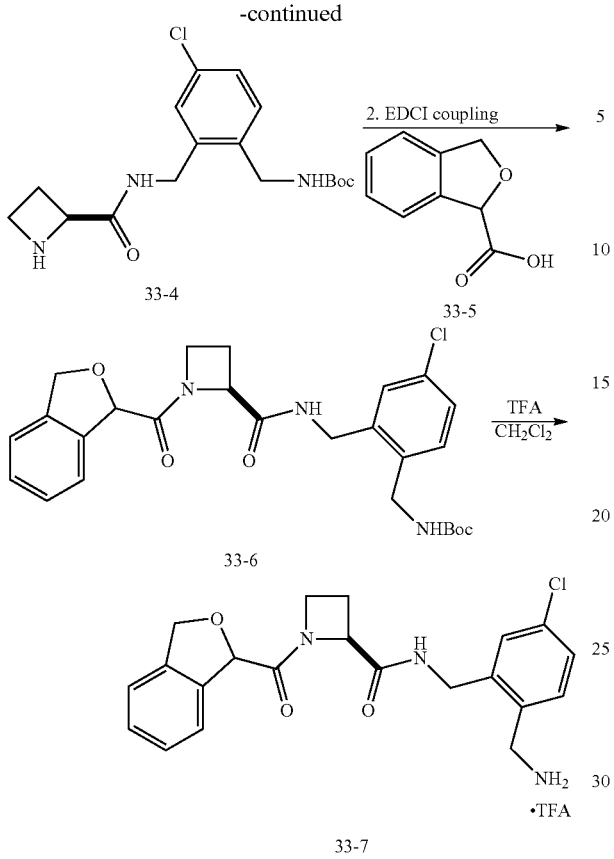

(9H-Fluoren-9-yl)methyl 2-{(2-[{(tert-butoxycarbonyl)amino}methyl]-5-chlorobenzyl)carbamoyl}azetidine-1-carboxylate (33-3)

Amine 33-2 (1.17 g, 3.09 mmol) was added to a solution of acid 33-1 (1.0 g, 3.09 mmol), EDCI (1.17 g, 6.18 mmol), and HOBt (0.85 g, 6.18 mmol) in DMF (10 mL) at 0° C. The reaction mixture was stirred at room temperature for 1 h. The mixture diluted with water (30 mL) and extracted with EtOAc (2×50 mL). The combined organic layers were washed with saturated NaHCO₃ solution (20 mL), 0.5 M aqueous HCl (20 mL), brine solution (20 mL), dried over anhydrous Na₂SO₄, filtered and concentrated under reduced pressure. The residue was purified by column chromatography (silica gel: 50% EtOAc/Hexanes) to obtain amide 33-3 as a yellow semi solid.

(S)-tert-Butyl 2-{(azetidine-2-carboxamido)methyl}-4-chlorobenzylcarbamateamate (33-4)

Piperidine (0.6 mL) was added to a solution of amide 33-3 (0.57 g, 0.99 mmol) in CH₂Cl₂ (6 mL) at 0° C. and the reaction mixture was stirred at room temperature for 1 h. The reaction mixture was concentrated to dryness and the residue was purified by reverse phase combiflash chromatography (C18; 10-100% acetonitrile/water) to obtain amine 33-4 as a white solid.

tert-Butyl 4-chloro-2-[{(2S)-1-(1,3-dihydroisobenzofuran-1-carbonyl)azetidine-2-carboxamido}methyl]benzylcarbamate (33-6)

Amine 33-4 (0.20 g, 0.58 mmol) was added to a solution of acid 33-5 (0.07 g, 0.42 mmol), EDCI (0.17 g, 0.84 mmol), HOBt (0.12 g, 0.84 mmol) in DMF (4 mL) at 0° C. and the reaction mixture was stirred at room temperature for 2 h. The reaction mixture diluted with water (20 mL) and extracted with EtOAc (2×50 mL). The combined organic layers were washed with saturated aqueous NaHCO₃ solution (10 mL), 0.5M aqueous HCl (10 mL), brine solution (20 mL), dried over anhydrous Na₂SO₄, filtered and concentrated under reduced pressure. The residue was purified by column chromatography (silica gel: 40% EtOAc/Hexanes) to get amide 33-6 as a light brown solid.

(2S)-N-{2-(Aminomethyl)-5-chlorobenzyl}-1-(1,3-dihydroisobenzofuran-1-carbonyl)azetidine-2-carboxamide-2,2,2-trifluoroacetate (33-7)

A 50% solution of TFA in CH₂Cl₂ (3 mL) was added to a solution of Boc protected amine 6 (0.19 g, 0.38 mmol) in CH₂Cl₂ (1 mL) and the reaction was stirred at 0° C. for 30 min. The reaction mixture was concentrated under reduced pressure and the residue was purified by reverse phase combiflash chromatography (C18; 10-100% acetonitrile/water) to get 33-7 as a white hygroscopic solid. ¹HNMR (CDCl₃, 1:1 mixture of diastereomers, 400 MHz) (δ) ppm: 8.94-8.89 (m, 1H), 8.88-8.20 (brs, 3H), 7.45-7.20 (m, 7H), 5.70 (s, 0.5H), 5.63 (s, 0.5H), 5.2-5.16 (m, 2H), 4.84-4.66 (m, 2H), 4.62-4.43 (m, 1H), 4.17-4.40 (m, 4H), 2.52-2.32 (m, 2H).

EXAMPLE 34

Preparation of (2S)-N-{2-(aminomethyl)-5-chlorobenzyl}-1-(isoindoline-1-carbonyl)azetidine-2-carboxamide bis(2,2,2-trifluoroacetate) (34-7)

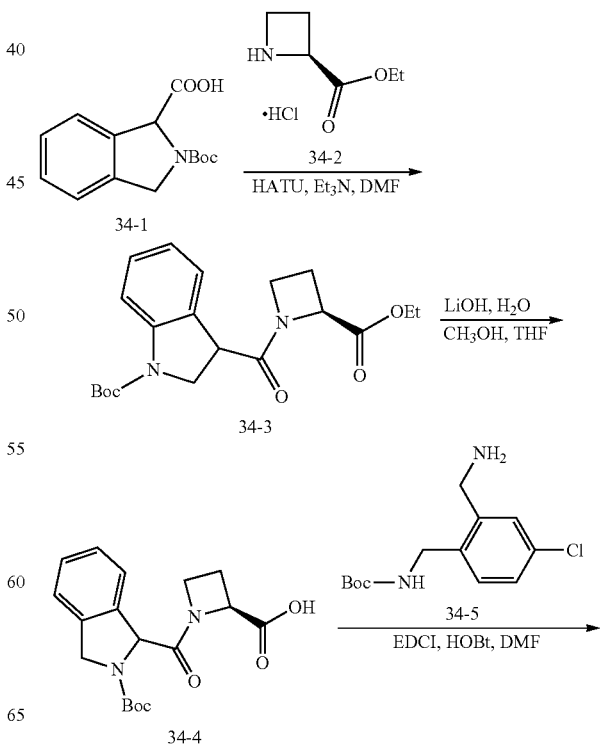

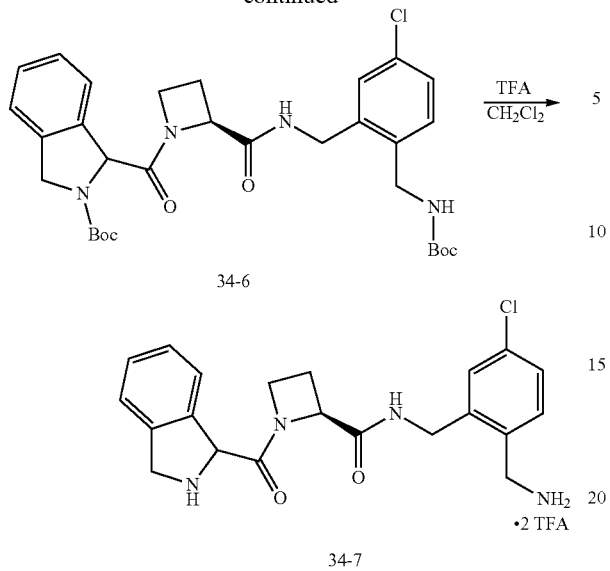

tert-Butyl-3-{(S)-2-(ethoxycarbonyl)azetidine-1-carbonyl}indoline-1-carboxylate (34-3)

A mixture of acid 34-1 (300 mg, 1.14 mmol), amine 34-2 (188 mg, 1.14 mmol), HATU (646 mg, 1.71 mmol) and DIPEA (0.77 mL, 4.57 mmol) in DMA (10 mL) was stirred at room temperature for 2 h. The solvent was removed at reduced pressure and residue was purified by reverse phase combiflash (C18; 10-100% acetonitrile/water) to provide amide 34-3 as a colorless gum.

(2S)-1-{2-(tert-Butoxycarbonyl)isoindoline-1-carbonyl}azetidine-2-carboxylic acid (34-4)

A solution of LiOH (64 mg, 2.80 mmol) in water (1 mL) was added dropwise to the solution of amide 34-3 (350 mg, 0.93 mmol) and the reaction mixture was stirred at room temperature for 4 h. The organic solvent was removed under reduced pressure and the mixture was diluted with water (10 mL). The aqueous layer was washed with MTBE (20 mL), acidified with 10% aqueous KHSO₄ to pH 2 and extracted with EtOAc (3×20 mL). The combined organic extract was dried over anhydrous Na₂SO₄, filtered and concentrated to provide acid 34-4 as an off white solid.

tert-Butyl-1-{(S)-2-{(2-[{(tert-butoxycarbonyl)amino}methyl]-5-chlorobenzyl)carbamoyl}azetidine-1-carbonyl)isoindoline-2-carboxylate (34-6)

A mixture of acid 34-4 (301 mg, 0.86 mmol), amine 34-5 (281 mg, 1.04 mmol), EDC (198 mg, 1.04 mmol), and HOBt (140 mg, 1.04 mmol) in DMA (10 mL) was stirred at room temperature for 4 h. The reaction was quenched with water (20 mL) and extracted with EtOAc (3×20 mL). The combined organic extract was dried over anhydrous Na₂SO₄, filtered and concentrated. The residue was purified by combiflash (silica gel; eluent: 30% EtOAc/hexanes) to provide non polar diasteromer 34-6a and polar diasteromer 34-6b as a colorless gum.

(2S)-N-{2-(Aminomethyl)-5-chlorobenzyl}-1-(isoindoline-1-carbonyl)azetidine-2-carboxamide bis(2,2,2-trifluoroacetate) (34-7a)

A 50% solution of TFA in CH₂Cl₂ (3 mL) was added to the stirred solution of Boc protected amino 34-6a (58 mg, 0.096 mmol) and the reaction mixture was stirred at room temperature for 3 h. The solvent was removed under reduced pressure and the residue was azeotroped with toluene (2×20 mL) and dried over high vacuum pump for 2 h. The crude product was purified by reverse phase combiflash (C18; eluent: 30% acetonitrile/water) to provide 34-7a. $^1$H NMR (MeOD, 400 MHz) (δ) ppm: 7.53-7.29 (m, 7H), 5.68-5.49 (m, 1H), 4.98-4.12 (m, 10H), 2.81-2.72 (m, 1H), 2.41-2.32 (m, 1H).

(2S)-N-{2-(Aminomethyl)-5-chlorobenzyl}-1-(isoindoline-1-carbonyl)azetidine-2-carboxamide bis(2,2,2-trifluoroacetate) (34-7b)

A 50% solution of TFA in CH₂Cl₂ (5 mL) was added to the stirred solution of Boc protected amino 34-6b (110 mg, 0.18 mmol) and the reaction mixture was stirred at room temperature for 3 h. The solvent was removed at reduced pressure and residue was azeotroped with toluene (2×20 mL) and dried over high vacuum pump for 2 h. The crude product was purified by reverse phase combiflash (30% acetonitrile/water) to provide 34-7b. $^1$H NMR (MeOD, 400 MHz) (δ) ppm: 7.58-7.33 (m, 7H), 5.69-5.54 (m, 1H), 4.98-4.95 (m, 1H), 4.72 (dd, J=14.4 Hz, J=44 Hz, 2H), 4.63-4.52 (m, 2H), 4.52-4.12 (m, 4H), 2.826-2.67 (m, 1H), 2.51-2.20 (m, 1H).

EXAMPLE 35

Preparation of (2S)-N-{2-(Aminomethyl)-5-chlorobenzyl}-1-(indoline-3-carbonyl)azetidine-2-carboxamide bis(2,2,2-trifluoroacetate) (35-7)

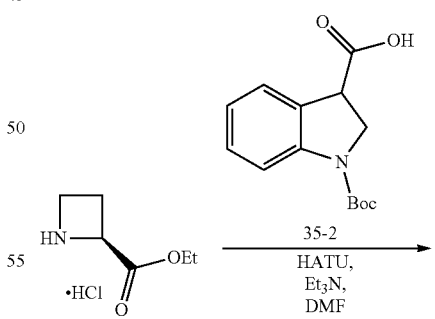

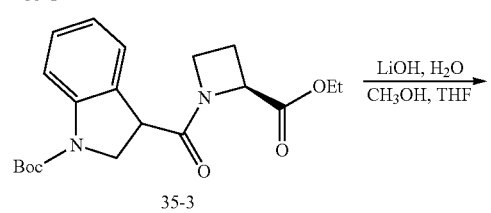

111

-continued

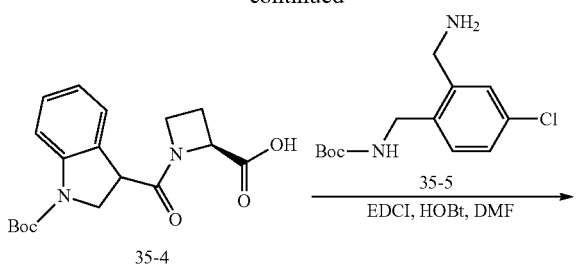

tert-Butyl-3-{(S)-2-(Ethoxycarbonyl)azetidine-1-carbonyl}indoline-1-carboxylate (35-3)

Triethylamine (1.48 mL, 10.5 mmol) was added to a mixture of amine hydrochloride salt 35-1 (0.35 g, 2.11 mmol), acid 35-2 (0.44 g, 1.68 mmol) and HATU (1.60 g, 4.22 mmol) and the mixture was stirred under nitrogen for 3 h. The reaction mixture was quenched with water (100 mL) and extracted with EtOAc (3×30 mL). The combined organic layers were washed with water (2×100 mL), brine (50 mL), dried over anhydrous $Na_2SO_4$, and concentrated under reduced pressure. The residue was purified by reverse phase combiflash chromatography (C18, 1:4 water/$CH_3CN$) to afford 35-3 as an oil.

(2S)-1-[1-(tert-Butoxycarbonyl)indoline-3-carbonyl]azetidine-2-carboxylic acid (35-4)

A solution of LiOH·$H_2O$ (0.09 g, 2.16 mmol) in $H_2O$ (2 mL) was added to a stirred solution of ester 35-3 (0.27 g, 0.72 mmol) in $CH_3OH$/THF (6 mL, 1:1) and the reaction mixture stirred at room temperature for 3 h. The solvent was removed at reduced pressure and mixture was diluted with water (10 mL), acidified to pH 3-4 with aqueous $KHSO_4$ solution and extracted with EtOAc (2×20 mL). The combined organic layer were washed with brine (10 mL), dried over anhydrous $Na_2SO_4$ and concentrated to provide the acid 35-4 as an off-white solid.

112 tert-Butyl 3-{(S)-2-{(2-[{(tert-butoxycarbonyl)amino}methyl]-5-chlorobenzyl)carbamoyl}azetidine-1-carbonyl}indoline-1-carboxylate (35-6)

A mixture of acid 35-4 (0.19 g, 0.54 mmol), amine 35-5 (0.20 g, 0.54 mmol), EDCI (0.11 g, 0.60 mmol and HOBt (0.02 g, 0.13 mmol) in DMF (10 mL) was stirred under nitrogen for 3 h at room temperature. The reaction was diluted with water (100 mL) and extracted with EtOAc (3×20 mL). The combined organic layers were washed with water (2×100 mL), brine (50 mL), dried over anhydrous $Na_2SO_4$ and concentrated under reduced pressure. The residue was purified by reverse phase combiflash chromatography (C18, 1:3 water/$CH_3CN$) to afford 35-6 as a colorless oil.

(2S)-N-{2-(Aminomethyl)-5-chlorobenzyl}-1-(8-hydroxy-5,6,7,8-tetrahydroquinoline-8-carbonyl)pyrrolidine-2-carboxamide bis(2,2,2-trifluoroacetate) (35-7)

A 50% solution of TFA in $CH_2Cl_2$ (10 mL) was added to the solution of 35-6 (0.25 g, 0.41 mmol) in $CH_2Cl_2$ (2 mL) and the reaction mixture was stirred under nitrogen for 2 h. The solvent was removed under reduced pressure and the residue was azeotroped with toluene (2×10 mL). The resulting hygroscopic solid was dissolved in 1:1 acetonitrile/water (4 mL) and lyophilized for 24 h to obtain 35-7. $^1$H NMR (300 MHz, MeOD) δ 7.43 (s, 1H), 7.39 (d, J=10.8 Hz, 2H), 7.14-6.93 (m, 2H), 6.72-6.60 (m, 2H), 4.82 (brs, 1H), 4.60-4.45 (m, 1H), 4.42-4.37 (m, 2H), 4.27-4.05 (m, 4H), 3.71-3.59 (m, 2H), 2.66-2.45 (m, 1H), 2.45-2.20 (m, 1H)

EXAMPLE 36

Preparation of (2S)-N-{5-Chloro-2-(1H-tetrazol-1-yl)benzyl}-1-(7-hydroxy-6,7-dihydro-5H-cyclopenta[b]pyridine-7-carbonyl)pyrrolidine-2-carboxamide (36-3)

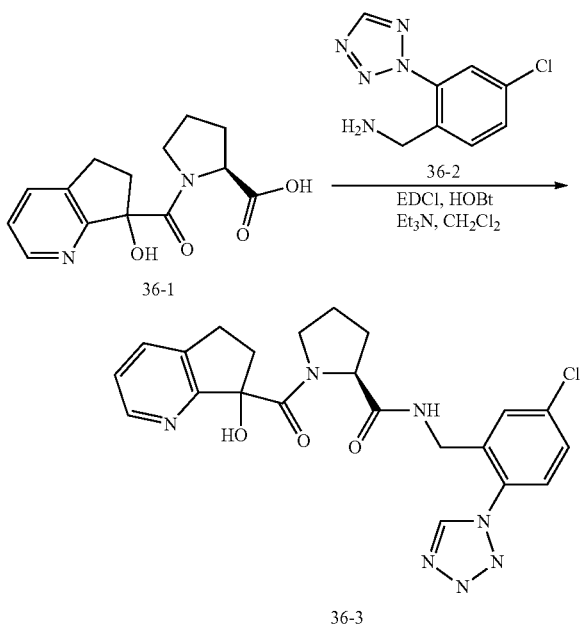

(2S)-N-{5-Chloro-2-(1H-tetrazol-1-yl)benzyl}-1-(7-hydroxy-6,7-dihydro-5H-cyclopenta[b]pyridine-7-carbonyl)pyrrolidine-2-carboxamide (36-3)

A mixture of acid 36-1 (0.07 g, 0.253 mmol), amine 36-2 (0.053 g, 0.253 mmol), triethyl amine (0.03 mL, 0.253 mmol), EDCI (0.058 g, 0.304 mmol), and HOBt (0.041 g, 0.304 mmol) in CH$_2$Cl$_2$ (5 mL) was stirred at room temperature for 16 h. The reaction was quenched with aqueous saturated NaHCO$_3$ solution (5 mL) and extracted with CH$_2$Cl$_2$ (2×15 mL). The combined organic layers were washed with water (15 mL), brine (15 mL), dried over anhydrous Na$_2$SO$_4$, filtered and concentrated under reduced pressure. The residue was purified by reverse phase flash chromatography (C18; eluent: 10%-40% water/acetonitrile) to afford 36-3. $^1$H NMR (MeOD-d$_4$, 400 MHz) (δ) ppm: 9.16 (s, 1H), 9.03 (s, 1H), 8.41 (d, J=4.4 Hz, 1H), 8.33 (t, J=4.4 Hz, 1H), 8.16 (d, J=4.4 Hz, 1H), 7.74 (d, J=2.4 Hz, 1H), 7.69 (d, J=7.6 Hz, 1H), 7.62 (d, J=7.6 Hz, 1H), 7.54 (d, J=2.4 Hz, 1H), 8.3 (t, J=4.4 Hz, 1H), 7.41 (t, J=4.0 Hz, 1H), 7.22-7.27 (m, 3H), 7.19 (dd, J=4.8 Hz, 7.6 Hz, 1H), 5.27 (s, 1H), 4.90 (s, 1H), 4.77 (dd, J=8.0 Hz, J =13.2 Hz, 1H), 4.66 (dd, J=3.6 Hz, J=7.6 Hz, 1H), 4.34 (dd, J=6.4 Hz, J=15.6 Hz, 1H), 4.16-4.23 (m, 3H), 3.34-3.43 (m, 2H), 3.15-3.31 (m, 2H), 3.0-3.08 (m, 2H), 2.61-2.79 (m, 2H), 2.42-2.42 (m, 3H), 2.05-2.09 (m, 4H), 1.92-1.94 (m, 2H), 1.30-1.41 (m, 3H).

EXAMPLE 37

Preparation of (5)-N-{2-(Aminomethyl)-5-chlorobenzyl}-1-{(R)-1-hydroxy-2,2-dimethylcyclopropanecarboxamide-2,2,2-trifluoroacetate (37-11)

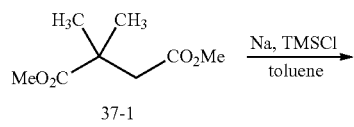

37-1

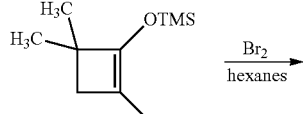

37-2

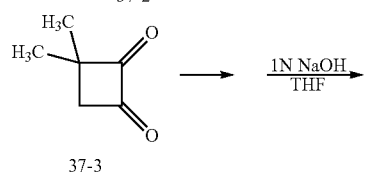

37-3

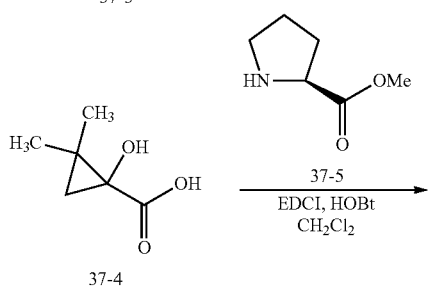

37-4

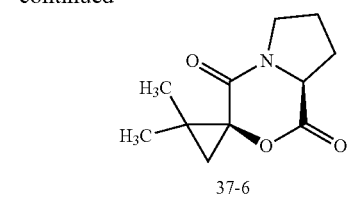

37-6

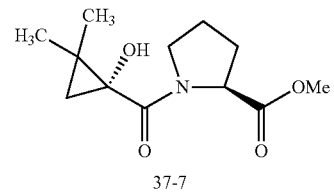

37-7

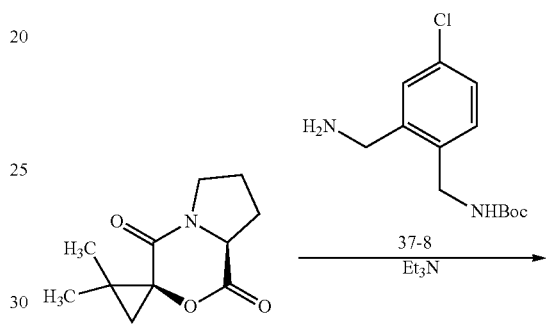

37-6

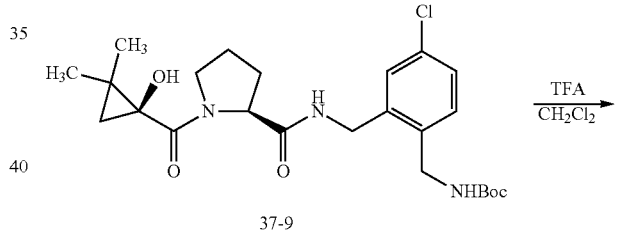

37-9

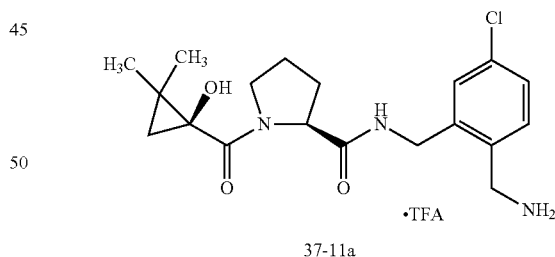

37-11a

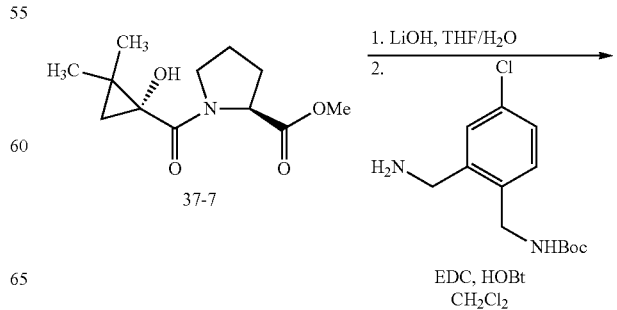

37-7

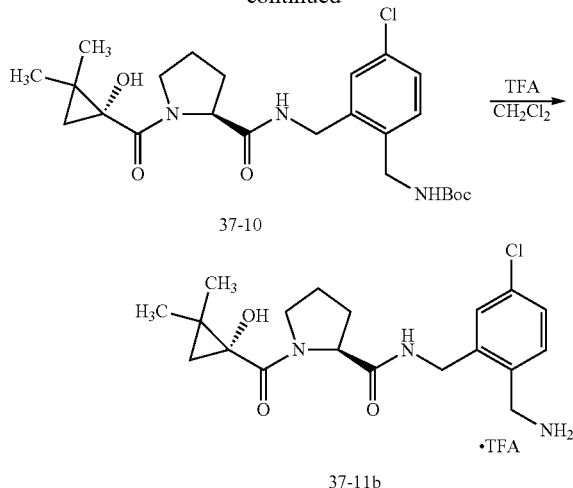

37-10

37-11b

{(3,3-Dimethylcyclobut-1-ene-1,2-diyl)bis(oxy)}bis(trimethylsilane) (37-2)

A solution of dimethyl-2,2-dimethylsuccinate 37-1 (5.0 g, 28.57 mmol) and TMSCl (15.0 mL, 116.1 mmol) in toluene (20 mL) was added dropwise to a suspension of sodium metal (2.6 g, 114.2 mmol) in anhydrous toluene (50 mL) under nitrogen atmosphere over a period of 1 h and the mixture was refluxed for 36 h. The reaction mixture was allowed to cool to room temperature, the mixture was filtered through a pad of celite and concentrated under reduced pressure to obtain cyclobutene 37-2 as a colorless oil. The crude residue was used for next step without any further purification.

1-Hydroxy-2,2-dimethylcyclopropanecarboxylic acid (37-4)

Bromine (1 mL, 18.3 mmol) was added dropwise to a solution of intermediate 37-2 (4.20 g, 16.86 mmol) in a hexanes/pentane (1:1, 30 mL) and the reaction mixture was stirred at 45° C. for 1 h. The reaction mixture was concentrated under reduced pressure and the residue was used without purification. 1N aqueous NaOH solution (10 mL) was added to the solution of the above residue (2.33 g, 20.33 mmol) in THF (20 mL) and mixture was stirred at room temperature for 2 h. Solvent was removed at reduced pressure; residue was dissolved in water (10 mL) and acidified with 2M aqueous HCl to pH 4-5. The aqueous layer extracted with EtOAc (3×30 mL). The combined organic layer was dried over anhydrous $Na_2SO_4$, filtered and concentrated under reduced pressure to get acid 37-4 as a pale yellow solid.

(1S,8a'S)-2,2-Dimethyltetrahydrospiro[cyclopropane-1,3'-pyrrolo[2,1-c][1,4]oxazine]-1',4'-dione (37-6) and (S)-methyl 1-{(R)-1-hydroxy-2,2-dimethylcyclopropanecarbonyl}pyrrolidine-2-carboxylate (37-7)

The mixture of acid 37-4 (0.2 g, 1.54 mmol), amine 37-5 (0.2 g, 1.23 mmol), EDCI (0.59 g, 3.07 mmol), HOBt (0.41 g, 3.07 mmol) and DIPEA (0.6 mL, 3.07 mmol) in $CH_2Cl_2$ (3 mL) was stirred at room temperature for 14 h. The reaction mixture was diluted with $CH_2Cl_2$ (20 mL), washed with saturated $NaHCO_3$ solution (10 mL) and 0.5 M HCl (10 mL) successively. The organic layer was separated and washed with brine solution (10 mL), dried over anhydrous $Na_2SO_4$, filtered and concentrated under reduced pressure. The residue was purified by silica gel column chromatography (eluent: 40% EtOAc/hexanes) to obtain lactone 37-6 as a white solid (0.1 g, 31%) and amide 37-7 as a colorless semi solid.

tert-Butyl 4-chloro-2-[{(S)-1-{(S)-1-hydroxy-2,2-dimethylcyclopropanecarbonyl}-pyrrolidine-2-carboxamido}methyl]benzylcarbamate (37-9)

Triethylamine (3 mL) was added to a solution of lactone 37-6 (0.1 g, 0.48 mmol) and Boc protected amine 37-8 (0.15 g, 0.51 mmol) in $CH_2Cl_2$ (2 mL) and the reaction mixture was stirred at room temperature for 72 h. The reaction mixture was concentrated to dryness and the residue was purified by silica gel column chromatography (eluent: 60% EtOAc/hexanes) to afford amide 37-9 as a pale yellow semi solid.

(S)—N-(2-(Aminomethyl)-5-chlorobenzyl)-1-((S)-1-hydroxy-2,2-dimethylcyclopropanecarbonyl)pyrrolidine-2-carboxamide 2,2,2-trifluoroacetate (37-11a)

A 50% solution of TFA in $CH_2Cl_2$ (4 mL) was added to the solution of Boc protected amine 37-9 (0.18 g, 0.37 mmol) in $CH_2Cl_2$ (2 mL) and the reaction mixture was stirred at 0° C. for 30 min. The reaction mixture was concentrated under reduced pressure and residue was triturated with diethyl ether to afford amine salt 37-11a as a white hygroscopic solid. $^1$HNMR (400 MHz, DMSO-$d_6$): 8.46 (t, J=5.2 Hz, 1H), 8.15 (brs, 3H), 7.57-7.49 (m, 1H), 7.39-7.33 (m, 2H), 6.0 (brs, 1H), 4.44-4.27 (m, 3H), 4.14-4.02 (m, 3H), 3.99-3.88 (m, 1H), 2.11-1.73 (m, 4H), 1.15 (s, 3H), 1.98 (d, J=4.4 Hz, 1H), 0.84 (s, 3H), 0.38 (d, J=4.4 Hz, 1H).

tert-Butyl 4-chloro-2-[{(S)-1-{(R)-1-hydroxy-2,2-dimethylcyclopropanecarbonyl}pyrrolidine-2-carboxamido}methyl]benzylcarbamate (37-10)

A solution of LiOH·$H_2O$ (0.25 g, 1.28 mmol) in water (2 mL) was added to the solution of ester 37-7 (0.71 g, 3.70 mmol) in THF (3 mL) at 0° C. and the reaction mixture was stirred at room temperature for 4 h. Solvent was removed at reduced pressure and the residue was dissolved in water (10 mL) and acidified with 2M aqueous HCl to pH 4-5. The aqueous layer extracted with EtOAc (3×30 mL). The combined organic layer was dried over anhydrous $Na_2SO_4$, filtered and concentrated under reduced pressure to obtain acid as a colorless liquid.

The mixture of acid (0.14 g, 0.63 mmol), amine 37-8 (0.17 g, 0.63 mmol), EDCI (0.24 g, 1.26 mmol), and HOBt (0.17 g, 1.26 mmol) in $CH_2Cl_2$ (4 mL) was stirred at 0° C. and the reaction mixture was stirred at room temperature for 14 h. The mixture was diluted with $CH_2Cl_2$ (20 mL), washed with saturated $NaHCO_3$ solution (10 mL) and 0.5 N HCl (10 mL) successively. The organic layer was separated and washed with brine (10 mL), dried over anhydrous $Na_2SO_4$, filtered and concentrated under reduced pressure. The residue was purified by silica gel column chromatography (eluent: 60% EtOAc/hexanes) to obtain 37-10 as pale yellow semi solid.

(S)-{2-(Aminomethyl)-5-chlorobenzyl)-1-{(R)-1-hydroxy-2,2-dimethylcyclopropanecarbonyl}pyrrolidine-2-carboxamide-2,2,2-trifluoroacetate (37-11b)

A 50% solution of TFA in $CH_2Cl_2$ (2 mL) was added to the solution of 37-10 (0.13 g, 0.50 mmol) in $CH_2Cl_2$ (1 mL)

and reaction was stirred at 0° C. for 30 min. The reaction mixture was concentrated under reduced pressure and residue was triturated with diethyl ether to provide amine salt 37-11b as an off-white hygroscopic solid. ¹HNMR (400 MHz, CD₃CN): 8.27 (t, J=5.2 Hz, 1H), 8.02 (bs, 3H), 7.47 (d, J=1.6 Hz, 1H), 7.43 (d, J=8.4 Hz, 1H), 7.33 (dd, J=8.0 Hz, J=2.0 Hz, 1H), 5.85 (brs, 1H), 4.49 (dd, J=14.8 Hz, 6.0 Hz, 1H), 4.35-4.16 (m, 4H), 3.90-3.83 (m, 1H), 3.62-3.58 (m, 1H), 2.21-2.16 (m, 1H), 1.98-1.96 (m, 1H), 1.90-1.73 (m, 2H), 1.24 (s, 3H), 1.11 (d, J=5.2 Hz, 1H), 0.89 (s, 3H), 0.50 (d, J=5.2 Hz, 1H).

EXAMPLE 38

Preparation of (S)—N{2-(Aminomethyl)-5-chlorobenzyl}-1-{(R)-tetrahydrofuran-2-carbonyl}pyrrolidine-2-carboxamide-2,2,2-trifluoroacetate (38-4)

anhydrous Na₂SO₄, filtered and concentrated under reduced pressure. The residue was purified by silica gel column chromatography (silica gel; eluent: 10% MeOH/CH₂Cl₂) to get amide 38-3 as off-white solid.

(S)—N-{2-(Aminomethyl)-5-chlorobenzyl}-1-{(R)-tetrahydrofuran-2-carbonyl}pyrrolidine-2-carboxamide-2,2,2-trifluoroacetate (38-4)

Trifluoroacetic acid (50% solution in CH₂Cl₂, 3 mL) was added to Boc protected amine 38-3 (80.0 mg, 0.17 mmol) in CH₂Cl₂ (1 mL) and reaction was stirred at 0° C. for 1 h. The solvent and volatiles were removed under reduced pressure and the residue was purified by reverse phase combiflash chromatography (C18; 10-100% acetonitrile/water) to obtain 38-4. ¹H NMR (DMSO-d₆, 300 MHz) (δ) ppm: 8.49-8.88 (m, 1H), 8.12 (brs, 3H), 7.39-7.43 (d, J=12.0 Hz, 3H), 4.34-4.57 (m, 1H), 4.15-4.32 (m, 2H), 3.80-4.12 (m, 2H), 3.49-3.77 (m, 3H), 3.42-3.48 (m, 2H), 1.68-2.10 (m, 8H).

EXAMPLE 39

Preparation of (S)—N-{2-(Aminomethyl)-5-chlorobenzyl}-1-(5-ethoxy-1H-pyrrole-2-carbonyl)pyrrolidine-2-carboxamide-2,2,2-trifluoroacetate (39-10)

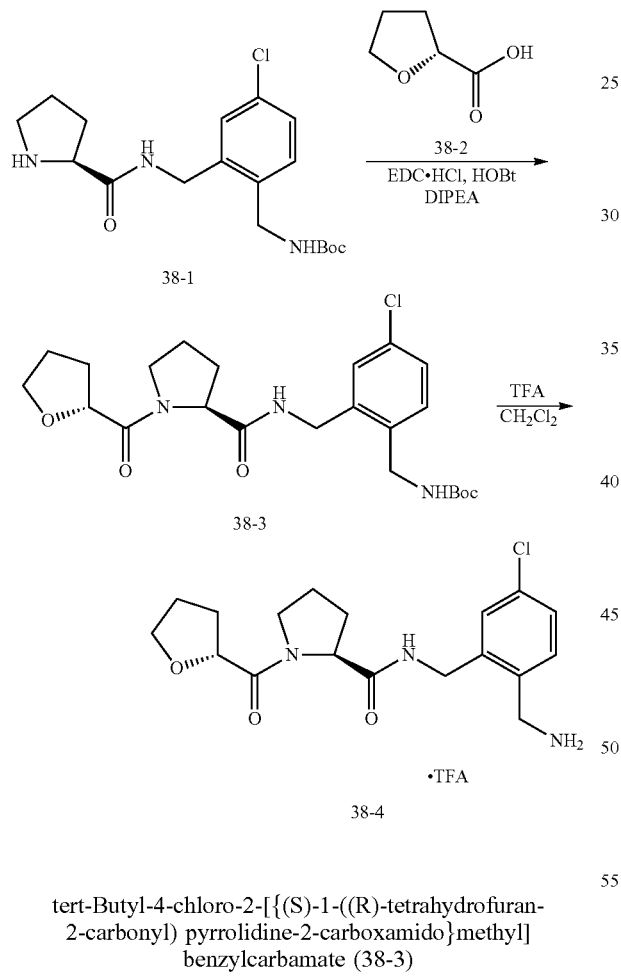

tert-Butyl-4-chloro-2-[{(S)-1-((R)-tetrahydrofuran-2-carbonyl) pyrrolidine-2-carboxamido}methyl] benzylcarbamate (38-3)

A mixture of acid 38-2 (31.3 mg, 0.42 mmol), EDCI (61.1 mg, 0.32 mmol), HOBt (33.1 g, 0.24 mmol), DIPEA (0.5 mL, 0.28 mmol) and amine 38-1 (90 mg, 0.24 mmol) in DMF (5 mL) was stirred at room temperature for 2 h. The mixture was diluted with water (100 mL) and extracted with EtOAc (3×100 mL). The combined organic extracts were washed with saturated NaHCO₃ solution (20 mL), 1N aqueous HCl (20 mL), brine solution (20 mL), dried over

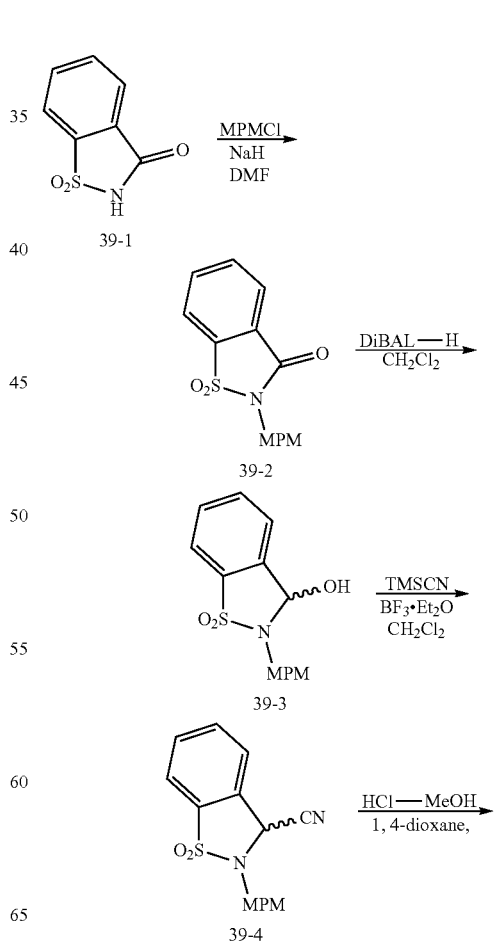

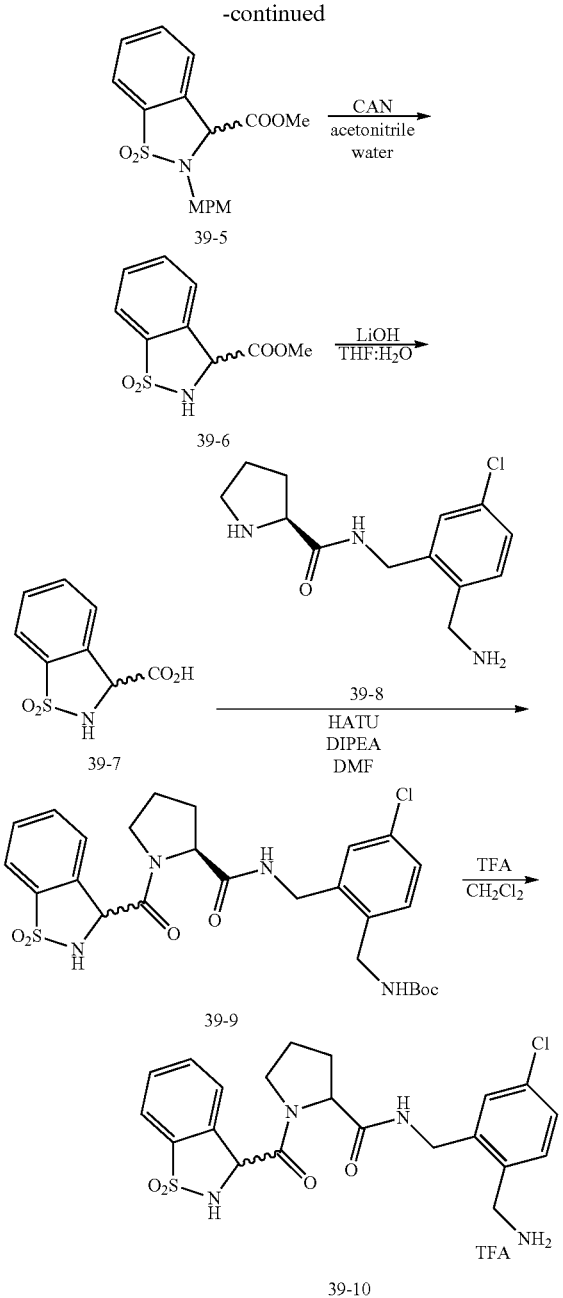

2-(4-Methoxybenzyl)benzo[d]isothiazol-3(2H)-one 1,1-dioxide (39-2)

A solution of saccharin (5.0 g, 27.3 mmol) in DMF (20 mL) was added drop wise to the mixture of NaH (1.2 g, 30 mmol, 60% dispersion in mineral oil) in DMF (50 mL) at 0° C. under an argon atmosphere. The mixture was stirred for 5 min and p-methoxybenzyl chloride (4.0 mL, 30.0 mmol) was added drop wise at the same temperature. The resulting mixture was warmed to room temperature and heated to reflux (bath temperature 110° C.) for 5 h. Thereafter, the mixture was cooled to room temperature, quenched with water (100 mL), and extracted with EtOAc (2×200 mL). The combined organic extracts were washed with water (3×100 mL), brine (50 mL), dried over anhydrous $Na_2SO_4$, filtered, and concentrated under reduced pressure. The crude product was recrystallized from $CH_2Cl_2$-hexanes to provide sultam 39-2 as a colorless crystalline solid.

(±)-3-Hydroxy-2-(4-methoxyphenyl)methyl-1,2-benzisothiazoline 1,1-dioxide (39-3)

DIBAL-H (25.4 mL, 23.5 mmol, 1.0 M solution in hexanes), was added drop wise to the solution of sultam 39-2 (6.5 g, 21.4 mmol) in $CH_2Cl_2$ (77 mL) at −78° C. under an argon atmosphere and the mixture was stirred for 1 h. The reaction was carefully quenched with 30% aqueous solution of Rochelle's salt and the resulting mixture was vigorously stirred at 25° C. for 3 h. The organic layer was separated and the aqueous layer was extracted with $CH_2Cl_2$ (2×100 mL). The combined organic layers were washed with brine (50 mL), dried over anhydrous $Na_2SO_4$, filtered and concentrated under reduced pressure. The crude product was recrystallized from EtOAc/hexanes to provide 3-hydroxy-sultam 39-3 as colorless oil.

(±)-3-Cyano-2-(4-methoxyphenyl)methyl-1,2-benzisothiazoline 1,1-dioxide (39-4)

$BF_3 \cdot Et_2O$ (1.2 mL, 9.7 mmol) and TMSCN (18.3 mL, 18.2 mmol) was added drop wise to a solution of 3-hydroxy-sultam 39-3 (2.80 g, 9.16 mmol) in $CH_2Cl_2$ (35 mL) at −78° C. under an argon atmosphere and mixture was stirred for 1 h. The mixture was warmed to 0° C. and quenched with saturated aqueous $NaHCO_3$ solution (pH 8). The organic layer was separated, washed with brine (50 mL), dried over anhydrous $Na_2SO_4$, filtered, and concentrated under reduced pressure. The crude product was recrystallized from $CH_2Cl_2$/hexanes to provide nitrile 39-4 as amorphous white solid.

(±)-3-Methoxycarbonyl-2-(4-methoxyphenyl) methyl-1,2-benzisothiazoline 1,1-dioxide (39-5)

MeOH (20 mL) and acetyl chloride (4.0 mL, 55.8 mmol) were added sequentially to a solution of nitrile 39-4 (1.2 g, 3.82 mmol) in anhydrous 1,4-dioxane (10 mL) at 0° C. The mixture was warmed to 25° C. and was stirred for 3 days. The mixture was quenched with water (50 mL) and extracted with EtOAc (3×50 mL). The combined organic phase was washed with an aqueous saturated $NaHCO_3$ solution (20 mL), water (2×20 mL), and brine (20 mL), dried over anhydrous $Na_2SO_4$, filtered and concentrated under reduced pressure to give ester 39-5 as a colorless oil.

(±)-3-Methoxycarbonyl-1,2-benzisothiazoline-1,1-dioxide (39-6)

A solution of ceric ammonium nitrate (8.45 g, 15.1 mmol) in water (15 mL) was added drop wise to the solution of sultam 39-5 (1.37 g, 3.94 mmol) in $CH_3CN$ (46 mL) at room temperature and mixture was stirred at room temperature for 1 h. The solvent was removed under reduced pressure, diluted with water (20 mL) and extracted with EtOAc (3×50 mL). The combined organic extract was washed with brine (20 mL), dried over anhydrous $Na_2SO_4$, filtered and concentrated under reduced pressure. The residue was purified by column chromatography (silica gel, eluent: 30-70%) EtOAc/hexanes to provide ester 39-6 as a brown solid.

(±)-3-Carboxy-1,2-benzisothiazoline 1,1-dioxide (39-7)

A solution of LiOH (123 mg, 5.1 mmol) in water (2 mL) was added drop wise to the solution of ester 39-6 (370 mg, 1.63 mmol) in THF (5 mL) at room temperature and mixture was stirred for 10 min. The solvent was removed under reduced pressure, the residue was diluted with water (20 mL), washed with MTBE (1×20 mL). The aqueous layer was acidified with 2N HCl to pH 2, and extracted with EtOAc (2×50 mL). The combined organic layers were washed with brine, dried over anhydrous $Na_2SO_4$, filtered, and concentrated under reduced pressure to provide 3-carboxysultam 39-7 as a white solid.

tert-Butyl-4-chloro-2-[{(2S)-1-(1,1-dioxido-2,3-dihydrobenzo[d]isothiazole-3-carbonyl)pyrrolidine-2-carboxamido}methyl]benzylcarbamate (39-9)

Diisopropylethyl amine (0.36 mL, 2.03 mmol) was added to the mixture of amine 39-8 (620 mg, 1.69 mmol), acid 40-7 (360 mg, 1.69 mmol) and HATU (706 mg, 1.86 mmol) in DMF (5.0 mL) at 0° C. and mixture was stirred at room temperature for 2 h. The reaction mixture was quenched with water (20 mL) and extracted with EtOAc (2×50 mL). The combined organic layer was washed with saturated aqueous $NaHCO_3$ (25 mL), water (2×50 mL), brine (20 mL), dried over anhydrous $Na_2SO_4$ and concentrated under reduced pressure. The residue was purified by column chromatography (silica gel, EtOAc/hexanes: 20-30%) to provide amide 39-9 as diastereomeric mixture as pale yellow gummy solid.

(S)—N-{2-(Aminomethyl)-5-chlorobenzyl}-1-(5-ethoxy-1H-pyrrole-2-carbonyl)pyrrolidine-2-carboxamide (39-10)

Trifluoroacetic acid (1.2 mL, 15.6 mmol) and water (100 μL) were added to a solution of boc amine 39-9 (0.58 g, 1.04 mmol) in $CH_2Cl_2$ (10.0 mL) and mixture was stirred at room temperature for 16 h. The solvent and volatiles were removed under reduced pressure and residue was purified by column chromatography (C18: $CH_3CN$/water: 10-40%) to provide diastereomer 39-10a (243 mg) as amorphous white solid and diastereomer 39-10b as amorphous white solid.

39-10a: $^1$H NMR (400 MHz, $CDCl_3$) (mixture of rotamers): δ 7.81-7.74 (m, 1H ), 7.71-7.59 (m, 2H ), 7.54-7.47 (m, 1H), 7.44 (s, 1H), 7.40-7.32 (m, 2H), 5.61 (s, 0.3H), 5.59 (s, 0.7 H), 4.65 (d, J=14.2 Hz, 0.4 H), 4.48-4.32 (m, 2.6H), 4.32-4.10 (m, 2H), 4.02-3.81 (m, 2H), 2.36-2.25 (m, 1H), 2.22-2.11 (m, 1H), 2.12-1.91 (m, 2H)

39-10b: $^1$H NMR (300 MHz, $CDCl_3$) (mixture of rotamers): δ 7.81-7.71 (m, 1H ), 7.71-7.58 (m, 2H ), 7.53-7.47 (m, 1H), 7.44 (s, 1H), 7.40-7.32 (m, 2H), 5.61 (s, 0.3H), 5.60 (s, 0.7 H), 4.65 (d, J=15.0 Hz, 0.4 H), 4.50-4.23 (m, 2.6H), 4.22-4.08 (m, 2H), 4.02-3.79 (m, 2H), 2.38-2.23 (m, 1H), 2.23-1.89 (m, 3H)

EXAMPLE 40

Preparation of (5)-1-(1-Aminocyclopentanecarbonyl)-N-{2-(aminomethyl)-5-chlorobenzyl}pyrrolidine-2-carboxamide-2,2,2-trifluoroacetate (40-4)

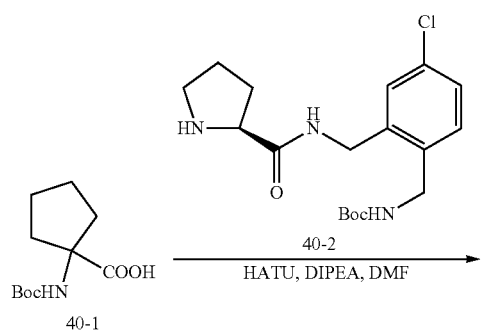

tert-Butyl 2-[{(S)-1-{(R)-2-(benzyloxy)-2-phenylacetyl}pyrrolidine-2-carboxamido}methyl]-4-chlorobenzylcarbamate (40-3)

The mixture of acid 40-1 (0.1 g, 0.44 mmol), amine 40-2 (0.17 g, 0.48 mmol), HATU (0.18 g, 0.48 mmol), DIPEA (0.24 mL, 1.32 mL) in anhydrous DMF (10 mL) was stirred under nitrogen at room temperature for 2 h. The reaction mixture was quenched with water (50 mL), extracted with EtOAc (3×25 mL). The combined organic layer was washed with saturated aqueous solution of $NaHCO_3$ (2×25 mL), brine solution (25 mL), dried over anhydrous $Na_2SO_4$, filtered and concentrated under reduced pressure. The residue was purified by silica gel combiflash column chromatography (C18; eluent: 10-100% acetonitrile:water) to afford amide 40-3 as a brown solid.

(S)-1-(1-Aminocyclopentanecarbonyl)-N-{2-(aminomethyl)-5-chlorobenzyl}pyrrolidine-2-carboxamide-2,2,2-trifluoroacetate (40-4)

Trifluoro acetic acid (1 mL, 60 mmol) was added drop wise to a stirred solution of amide 40-3 (0.12 g, 0.21 mmol) in $CH_2Cl_2$ (5 mL) and mixture was stirred at room temperature for 2 h. The solvent and volatiles were removed at reduced pressure. The residue was purified by reverse phase combiflash column chromatography (C18: eluent: 0-40% acetonitrile/water) to obtain 40-4. $^1$H NMR (DMSO-$d_6$, 400 MH$_z$) (δ) ppm: 8.62 (s, 1H), 8.41-7.98 (m, 6H), 7.49-7.38 (m, 3H), 4.44-4.41 (m, 1H), 4.35-4.34 (m, 2H), 4.10-4.02 (m, 2H), 3.59-3.53 (m, 2H), 2.32-2.31 (m, 2H), 2.13-2.12 (m, 1H), 1.97-1.83 (m, 8H), 1.70-1.67 (m, 1H).

EXAMPLE 41

Preparation of (S)—N-{2-(Aminomethyl)-5-chlorobenzyl}-1-{1-(methylsulfonamido)cyclopentanecarbonyl}pyrrolidine-2-carboxamide-2,2,2-trifluoroacetate (41-5)

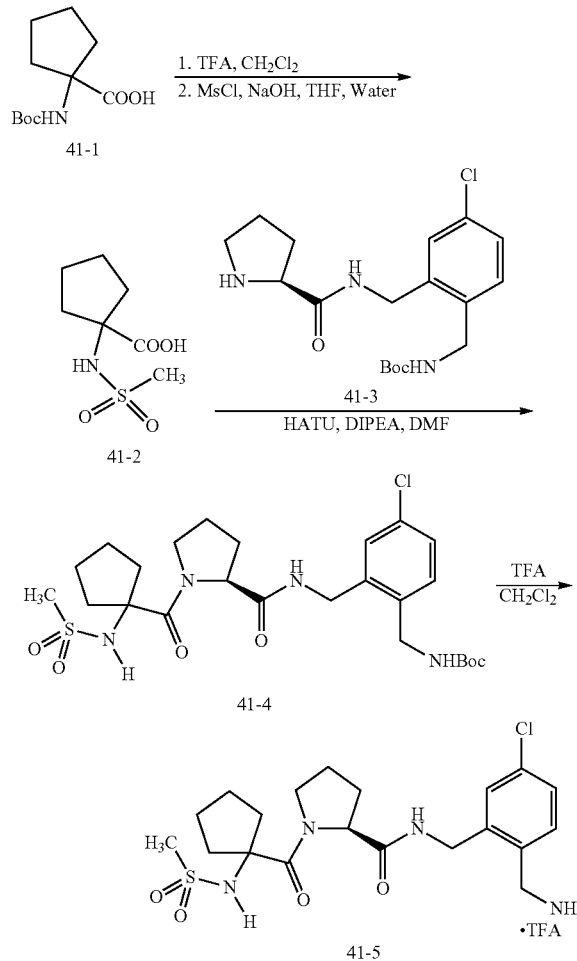

1-Aminocyclopentanecarboxylic acid (41-2)

Trifluoro acetic acid (2 mL, 120 mmol) was added drop wise to the stirred solution of Boc-amino acid 41-1 (0.5 g, 2.18 mmol) in CH$_2$Cl$_2$ (10 mL), and mixture was stirred at room temperature for 4 h. The solvent and volatiles were removed at reduced pressure and residue was dried under high vacuum to obtain 1-aminocyclopentanecarboxylic acid compound with 2,2,2-trifluoroacetic acid.

A 2N solution of sodium hydroxide (5.45 mL, 10.9 mmol) and methane sulfonyl chloride (0.51 g, 6.54 mmol) was added to the solution of above amino acid in THF (20 mL) and mixture was stirred at room temperature for 16 h. The organic solvent was removed at reduced pressure. The mixture was diluted with water (10 mL), acidified with aqueous 1N HCl to pH 3, and extracted with EtOAc (3×25 mL). The combined organic extracts were dried over anhydrous Na$_2$SO$_4$, filtered and concentrated under reduced pressure. The residue was purified by reverse phase combiflash column chromatography (C18; eluent: 10-100% acetonitrile/water) to afford sulphonamide 41-2 as a brown semi-solid.

(S)-tert-Butyl 4-chloro-2-[{1-(1-(methylsulfonamido)cyclopentane carbonyl)pyrrolidine-2-carboxamido}methyl]benzylcarbamate (41-4)

The mixture of acid 41-2 (0.06 g, 0.29 mmol), amine 41-3 (0.11 g, 0.29 mmol), HATU (0.12 g, 0.32 mmol), DIPEA (0.15 mL, 0.87 mL) in anhydrous DMF (10 mL) and was stirred under nitrogen at room temperature for 2 h. The reaction mixture was quenched with water (50 mL), extracted with EtOAc (3×25 mL). The combined organic layer was washed with saturated aqueous solution of NaHCO$_3$ (2×25 mL), brine solution (25 mL), dried over anhydrous Na$_2$SO$_4$, filtered and concentrated under reduced pressure. The residue was purified by silica gel combiflash column chromatography (C18; eluent: 10-100% acetonitrile/water) to afford amide 41-4 as a brown solid.

(S)—N-{2-(Aminomethyl)-5-chlorobenzyl}-1-{1-(methylsulfonamido)cyclopentanecarbonyl}pyrrolidine-2-carboxamide-2,2,2-trifluoroacetate (41-5)

Trifluoro acetic acid (0.5 mL, 30 mmol) was added drop wise to a stirred solution of amide 41-4 (0.08 g, 0.14 mmol) in CH$_2$Cl$_2$ (3 mL) and mixture was stirred at room temperature for 2 h. The solvent and volatiles were removed at reduced pressure and dried under high vacuum. The residue was purified by reverse phase combiflash column chromatography (C18: eluent: 0-30% acetonitrile/water) to obtain 41-5. $^1$H NMR (DMSO-d$_6$, 400 MH$_Z$) (δ) ppm: 8.13-8.09 (m, 4H), 7.73 (s, 1H), 7.42-7.40 (m, 3H), 4.48-4.27 (m, 3H), 4.09 (s, 2H), 3.87-3.84 (m, 1H), 3.74-3.71 (m, 1H), 2.95 (s, 3H), 2.31-2.24 (m, 1H), 2.22-2.06 (m, 2H), 1.94-1.86 (m, 4H), 1.71-1.56 (m, 5H).

EXAMPLE 42

Preparation of (S)—N-(2-(Aminomethyl)-5-chlorobenzyl)-1-(pyrimidine-2-carbonyl)pyrrolidine-2-carboxamide bis(2,2,2-trifluoroacetate) (42-3)

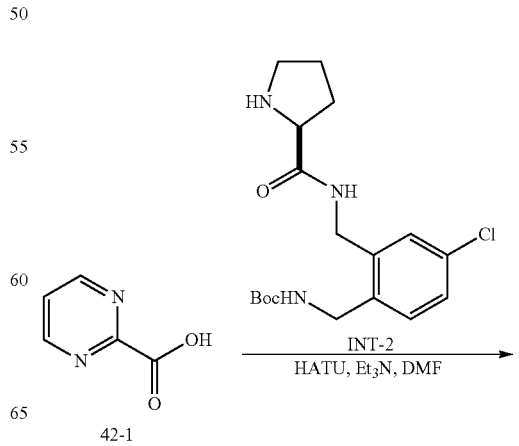

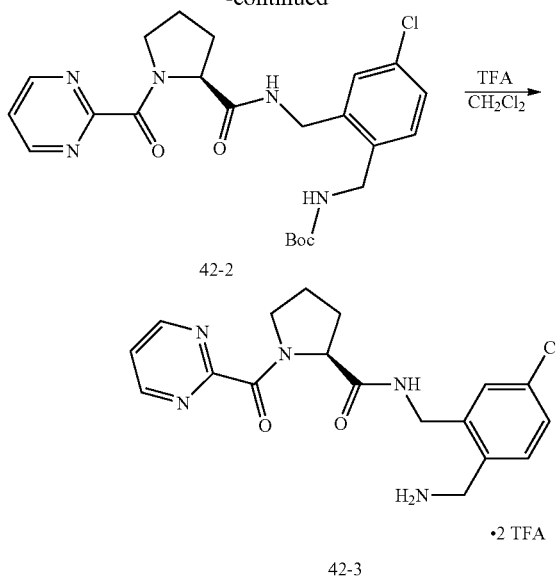

42-2

42-3 · 2 TFA (S)-tert-Butyl-4-chloro-2-[{1-(pyrimidine-2-carbonyl)pyrrolidine-2-carboxamido}methyl]benzylcarbamate (42-2)

A mixture of acid 42-1 (0.10 g, 0.80 mmol), amine 1-10 (0.29 g, 0.80 mmol), HATU (0.61 g, 1.61 mmol) and Et$_3$N (0.34 mL, 2.41 mmol) in DMF (10 mL) was stirred under nitrogen for 3 h at room temperature. The reaction was quenched with water (100 mL) and extracted with EtOAc (3×20 mL). The combined organic layer was washed with water (2×100 mL), brine (50 mL), dried over anhydrous Na$_2$SO$_4$ and concentrated under reduced pressure. The residue was purified by reverse phase combiflash chromatography (C18, eluent: 0-30% H$_2$O/CH$_3$CN) to afford the amide 42-2 as a colorless oil.

(S)—N-[2-(Aminomethyl)-5-chlorobenzyl]-1-(pyrimidine-2-carbonyl)pyrrolidine-2-carboxamide bis (2,2,2-trifluoroacetate) (42-3)

A 50% solution of Trifluoroacetic acid in CH$_2$Cl$_2$ (5 mL) was added to the solution of Boc protected amine 42-2 (0.14 g, 0.29 mmol) in CH$_2$Cl$_2$ (5 mL) and the reaction mixture was stirred under nitrogen for 2 h. The solvent was removed at reduced pressure and the residue was azeotroped with toluene (8 mL). Hygroscopic solid was obtained dissolved in 1:1 acetonitrile/water (4 mL) and lyophilized for 24 h to obtain 42-3 as hygroscopic off-white solid. $^1$H NMR (300 MHz, MeOD-d$_4$) δ 8.91 (d, J=5.1 Hz, 1H), 8.56, (d, J=4.8 Hz, 1H), 7.59 (t, J=5.1 Hz, 1H), 7.25-7.48 (m, 3H), 4.89-4.81 (m, 1H), 4.62-4.53 (m, 1H), 4.37-4.13 (m, 1H), 4.18-4.13 (m, 2H), 3.85-3.73 (m, 2H), 2.40-2.21 (m, 1H), 2.15-1.90 (m, 3H)

In Vitro Assay for Determining Proteinase Inhibition

Relevant in vitro assays are referenced in Morrissette, et al., Bioorg. Med. Chem. Lett. 2004, 14, 4161-4164 and described in Lewis, et al. Thromb. Res. 1993, 70, 173 (assays of human α-thrombin and human trypsin), and Lewis, et al. Thromb. Haemostasis 1995, 74, 1107-1112. The assays were carried out at 25° C. in 0.05 M TRIS buffer pH 7.4, 0.15 M NaCl, 0.1% PEG. Trypsin assays also contained 1 mM CaCl2. In assays wherein rates of hydrolysis of a p-nitroanilide (pna) substrate were determined, a Thermomax 96-well plate reader was used was used to measure (at 405 nm) the time dependent appearance of p-nitroaniline. sar-PR-pna was used to assay human α-thrombin (K$_m$=125 μM) and bovine trypsin (K$_m$=125 μM). p-Nitroanilide substrate concentration was determined from measurements of absorbance at 342 nm using an extinction coefficient of 8270 cm$^{-1}$M$^{-1}$.

In certain studies with potent inhibitors (K$_i$<10 nM) where the degree of inhibition of thrombin was high, a more sensitive activity assay was employed. In this assay the rate of thrombin catalyzed hydrolysis of the fluorogenic substrate benzyloxycarbonyl-Gly-Pro-Arg-7-amino-4-trifluoromethylcoumarin (Z-GPR-afc, Lewis S. D. et al. (1998) J. Biol. Chem. 273, pp. 4843-4854) (K$_m$=27 μM) was determined from the increase in fluorescence at 500 nm (excitation at 400 nm) associated with production of 7-amino-4-trifluoromethyl coumarin. Concentrations of stock solutions of Z-GPR-afc were determined from measurements of absorbance at 380 nm of the 7-amino-4-trifluoromethyl coumarin produced upon complete hydrolysis of an aliquot of the stock solution by thrombin.

Activity assays were performed by diluting a stock solution of substrate at least tenfold to a final concentration ≤0.1 K$_m$ into a solution containing enzyme or enzyme equilibrated with inhibitor. Times required to achieve equilibration between enzyme and inhibitor were determined in control experiments. Initial velocities of product formation in the absence (V$_o$) or presence of inhibitor (V$_i$) were measured. Assuming competitive inhibition, and that unity is negligible compared K$_m$/[S], [I]/e, and [I]/e (where [S], [I], and e respectively represent the total concentrations, of substrate, inhibitor and enzyme), the equilibrium constant (K$_i$) for dissociation of the inhibitor from the enzyme can be obtained from the dependence of V$_o$/V$_i$ on [I] shown in the following equation.

$$V_o/V_i = 1 + [I]/K_i$$

The activities shown by this assay indicate that the compounds of the invention may be therapeutically useful for treating various conditions in patients suffering from unstable angina, refractory angina, myocardial infarction, transient ischemic attacks, atrial fibrillation, thrombotic stroke, embolic stroke, deep vein thrombosis, disseminated intravascular coagulation, and reocclusion or restenosis of recanalized vessels.

Tablets containing 25, 50, and 100 mg., respectively, of the following active compounds are prepared as illustrated below (compositions A-C). Active I is (S)—N-[2-(Aminomethyl)-5-chlorobenzyl]-1-[(R)-2-(2-hydroxyethyl)-3,3-dimethylbutanoyl]pyrrolidine-2-carboxamide-2,2,2-trifluoroacetate.

|  | Amount-(mg) | | |
| --- | --- | --- | --- |
| Component | A | B | C |
| Active I | 25 | 50 | 100 |
| Microcrystalline cellulose | 37.25 | 100 | 200 |
| Modified food corn starch | 37.25 | 4.25 | 8.5 |
| Magnesium stearate | 0.5 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25, 50, and 100 mg, respectively, of active ingredient per tablet.

Exemplary compositions of (5)-N-[2-(Aminomethyl)-5-chlorobenzyl]-1-[(R)-2-(2-hydroxyethyl)-3,3-dimethylbutanoyl]pyrrolidine-2-carboxamide-2,2,2-trifluoroacetate (Active I) tablets are shown below:

| Component | 0.25 mg | 2 mg | 10 mg | 50 mg |
|---|---|---|---|---|
| Active I | 0.500% | 1.000% | 5.000% | 14.29% |
| mannitol | 49.50% | 49.25% | 47.25% | 42.61% |
| microcrystalline cellulose | 49.50% | 49.25% | 47.25% | 42.61% |
| magnesium stearate | 0.500% | 0.500% | 0.500% | 0.500% |

0.25, 2, 10 and 50 mg tablets were film-coated with an aqueous dispersion of hydroxypropyl cellulose, hydroxypropyl methylcellulose and titanium dioxide, providing a nominal weight gain of 2.4%.

Active I, mannitol and microcrystalline cellulose were sieved through mesh screens of specified size (generally 250 to 750 μm) and combined in a suitable blender. The mixture was subsequently blended (typically 15 to 30 min) until the drug was uniformly distributed in the resulting dry powder blend. Magnesium stearate was screened and added to the blender, after which a precompression tablet blend was achieved upon additional mixing (typically 2 to 10 min). The precompression tablet blend was then compacted under an applied force, typically ranging from 0.5 to 2.5 metric tons, sufficient to yield tablets of suitable physical strength with acceptable disintegration times (specifications will vary with the size and potency of the compressed tablet). In the case of the 2, 10 and 50 mg potencies, the tablets were dedusted and film-coated with an aqueous dispersion of water-soluble polymers and pigment.

Alternatively, a dry powder blend is compacted under modest forces and remilled to afford granules of specified particle size. The granules are then mixed with magnesium stearate and tabletted as stated above.

Intravenous formulations (S)—N-[2-(Aminomethyl)-5-chlorobenzyl]-1-[(R)-2-(2-hydroxyethyl)-3,3-dimethylbu-tanoyl]pyrrolidine-2-carboxamide-2,2,2-trifluoroacetate (Active I) were prepared according to general intravenous formulation procedures.

| Component | Estimated range |
|---|---|
| Active I | 0.12-0.50 mg |
| D-glucuronic acid | 0.5-5 mg |
| Mannitol NF | 50-53 mg |
| 1N Sodium Hydroxide | q.s. pH 3.9-4.1 |
| Water for injection | q.s. 1.0 mL |

Various other buffer acids, such as L-lactic acid, acetic acid, citric acid or any pharmaceutically acceptable acid/conjugate base with reasonable buffering capacity in the pH range acceptable for intravenous administration may be substituted for glucuronic acid.

What is claimed is:

1. A compound of the formula I

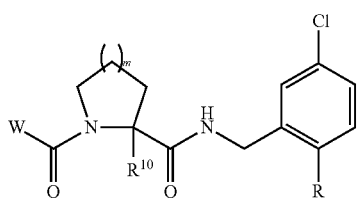

(I)

or a pharmaceutically acceptable salt thereof, wherein m is 0 or 1;
R is a heterocycle, —$(CR^8R^9)_{1-2}NH_2$, or —$(CR^8R^9)_{1-2}OH$, wherein $R^8$ and $R^9$, each time in which they occur, are independently H, $C_{1-6}$ alkyl, —$CH_2F$, —$CHF_2$, $CF_3$ or —$CH_2OH$;

W is
a) —$CHR^1R^2$, where $R^1$ is —$C(CH_3)_3$, and $R^2$ is —$(CH_2)_{1-2}OH$,
b) a 5- or 6-membered unsubstituted or substituted heterocycle having 1 or 2 heteroatoms selected from N and O, wherein substituted heterocycle is substituted with $R^3$,
c) a 9- or 10-membered unsubstituted or substituted heterocycle having 1 or 2 heteroatoms selected from N, O and S, wherein substituted heterocycle is monosubstituted with $R^3$, or disubstituted with $R^3$ and $R^4$, or
d) a 3-, 4-, or 5-membered carbocyclic ring which is unsubstituted, mono-substituted with $R^3$, di-substituted with $R^3$ and $R^4$, or tri-substituted with $R^3$, $R^4$ and $R^5$;
$R^3$ is —$CF_3$, —COOH, —$COOR^7$, —$C(O)R^6$, —CH(OH)$R^6$, —$CH_2R^6$, $R^6$, =O, halogen, $R^7$, —OH, —$NH_2$, or —$NHSO_2R^7$;
$R^4$ is —OH, =O, or $C_{1-6}$ alkyl;
$R^5$ is $C_{1-6}$ alkyl;
$R^6$ is

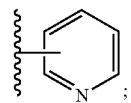

$R^7$ is $C_{1-6}$ alkyl;
$R^{10}$ is H or $C_{1-6}$ alkyl.

2. A compound of claim 1, or a pharmaceutically acceptable salt thereof, wherein R is —$CH_2NH_2$, —$CH_2OH$ or tetrazole.

3. A compound of claim 2, or a pharmaceutically acceptable salt thereof, wherein R is —$CH_2NH_2$ or tetrazole.

4. A compound of claim 1, or a pharmaceutically acceptable salt thereof, wherein W is —$CH(C(CH_3)_3)CH_2CH_2OH$, or —$CH(C(CH_3)_3)CH_2OH$.

5. A compound of claim 1, or a pharmaceutically acceptable salt thereof, wherein W is

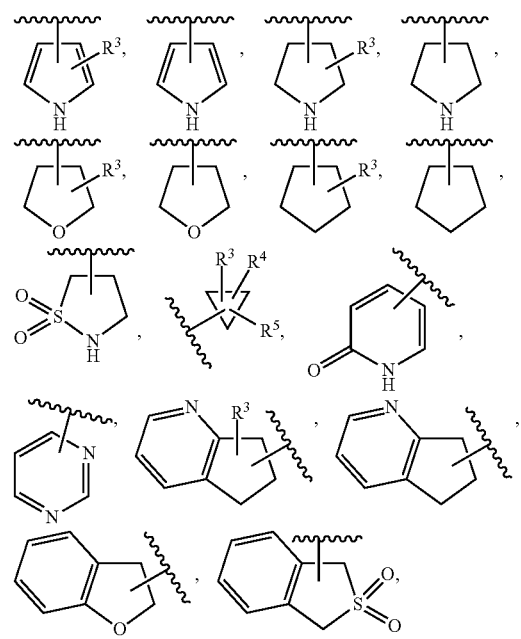

-continued

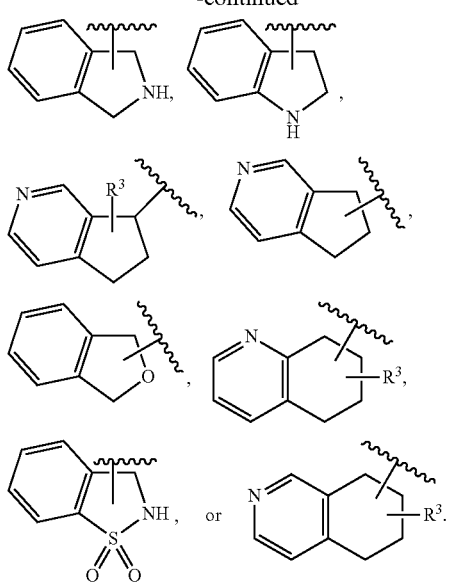

6. A compound of claim 5, or a pharmaceutically acceptable salt thereof, wherein W is

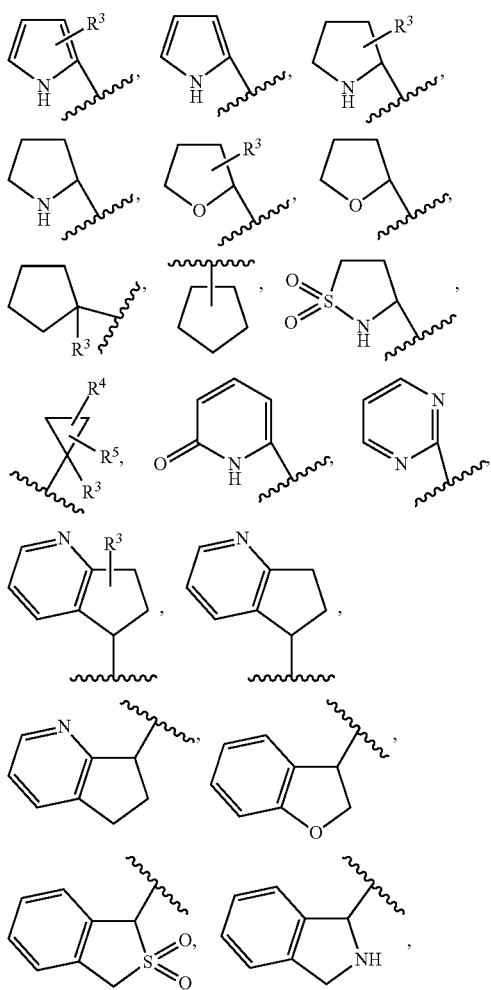

-continued

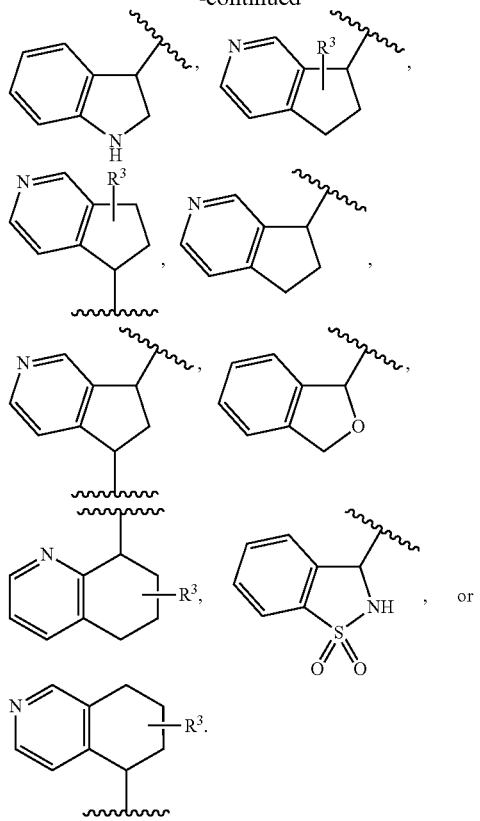

7. A compound of claim 1, or a pharmaceutically acceptable salt thereof, wherein $R^3$ is —$CF_3$, COOH, —$COOCH_2CH_3$, Cl, OH, $NH_2$, $NHSO_2CH_3$,

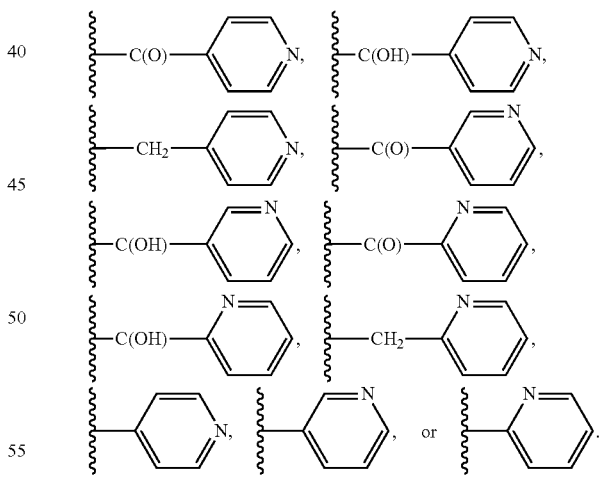

8. A compound of claim 1, or a pharmaceutically acceptable salt thereof, wherein $R^4$ is $CH_3$.
9. A compound of claim 1, or a pharmaceutically acceptable salt thereof, wherein $R^5$ is $CH_3$.
10. A compound of claim 1, or a pharmaceutically acceptable salt thereof, wherein $R^7$ is $CH_3$.
11. A compound of claim 1, or a pharmaceutically acceptable salt thereof, wherein $R^{10}$ is H.
12. A compound of claim 1, or a pharmaceutically acceptable salt thereof, wherein $R^{10}$ is $CH_3$.

13. A compound of claim 1, or pharmaceutically acceptable salt thereof, which is
- (S)—N-[2-(Aminomethyl)-5-chlorobenzyl]-1-[(R)-2-(2-hydroxyethyl)-3,3-dimethylbutanoyl]pyrrolidine-2-carboxamide-2,2,2-trifluoroacetate,
- (S)—N-[2-(Aminomethyl)-5-chlorobenzyl]-1-[4-(trifluoromethyl)-1H-pyrrole-2-carbonyl]pyrrolidine-2-carboxamide-2,2,2-trifluoroacetate,
- (S)-Ethyl-5-[2-{(2-(aminomethyl)-5-chlorobenzyl)carbamoyl}pyrrolidine-1-carbonyl]-1H-pyrrole-2-carboxylate-2,2,2-trifluoroacetate,
- (S)—N-{2-(Aminomethyl)-5-chlorobenzyl}-1-{5-(trifluoromethyl)-1H-pyrrole-2-carbonyl}pyrrolidine-2-carboxamide,
- (S)—N-{2-(Aminomethyl)-5-chlorobenzyl}-1-(4-nicotinoyl-1H-pyrrole-2-carbonyl)pyrrolidine-2-carboxamide-bis(2,2,2-trifluoro acetate),
- (2S)-N-{2-(Aminomethyl)-5-chlorobenzyl}-1-[4-{hydroxyl (pyridine-4-yl)methyl}-1H-pyrrole-2-carbonyl]pyrrolidine-2-carboxamide-bis(2,2,2-trifluoroacetate),
- (S)—N-{2-(Aminomethyl)-5-chlorobenzyl}-1-{4-(pyridin-4-ylmethyl)-1H-pyrrole-4-carbonyl}pyrrolidine-2-carboxamide-bis(2,2,2-trifluoroacetate),
- (S)—N-{2-(aminomethyl)-5-chlorobenzyl}-1-(4-nicotinoyl-1H-pyrrole-2-carbonyl)pyrrolidine-2-carboxamide-bis-2,2,2-trifluoro acetate,
- (2S)-N-{2-(Aminomethyl)-5-chlorobenzyl}-1-[4-{hydroxy (pyridine-3-yl }methyl]-1H-pyrrole-2-carbonyl)pyrrolidine-2-carboxamide,
- (S)—N-{2-(Aminomethyl)-5-chlorobenzyl}-1-(4-picolinoyl-1H-pyrrole-2-carbonyl)pyrrolidine-2-carboxamide-bis(2,2,2-trifluoro acetate,
- (2S)-N-{2-(Aminomethyl)-5-chlorobenzyl}-1-[4-{hydroxyl(pyridine-2-yl)methyl}-1H-pyrrole-2-carbonyl]pyrrolidine-2-carboxamide,
- (S)—N-{2-(Aminomethyl)-5-chlorobenzyl}-1-{4-(pyridin-2-ylmethyl)-1H-pyrrole-2-carbonyl}pyrrolidine-2-carboxamide-bis(2,2,2-trifluoroacetate),
- (S)—N-{2-(Aminomethyl)-5-chlorobenzyl)-1-}4-(pyridin-4-yl)-1H-pyrrole-2-carbonyl)pyrrolidine-2-carboxamide-bis(2,2,2-trifluoroacetate),
- (S)—N-{2-(Aminomethyl)-5-chlorobenzyl}-1-{4-(pyridin-3-yl)-1H-pyrrole-2-carbonyl}pyrrolidine-2-carboxamide bis(2,2,2-trifluoroacetate),
- (S)—N-[{2-(Aminomethyl)-5-chlorobenzyl}-1-{4-(pyridin-2-yl)-1H-pyrrole-2-carbonyl}]pyrrolidine-2-carboxamide bis (2,2,2-trifluoroacetate),
- (S)—N-{2-(aminomethyl)-5-chlorobenzyl}-1-{(S)-2-(hydroxymethyl)-3,3-dimethylbutanoyl}pyrrolidine-2-carboxamide-2,2,2-trifluoroacetate,
- (S)—N-{5-Chloro-2-(hydroxymethyl)benzyl}-1-{(R)-2-hydroxy-3,3-dimethyl butanoyl}pyrrolidine-2-carboxamide,
- (S)—N-}2-(Aminomethyl)-5-chlorobenzyl}-1-(6-oxo-1,6-dihydropyridine-2-carbonyl)pyrrolidine-2-carboxamide-2,2,2-trifluoroacetate,
- (2S)-N-{2-(Aminomethyl)-5-chlorobenzyl}-1-(5-hydroxy-6,7-dihydro-5H-cyclopenta[b]pyridine-5-carbonyl)pyrrolidine-2-carboxamide-2,2,2-trifluoroacetate,
- (2S)-N-(2-(Aminomethyl)-5-chlorobenzyl)-1-(7-hydroxy-6,7-dihydro-5H-cyclopenta[b]pyridine-7-carbonyl)pyrrolidine-2-carboxamide-bis(2,2,2-trifluoro acetate),
- (2S)-N-{2-(Aminomethyl)-5chlorobenzyl}-1-(1,3-dihydroisobenzofuran-1-carbonyl)pyrrolidine-2-carboxamide-2,2,2-trifluoroacetate,
- (2S)-N-{2-(Aminomethyl)-5chlorobenzyl}-1-(2,2-dioxido-1,3-dihydrobenzo[a]thiophene-1-carbonyl)pyrrolidine-2-carboxamide-2,2,2-trifluoroacetate-2,2,2-trifluoroacetate,
- (2S)-N-{2-(Aminomethyl)-5-chlorobenzyl}-1-(isoindoline-1-carbonyl)pyrrolidine-2-carboxamide bis(2,2,2-trifluoroacetate),
- (2S)-N-{2-(Aminomethyl)-5-chlorobenzyl}-1-(isoindoline-1-carbonyl)pyrrolidine-2-carboxamide bis(2,2,2-trifluoroacetate) Isomer A,
- (2S)-N-{2-(Aminomethyl)-5-chlorobenzyl}-1-(isoindoline-1-carbonyl)pyrrolidine-2-carboxamide bis(2,2,2-trifluoroacetate) Isomer B,
- (2S)-N-{2-(Aminomethyl)-5-chlorobenzyl}-1-(2,3-dihydrobenzofuran-3-carbonyl)pyrrolidine-2-carboxamide-2,2,2-trifluoroacetate,
- (2S)-N-{2-(Aminomethyl)-5-chlorobenzyl}-1-(indoline-3-carbonyl)pyrrolidine-2-carboxamide bis(2,2,2-trifluoroacetate),
- (2S)-N-}2-(Aminomethyl)-5-chlorobenzyl}-1-(5-hydroxy-6,7-dihydro-5H-cyclopenta[b]pyridine-5-carbonyl}azetidine-2-carboxamide bis(2,2,2-trifluoroacetate),
- {(2S)-N-2-(Aminomethyl)-5-chlorobenzyl}-1-(5-hydroxy-6,7-dihydro-5H-cyclopenta[c]pyridine-5-carbonyl)pyrrolidine-2-carboxamide bis(2,2,2-trifluoroacetate),
- (2S)-N-{2-(aminomethyl)-5-chlorobenzyl}-1-(7-hydroxy-6,7-dihydro-5H-cyclopenta[c]pyridine-7-carbonyl)pyrrolidine-2-carboxamide bis (2,2,2-trifluoroacetate),
- (2S)-1-(7-Amino-6,7-dihydro-5H-cyclopenta[b]pyridine-7-carbonyl)-N-(2-(aminomethyl)-5-chlorobenzyl)pyrrolidine-2-carboxamide tris(2,2,2-trifluoroacetate),
- (2S)-1-(7-Amino-6,7-dihydro-5H-cyclopenta[b]pyridine-7-carbonyl)-N-(2-(aminomethyl)-5-chlorobenzyl)pyrrolidine-2-carboxamide tris(2,2,2-trifluoroacetate) Isomer A,
- (2S)-1-(7-Amino-6,7-dihydro-5H-cyclopenta[b]pyridine-7-carbonyl)-N-(2-(aminomethyl)-5-chlorobenzyl)pyrrolidine-2-carboxamide tris(2,2,2-trifluoroacetate) Isomer B,
- (2S)-N-{2-(Aminomethyl)-5-chlorobenzyl}-1-(5-hydroxy-5,6,7,8-tetrahydroquinoline-5-carbonyl)pyrrolidine-2-carboxamide bis(2,2,2-trifluoroacetate),
- (2S)-N-{2-(Aminomethyl)-5-chlorobenzyl}-1-(5-hydroxy-5,6,7,8-tetrahydroisoquinoline-5-carbonyl)pyrrolidine-2-carboxamide bis(2,2,2-trifluoroacetate),
- (2S)-N-{2-(aminomethyl)-5-chlorobenzyl}-1-(8-hydroxy-5,6,7,8-tetrahydroquinoline-8-carbonyl)pyrrolidine-2-carboxamide bis(2,2,2-trifluoroacetate),
- (2S)-N-{2-(Aminomethyl)-5-chlorobenzyl}-1-(1,3-dihydroisobenzofuran-1-carbonyl)azetidine-2-carboxamide-2,2,2-trifluoroacetate,
- (2S)-N-{2-(aminomethyl)-5-chlorobenzyl}-1-(isoindoline-1-carbonyl)azetidine-2-carboxamide bis(2,2,2-trifluoroacetate),
- (2S)-N-{2-(Aminomethyl)-5-chlorobenzyl}-1-(indoline-3-carbonyl)azetidine-2-carboxamide bis(2,2,2-trifluoroacetate),
- (2S)-N-{5-chloro-2-(1H-tetrazol-1-yl)benzyl}-1-(7-hydroxy-6,7-dihydro-5H-cyclopenta[b]pyridine-7-carbonyl)pyrrolidine-2-carboxamide,
- (S)—N-{2-(Aminomethyl)-5-chlorobenzyl}-1-{(R)-1-hydroxy-2,2-dimethylcyclopropanecarbonyl)pyrrolidine-2-carboxamide-2,2,2-trifluoroacetate, (S)—N-{2-(Aminomethyl)-5-chlorobenzyl}-1-{(R)-1-hydroxy-2,2-dimethylcyclopropanecarbonyl)pyrrolidine-2-carboxamide-2,2,2-trifluoroacetate Isomer A, (S)—N-12-(Aminomethyl)-5-chlorobenzyl}-1-{(R)-1-hydroxy-2,2-dimethylcyclopropanecarbonyl)pyrrolidine-2-carboxamide-2,2,2-trifluoroacetate Isomer B, (S)—N-{2-(Aminomethyl)-5-chlorobenzyl}-1-{(R)-tetrahydrofuran-2-carbonyl}pyrrolidine-2-carboxamide-2,2,2-trifluoroacetate, (S)—N-{2-(Aminomethyl)-5-chlorobenzyl}1-(5-ethoxy-1H-pyrrole-2-carbonyl)pyrrolidine-2-carboxamide-2,2,2-trifluoroacetate, (S)—N-{2-(Aminomethyl)-5-chlorobenzyl}-1-(5-ethoxy-1H-pyrrole-2-carbonyl)pyrrolidine-2-carboxamide-2,2,2-trifluoroacetate Isomer A, (S)—N-12-(Aminomethyl)-5-chlorobenzyl}1-(5-ethoxy-1H-pyrrole-2-carbonyl)pyrrolidine-2-carboxamide-2,2,2-trifluoroacetate Isomer B, (S)-1-(1-Aminocyclopentanecarbonyl)-N-{2-(aminomethyl)-5-chlorobenzyl}pyrrolidine-2-carboxamide-2,2,2-trifluoroacetate, (S)—N-{2-(Aminomethyl)-5-chlorobenzyl}-1-{1-(methylsulfonamido)cyclopentanecarbonyl}pyrrolidine-2-carboxamide-2,2,2-trifluoroacetate, (S)—N-(2-(Aminomethyl)-5-chlorobenzyl)-1-(pyrimidine-2-carbonyl)pyrrolidine-2-carboxamide bis(2,2,2-trifluoroacetate), (S)—N-(2-(aminomethyl)-5-chlorobenzyl)-2-methyl-1-((R)-5-oxopyrrolidine-2-carbonyl)pyrrolidine-2-carboxamide, (S)—N-(2-(aminomethyl)-5-chlorobenzyl)-1-(5-chloro-1H-pyrrole-2-carbonyl)-2-methylpyrrolidine-2-carboxamide, or (S)—N-(2-(aminomethyl)-5-chlorobenzyl)-2-methyl-1-(5-methyl-1H-pyrrole-2-carbonyl)pyrrolidine-2-carboxamide.

14. A composition for inhibiting thrombus formation in blood comprising a compound of claim 1 and a pharmaceutically acceptable carrier.

15. A method for inhibiting thrombin in blood comprising adding to the blood a composition of claim 14.

16. A method for inhibiting formation of blood platelet aggregates in blood comprising adding to the blood a composition of claim 14.

17. A method for inhibiting thrombus formation in blood comprising adding to the blood a composition of claim 14.

18. A method for treating venous thromboembolism and pulmonary embolism in a mammal comprising administering to the mammal a composition of claim 14.

19. A method for treating deep vein thrombosis in a mammal comprising administering to the mammal a composition of claim 14.

20. A method for treating thromboembolic stroke in humans and other mammals comprising administering to the mammal a composition of claim 14.

* * * * *